US007034108B1

(12) United States Patent
Nicosia et al.

(10) Patent No.: US 7,034,108 B1
(45) Date of Patent: Apr. 25, 2006

(54) MIMOTOPES OF HYPERVARIABLE REGION 1 OF THE E2 GLYCOPROTEIN OF HCV AND USES THEREOF

(75) Inventors: Alfredo Nicosia, Rome (IT); Armin Lahm, Rome (IT); Anna Tramontano, Rome (IT); Riccardo Cortese, Rome (IT)

(73) Assignee: Istituto di Ricerche di Biologia Molecolare P. Angeletti S.p.A., Pomezia (IT)

( * ) Notice: Subject to any disclaimer, the term of this patent is extended or adjusted under 35 U.S.C. 154(b) by 0 days.

(21) Appl. No.: 09/463,098

(22) PCT Filed: May 14, 1999

(86) PCT No.: PCT/EP99/03344

§ 371 (c)(1),
(2), (4) Date: May 15, 2000

(87) PCT Pub. No.: WO99/60132

PCT Pub. Date: Nov. 25, 1999

(30) Foreign Application Priority Data

May 19, 1998 (GB) ................................ 9810756

(51) Int. Cl.
*C07K 7/00* (2006.01)
(52) U.S. Cl. .................. 530/324; 530/350; 530/300; 424/228.1; 424/227.1; 424/226.12; 424/204.1
(58) Field of Classification Search ............... 435/490, 435/320.1; 530/324, 300; 424/228.1, 227.1, 424/226.12, 204.1
See application file for complete search history.

(56) References Cited

U.S. PATENT DOCUMENTS 5,643,768 A   7/1997   Kawasaki
5,658,754 A   8/1997   Kawasaki

FOREIGN PATENT DOCUMENTS

| WO | WO 92/01047 | 1/1992 |
| WO | WO 94/26306 | 11/1994 |
| WO | WO 94/26886 | 11/1994 |
| WO | WO 95/11922 | 5/1995 |
| WO | WO 95/14110 | 5/1995 |

OTHER PUBLICATIONS

Cormack, B. et al. "Regional Codon Randomization: Defining a TATA-Binding Protein Surface Required for RNA Polymerase III Transcription", Science, 1993, vol. 262, pp. 244-248.
Cortese, R. et al. "Epitope discovery using peptide libraries displayed on phage", Trends Biotechnol, 1994, vol., 12, pp. 262-267.
Cortese, R. et al. "Selection of biologically active peptides by phage display of random peptide libraries", Current Opinion in Biotechnology, 1996, vol. 7, pp. 616-621.
Farci, P. et al. "Prevention of hepatitis C virus infection in chimpanzees after antibody-mediated in vitro neutralization", Proc Natl Acad Sci USA, 1994, vol. 91, pp. 7792-7796.
Farci, P. et al. "Prevention of hepatitis C virus infection in chimpanzees by hyperimmune serume against the hypervariable region 1 of the envelope 2 protein", Proc Natl Acad Sci USA, 1996, vol. 93, pp. 15394-15399.
Folgori, A. et al. "A general strategy to identify mimotopes of pathological antigens using only random peptide libraries and human sera", The EMBO Journal, 1994, vol. 13, pp. 2236-2243.
Major, M. et al. "DNA-Based Immunization with Chimeric Vectors for the Induction of Immune Responses against the Hepatitis C Virus Nucleocapsid", Journal of Virology, 1995, vol. 69, pp. 5798-5805.
Mecchia, M. et al. "Nonrheumatoid IgM in Human Hepatitis C Virus-Associated Type II Cryoglobulinemia Recognize Mimotopes of the CD4-Like LAG-3 Protein", The Jouranl of Immunology, 1996, vol. 157, pp. 3727-3736.
Meola, A. et al. "Derivation of Vaccines From Mimotopes. Immunologic Properties of Human Hepatitis B Virus Surface Antigen Mimotopes Displayed on Filamentous Phage", The Journal of Immunology, 1995, vol. 154, pp. 3162-3172.
Pessi, A. et al. "Application of the Continuous-flow Polyamide Method to the Solid-phase Synthesis of a Multiple Antigen Peptide (MAP) based on the Sequence of a Malaria Epitope", J of Chem Soc, Chemical Communications, 1990, vol. 1, pp. 8-9.
Prezzi, C. et al. "Selection of Antigenic and Immunogenic Mimics of Hepatitis C Virus Using Sera from Patients", The Journal of Immunology, 1996, vol. 156, pp. 4504-4513.
Scarselli, E. et la. "Occurrence of Antibodies Reactive with More than One Variant of the Putative Envelope Glycoprotein (gp70) Hypervariable Region 1 in Viremic Hepatitis C Virus-Infected Patients", Journal of Virology, 1995, vol. 69, pp. 4407-4412.
Shimizu, Y. et al. "Evidence for in vitro replication of hepatitis C virus genome in a human T-cell line", Pro Natl Acad Sci USA, 1992, vol. 89, pp. 5477-5481.

(Continued)

*Primary Examiner*—T. D. Wessendorf
(74) *Attorney, Agent, or Firm*—Sheldon O. Heber; Jack L. Tribble

(57) ABSTRACT

Peptides which are mimotopes of the hypervariable region 1 (HVR1) of the putative envelope protein E2 of hepatitis C virus (HCV) are provided, useful in obtaining antibodies and raising an immune response cross-reactive against different strains of HCV.

6 Claims, 9 Drawing Sheets

OTHER PUBLICATIONS

Simmonds, P. et al. "Classification of hepatitis C virus into six major genotypes and a series of subtypes by phylogenetic analysis of the NS-5 region", Journal of General Virology, 1993, vol. 74, pp. 2391-2399.

Tam, J. "Synthetic peptide vaccine design: Synthesis and properties of a high-density multiple antigenic peptide system", Proc Natl Acad Sci USA, 1988, vol. 85, pp. 5409-5413.

Weiner, A. et al. "Variable and Hypervariable Domains Are Found in the Regions of HCV Corresponding to the Flavivirus Envelope and NS1 Proteins and the Pestivirus Envelope Glycoproteins", Virology, 1991, vol. 180, pp. 842-848.

Winter G. et al. "Man-made antibodies", Nature, 1991, vol. 349, pp. 293-299.

Kato, N. et al. "Characterization of Hypervariable Regions in the Putative Envelope Protein of Hepatits C Virus", Biochem and Biophys Res Commun, 1992, vol. 189, pp. 119-127.

Takeuchi, K. et al. "Hepatitis C viral cDNA clones isolated from a healthy carrier donor implicated in post-transfusion non-A, non-B hepatitis", Gene, 1990, vol. 91, pp. 287-291.

Hohne, M. et al. "Sequence variability in the env-coding region of hepatitis C virus isolated from patients infected during a single source outbreak", Arch Virol, 1994, vol. 137, pp. 25-34.

Wang, Y. et al. "Prevalence, Genotypes, and an Isolate (HC-C2) of Hepatitis C Virus in Chinese Patients With Liver Disease", Journal of Medical Virology, 1993, vol. 40, pp. 254-260.

Okamoto, H. et al. "Molecular and clinical characteristics of the hepatitis C virus genotype "2c" found in Italians in Italy and France", International Hepatology Communications, 1995, vol. 3, pp. 161-165.

Kato, N. et al. "Molecular cloning of the human hepatitis C virus genome from Japanese patients with non-A, non-B hepatitis", Proc Natl Acad Sci USA, 1990, vol. 87, pp. 9524-9528.

Okamoto, H. et al. "The entire nucleotide sequence and classification of a hepatitis C virus isolate of a novel genotype from an Idonesian patient with chronic liver disease", Journal of General Virology, 1994, vol. 75, pp. 629-635.

Kato, N. et al. "Marked sequence diversity in the putative envelope proteins of hepatitis C viruses ", Virus Research, 1992, vol. 22, pp. 107-123.

Sarashina, T. et al. "Nucleotide sequence of the hepatitis C virus genome from a patient negative for anti-HCV by the first generation antibody assay", Nucleic Acids Research, 1993, vol. 21, pp. 1037.

Tokita, H. et al. "Hepatitis C virus variants from Vietnam are classifiable into the seventh, eighth, and ninth major genetic groups", Proc Natl Acad Sci USA, 1994, vol. 91, pp. 11022-11026.

Abe, K. et al. "Genomic characterization and mutation rate of hepatitis C virus isolated from a patient who contracted hepatitis during an epidemic of non-A, non-B hepatitis in Japan", Journal of General Virology, 1992, vol. 73, pp. 2725-2729.

Okamoto, H. et al. "Characterization of the genomic sequence of type V (or 3a) hepatitis C virus isolates and PCR primers for specifics detection", Journal of General Virology, 1993, vol. 74, pp. 2385-2390.

Seki, M. et al. "Effective production of hepatitis C virus core antigen having high purity in *Escherichia coli*", Journal of Biotechnology, 1995, vol. 38, pp. 229-241.

Kato, N. et al. Accession No. D12967 downloaded from Genbank VRL May 28, 1999.

Takeuchi, K. et al. Accession Nos. D00574, D90080, M57585 downloaded from Genbank VRL Feb. 2, 1999.

Hall, W. et al. Accession No. L19383 downloaded from Genbank VRL Aug. 11, 1994.

Ogata, N. et al. Accession No. M62381 downloaded from Genbank VRL Jun. 10, 1996.

Odeberg, J. et al. Accession No. U24616 downloaded from Genbank VRL Feb. 23, 1996.

Odeberg, J. et al. Accession No. U24607 downloaded from Genbank VRL Feb. 23, 1996.

Kato, N. Accession No. X60573 downloaded from Genbank VRL Apr. 5, 1992.

Kato, N. et al. Accession No. D43650 downloaded from Genbank VRL Nov. 10, 1997.

Hohne, M. et al. Accession No. S73387 downloaded from Genbank VRL Aug. 22, 2000.

Wang, Y. et al. Accession No. D10934 downloaded from Genbank VRL Feb. 3, 1999.

Okamoto, H. et al. Accession No. D31972 downloaded from Genbank VRL Feb. 7, 1999.

Greene, W. et al. Accession No. U14231 downladed from Genbank VRL Jan. 27, 1995.

Odeberg, J. et al. Accession No. U24602 downloaded from Genbank VRL Feb. 23, 1996.

Hall, W. et al. Accession No. L19380 downloaded from Genbank VRL Aug. 11, 1994.

Liu, K. et al. Accession No. M74888 downloaded from Genbank VRL Aug. 2, 1993.

Han, J. et al. Accession No. L12354 downloaded from Genbank VRL Jul. 27, 1994.

Scarselli, E. et al. Accession No. X79672 downloaded from Gebank VRL Jun. 28. 1995.

Kato, N. et al. Accession No. D12952 downloaded from Genbank VRl May 28, 1999.

Kato, N. et al. Accession No. D16566 downloaded from Genbank VRl Feb. 4, 1999.

Chen, P. et al. Accession No. M84754 downloaded from Genbank VRL Jul. 14, 1994.

Okamoto, H. et al. Accession No. D14853 downloaded from Genbank VRL Feb. 1, 2000.

Kato, N. et al. Accession No. S24080 downloaded from Genbank VRL May 29, 1998.

Sarashina, T. et al. Accession No. S35631 downloaded from Genbank VRL May 7, 1999.

Weiner, A. et al. Accession No. S62395 downloaded from Genbank VRL Aug. 25, 1993.

Yamaguchi, K. et al. Accession No. S70291 downloaded from Genbank VRL Sep. 23, 1994.

Tokita, H. et al. Accession Nos. D88472, D17503 downloaded from Genbank VRL Feb. 7, 1999.

Abe, K. et al. Accession No. D10687 downloaded from Genbank VRL Feb.1, 2000.

Kato, N. et al. Accession No. D43651 downloaded from Genbank VRL Nov. 10, 1997.

Okamoto, H. et al. Accession No. D14305 downloaded from Genbank VRL Feb. 1, 2000.

Kato, N. Accession No. X60590 downloaded from Genbank VRL Apr. 5, 1992.

Seki, M. et al. Accession No. D30613 downloaded from Genbank VRL Feb. 7, 1999.

Weiner, A. Accession No. X53131 downloaded from Genbank VRL Aug. 5, 1995.

Odeberg, J. et al. Accession No. U24619 downloaded from Genbank VRL Feb. 23, 1996.

Ogata, N. et al. Accession No. M62382 downloaded from Genbank VRL Jun. 10, 1996.

Tokita, H. et al. Accession Nos. D88474, D17505 downloaded from Genbank VRL Feb. 7, 1999.

Scarselli, E. et al. Accession No. X79669 downloaded from Genbank VRL Jul. 23, 1997.

Jones, R. et al. Accession No. A48766 downloaded from Munich Information Center for Protein Sequences (MIPS) May 19, 1995.

Okamoto, R. et al. Accession No. PQ0835 downloaded from MIPS Jul. 14, 1994.

Higashi, R. et al. Accession No. D48776 downloaded from MIPS Apr. 7, 1994.

Higashi, R. et al. Accession No. C48776 downloaded from MIPS Apr. 7, 1994.

Kato, N. et al. Accession No. PC1193 downloaded from MIPS Sep. 30, 1993.

Peter Jackson, et al. Reactivity of Synthetic Peptides Representing Selected Sections of Hepatitis C Virus Core and Envelope Proteins With a Panel of Hepatitis C Virus-Seropositive Human Plasma. Journal of Medical Virology 51:67-79 (1997); XP-002120165.

Andree Zibert, et al. Epitope Mapping of Antibodies Directed against Hypervariable Region 1 in Acute Self-Limiting and Chronic Infections due to Hepatitis C Virus. Journal of Virology, May 1997, p. 4123-4127; XP-002120167.

Giulia Puntoriero, et al., Towards a solution for hepatitis C virus hypervariability; mimotopes of the hypervariable region 1 can induce antibodies cross-reacting witha large number of viral variants. The EMBO Journal vol. 17, No. 13 pp. 3521-3533, 1998; XP-002120168.

Nobuyuki Kato, et al., Susceptibility of Human T-Lymphotropic Virus Type 1 Infected Cell Line MT-2 to Hepatitis C Virus Infection. Biochemical and Biophysical Research Communications. vol. 206, No. 3, Jan. 26, 1995, pp. 863-869; XP-002120166.

Rosalba Tafi, et al. Identification of HCV Core Mimotopes: Improved Methods for the Selection and Use of Disease-Related Phage-Displayed Peptides; Biol. Chem., vol. 378, pp. 495-502, Jun. 1997; XP-002120164.

Abstract: Oba Yoichi, Antigenic Peptide Derived From Hepatitis C Virus and Antibody Testing Agent Using The Same; Publication No. 11124398; Publication Date: Nov. 5, 1999; Applicant: Japan Energy Corp. Application No.: 09290165; Application Date: Oct. 22, 1997.

A

|  | R9 | H1 | M63 | M122 |
|---|---|---|---|---|
| C7 | 0.14 | 0.13 | 0.00 | 0.22 |
| C8 | 1.67 | 1.83 | 1.05 | 0.38 |
| C9 | 2.30 | 0.65 | 0.21 | 0.11 |
| C10 | 1.23 | 1.30 | 0.71 | 0.64 |
| C12 | 0.16 | 1.26 | 0.20 | 1.09 |
| C13 | 0.90 | 2.06 | 0.57 | 0.19 |
| C14 | 0.47 | 0.63 | 1.09 | 2.27 |
| C17 | 1.48 | 1.35 | 1.00 | 0.00 |
| C23 | 0.00 | 0.88 | 2.65 | 0.00 |
| C27 | 0.00 | 0.00 | 0.00 | 3.17 |
| C28 | 2.98 | 0.15 | 0.00 | 1.98 |
| C29 | 0.00 | 0.00 | 2.85 | 1.17 |
| C30 | 0.18 | 0.00 | 2.85 | 1.17 |
| C40 | 3.17 | 1.84 | 0.20 | 2.96 |
| C48 | 3.07 | 2.58 | 0.00 | 2.56 |
| C49 | 0.12 | 0.00 | 0.00 | 0.00 |
| C50 | 0.00 | 0.00 | 0.12 | 0.00 |
| C56 | 0.33 | 0.12 | 0.00 | 0.00 |
| C58 | 2.85 | 1.42 | 0.38 | 0.35 |
| C62 | 0.00 | 0.00 | 0.13 | 0.00 |
| frequency | 75% | 70% | 70% | 70% | total: 100% |

B

|  | R9 | H1 | M63 | M122 |
|---|---|---|---|---|
| 1V | 0.49 | 2.51 | 0.00 | 0.20 |
| 2V | 0.00 | 0.19 | 0.11 | 0.00 |
| 3V | 0.65 | 1.90 | 1.73 | 0.62 |
| 4V | 0.25 | 0.00 | 0.00 | 0.29 |
| 5V | 1.75 | 2.47 | 0.31 | 0.00 |
| 7V | 0.60 | 1.09 | 1.16 | 0.88 |
| 8V | 0.30 | 0.88 | 0.00 | 0.00 |
| 9V | 0.00 | 0.59 | 0.00 | 0.00 |
| 10V | 0.58 | 0.11 | 1.98 | 0.00 |
| 1P | 0.00 | 0.00 | 0.00 | 0.33 |
| 5P | 0.24 | 0.28 | 0.44 | 0.00 |
| 6P | 0.47 | 1.54 | 0.27 | 0.31 |
| 7P | 0.78 | 1.33 | 1.00 | 0.00 |
| 8P | 0.68 | 0.57 | 0.14 | 0.38 |
| 10P | 1.20 | 1.12 | 0.81 | 0.88 |
| 11P | 0.32 | 0.44 | 0.00 | 0.22 |
| 12P | 1.50 | 1.08 | 0.84 | 0.90 |
| 13P | 0.49 | 0.00 | 0.00 | 0.31 |
| frequency | 83% | 83% | 61% | 61% | total: 100% |

C

|  | R9 | H1 | M63 | M122 |
|---|---|---|---|---|
| X1 | 0.00 | 0.00 | 0.00 | 0.00 |
| X2 | 1.37 | 0.17 | 0.21 | 0.68 |
| X3 | 0.15 | 0.56 | 0.38 | 0.00 |
| X4 | 0.00 | 0.00 | 0.00 | 0.00 |
| X5 | 0.00 | 0.14 | 0.00 | 0.00 |
| X6 | 0.25 | 0.00 | 0.00 | 0.31 |
| X7 | 0.66 | 0.83 | 0.60 | 0.34 |
| X8 | 1.04 | 1.31 | 0.98 | 0.45 |
| X9 | 0.96 | 0.21 | 0.00 | 0.00 |
| X10 | 0.00 | 0.00 | 0.00 | 0.00 |
| X11 | 0.74 | 0.33 | 0.11 | 0.91 |
| X12 | 0.00 | 0.00 | 0.00 | 0.00 |
| X13 | 2.30 | 0.18 | 0.54 | 0.00 |
| X14 | 1.20 | 0.00 | 0.00 | 0.00 |
| X15 | 2.38 | 0.00 | 0.00 | 1.60 |
| X16 | 1.92 | 2.30 | 1.86 | 2.19 |
| X17 | 0.00 | 0.00 | 0.00 | 0.00 |
| X18 | 0.00 | 0.00 | 0.00 | 0.00 |
| X19 | 0.00 | 0.00 | 0.00 | 0.00 |
| X20 | 0.47 | 0.33 | 0.26 | 0.00 |
| X21 | 0.00 | 0.86 | 1.45 | 1.96 |
| X22 | 0.37 | 0.44 | 0.44 | 0.12 |
| X23 | 0.61 | 0.60 | 0.10 | 0.00 |
| X24 | 0.00 | 0.00 | 0.80 | 0.73 |
| X25 | 0.00 | 0.00 | 0.00 | 0.47 |
| X26 | 0.00 | 0.00 | 0.00 | 0.00 |
| X27 | 0.00 | 0.00 | 0.00 | 0.00 |
| 1NV | 0.00 | 1.50 | 0.22 | 0.00 |
| 2NV | 0.00 | 0.40 | 0.23 | 0.00 |
| 3NV | 0.10 | 0.11 | 0.00 | 0.00 |
| 4NV | 0.00 | 0.00 | 0.00 | 0.00 |
| 5NV | 0.00 | 0.00 | 0.00 | 0.00 |
| 6NV | 0.00 | 0.00 | 0.00 | 0.00 |
| 11NV | 0.10 | 0.00 | 0.00 | 0.53 |
| 12NV | 0.00 | 0.00 | 0.41 | 0.00 |
| 13NV | 0.00 | 0.00 | 0.00 | 0.00 |
| 15NV | 0.12 | 0.00 | 0.00 | 0.19 |
| 16NV | 0.52 | 0.84 | 0.36 | 0.60 |
| 17NV | 0.64 | 0.52 | 0.41 | 1.14 |
| 3P | 0.00 | 0.00 | 0.00 | 0.00 |
| 4P | 0.00 | 0.00 | 0.00 | 0.00 |
| frequency | 46% | 44% | 41% | 37% | total: 63% |

| mimotope | sequence |
|---|---|
| N5 | TTTTTGGVQGHTTRGLVRLFSLGSKQN |
| R6 | TTTTTGGQVGHQTSGLTGLFSPGAQQN |
| D6 | QTTTTGGQVSHATHGLTGLFSLGPQQK |
| R9 | QTTVVGGSQSHTVRGLTSLFSPGASQN |
| H1 | QTHTTGGVVGHATSGLTSLFSPGPSQK |
| G31 | TTHTVGGSVARQVHSLTGLFSPGPQQK |
| M122 | QTTTTGGSASHAVSSLTGLFSPGSKQN |
| B14 | QTTVTG-QASHTTSSLTGLFSPGASQK |
| F78 | QTHTTGGQAGHQAHSLTGLFSPGAKQN |

B

SEQUENCE LISTING

<160> NUMBER OF SEQ ID NOS: 199

<210> SEQ ID NO 1
<211> LENGTH: 27
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Gln or Thr
<221> NAME/KEY: SITE
<222> LOCATION: (3)
<223> OTHER INFORMATION: Xaa is His, Thr or Arg
<221> NAME/KEY: SITE
<222> LOCATION: (4)
<223> OTHER INFORMATION: Xaa is Val or Thr
<221> NAME/KEY: SITE
<222> LOCATION: (5)
<223> OTHER INFORMATION: Xaa is Thr or Val
<221> NAME/KEY: SITE
<222> LOCATION: (8)
<223> OTHER INFORMATION: Xaa is Ser, Val or Gln
<221> NAME/KEY: SITE
<222> LOCATION: (9)
<223> OTHER INFORMATION: Xaa is Ala, Gln or Val
<221> NAME/KEY: SITE
<222> LOCATION: (10)
<223> OTHER INFORMATION: Xaa is Ala, Gly or Ser
<221> NAME/KEY: SITE
<222> LOCATION: (11)
<223> OTHER INFORMATION: Xaa is Arg or His
<221> NAME/KEY: SITE
<222> LOCATION: (12)
<223> OTHER INFORMATION: Xaa is Thr, Ala or Gln
<221> NAME/KEY: SITE
<222> LOCATION: (13)
<223> OTHER INFORMATION: Xaa is Thr, Ala or Val
<221> NAME/KEY: SITE
<222> LOCATION: (14)
<223> OTHER INFORMATION: Xaa is Ser, His or Arg
<221> NAME/KEY: SITE
<222> LOCATION: (15)
<223> OTHER INFORMATION: Xaa is Gly, Ser or Arg
<221> NAME/KEY: SITE
<222> LOCATION: (17)
<223> OTHER INFORMATION: Xaa is Thr or Val
<221> NAME/KEY: SITE
<222> LOCATION: (18)
<223> OTHER INFORMATION: Xaa is Ser, Gly or Arg
<221> NAME/KEY: SITE
<222> LOCATION: (21)
<223> OTHER INFORMATION: Xaa is Ser or Arg
<221> NAME/KEY: SITE
<222> LOCATION: (22)
<223> OTHER INFORMATION: Xaa is Pro, Leu, Ser or Gln
<221> NAME/KEY: SITE
<222> LOCATION: (24)
<223> OTHER INFORMATION: Xaa is Ala, Pro or Ser

```
<221> NAME/KEY: SITE
<222> LOCATION: (25)
<223> OTHER INFORMATION: Xaa is Ser, Lys or Gln
<221> NAME/KEY: SITE
<222> LOCATION: (27)
<223> OTHER INFORMATION: Xaa is Asn or Lys
<223> OTHER INFORMATION: Description of Artificial Sequence: Synthetic
      peptide

<400> SEQUENCE: 1

Xaa Thr Xaa Xaa Xaa Gly Gly Xaa Xaa Xaa Xaa Xaa Xaa Xaa Xaa Leu
 1               5                  10                  15

Xaa Xaa Leu Phe Xaa Xaa Gly Xaa Xaa Gln Xaa
            20                  25

<210> SEQ ID NO 2
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gln Thr His Thr Val Gly Gly Val Gln Gly Arg Gln Ala His Ser Leu
 1               5                  10                  15

Thr Ser Leu Phe Ser Pro Gly Ala Ser Gln Asn
            20                  25

<210> SEQ ID NO 3
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Thr Thr Thr Thr Gly Gly Gln Val Ser His Ala Thr His Gly Leu
 1               5                  10                  15

Thr Gly Leu Phe Ser Leu Gly Pro Gln Gln Lys
            20                  25

<210> SEQ ID NO 4
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Thr His Thr Thr Gly Gly Ser Ala Ser His Gln Ala Ser Gly Leu
 1               5                  10                  15

Thr Arg Leu Phe Ser Gln Gly Pro Ser Gln Asn
            20                  25

<210> SEQ ID NO 5
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5
```

-continued

```
Gln Thr His Val Val Gly Gly Gln Gln Gly Arg Gln Val Ser Ser Leu
 1               5                  10                  15

Val Ser Leu Phe Ser Pro Gly Ala Ser Gln Lys
            20                  25

<210> SEQ ID NO 6
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Thr Thr His Thr Val Gly Gly Ser Val Ala Arg Gln Val His Ser Leu
 1               5                  10                  15

Thr Gly Leu Phe Ser Pro Gly Pro Gln Gln Lys
            20                  25

<210> SEQ ID NO 7
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gln Thr His Thr Val Gly Gly Ser Gln Ala His Ala Ala His Ser Leu
 1               5                  10                  15

Thr Arg Leu Phe Ser Pro Gly Ser Ser Gln Asn
            20                  25

<210> SEQ ID NO 8
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Thr Thr Val Val Gly Gly Ser Gln Ala Arg Ala Ala His Gly Leu
 1               5                  10                  15

Val Ser Leu Phe Ser Leu Gly Ser Lys Gln Asn
            20                  25

<210> SEQ ID NO 9
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Thr His Val Val Gly Gly Val Gln Gly Arg Gln Thr Ser Gly Leu
 1               5                  10                  15

Val Gly Leu Phe Ser Pro Gly Ser Lys Gln Asn
            20                  25

<210> SEQ ID NO 10
<211> LENGTH: 27
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 10

Gln Thr Thr Val Val Gly Gly Ser Gln Ser His Thr Val Arg Gly Leu
 1               5                  10                  15

Thr Ser Leu Phe Ser Pro Gly Ala Ser Gln Asn
            20                  25

<210> SEQ ID NO 11
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Thr Thr Thr Thr Thr Gly Gly Gln Ala Gly His Gln Ala His Ser Leu
 1               5                  10                  15

Thr Ser Leu Phe Ser Pro Gly Ala Ser Gln Lys
            20                  25

<210> SEQ ID NO 12
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Thr His Val Val Gly Gly Val Gln Ser His Gln Thr Ser Gly Leu
 1               5                  10                  15

Thr Ser Leu Phe Ser Pro Gly Ala Ser Gln Lys
            20                  25

<210> SEQ ID NO 13
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gln Thr His Thr Thr Gly Gly Val Gln Gly His Gln Thr Ser Arg Leu
 1               5                  10                  15

Thr Ser Leu Phe Ser Pro Gly Pro Ser Gln Asn
            20                  25

<210> SEQ ID NO 14
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Thr Thr Thr Val Val Gly Gly Gln Ala Ala His Gln Thr His Ser Leu
 1               5                  10                  15

Thr Ser Leu Phe Ser Pro Gly Ala Lys Gln Asn
            20                  25
```

<210> SEQ ID NO 15
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Thr Thr Thr Thr Thr Gly Gly Gln Gln Ser His Thr Val His Gly Leu
 1               5                  10                  15

Val Gly Leu Phe Ser Pro Gly Ser Lys Gln Asn
            20                  25

<210> SEQ ID NO 16
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gln Thr His Thr Val Gly Gly Val Gln Ala His Thr Val Arg Gly Leu
 1               5                  10                  15

Thr Ser Leu Phe Ser Pro Gly Ser Ser Gln Asn
            20                  25

<210> SEQ ID NO 17
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gln Thr His Thr Thr Gly Gly Gln Ala Gly His Thr Ala Ser Ser Leu
 1               5                  10                  15

Thr Gly Leu Phe Ser Pro Gly Ala Lys Gln Asn
            20                  25

<210> SEQ ID NO 18
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Thr Thr Thr Val Gly Gly Val Ala Ser His Gln Ala His Ser Leu
 1               5                  10                  15

Thr Gly Leu Phe Ser Pro Gly Ala Lys Gln Lys
            20                  25

<210> SEQ ID NO 19
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

```
Gln Thr His Thr Thr Gly Gly Gln Ala Gly His Gln Ala His Ser Leu
  1               5                  10                  15

Thr Gly Leu Phe Ser Pro Gly Ala Lys Gln Asn
             20                  25
```

<210> SEQ ID NO 20
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

```
Gln Thr His Thr Thr Gly Gly Val Val Gly His Ala Thr Ser Gly Leu
  1               5                  10                  15

Thr Ser Leu Phe Ser Pro Gly Pro Ser Gln Lys
             20                  25
```

<210> SEQ ID NO 21
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

```
Thr Thr Thr Thr Val Gly Gly Gln Ala Ser His Gln Thr Ser Ser Leu
  1               5                  10                  15

Thr Gly Leu Phe Ser Pro Gly Ser Lys Gln Asn
             20                  25
```

<210> SEQ ID NO 22
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

```
Gln Thr Thr Thr Thr Gly Gly Val Ala Ser His Ala Ala His Arg Leu
  1               5                  10                  15

Thr Ser Leu Phe Ser Pro Gly Pro Gln Gln Lys
             20                  25
```

<210> SEQ ID NO 23
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

```
Gln Thr Thr Thr Thr Gly Gly Ser Ala Ser His Ala Val Ser Ser Leu
  1               5                  10                  15

Thr Gly Leu Phe Ser Pro Gly Ser Lys Gln Asn
             20                  25
```

<210> SEQ ID NO 24
<211> LENGTH: 27
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 24

Gln Thr Thr Val Val Gly Gly Ser Ala Gly His Thr Ala Ser Ser Leu
 1               5                  10                  15

Val Gly Leu Phe Ser Pro Gly Ser Lys Gln Asn
            20                  25

<210> SEQ ID NO 25
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Thr Thr Thr Thr Val Gly Gly Gln Ala Ser His Thr Thr Ser Ser Leu
 1               5                  10                  15

Thr Gly Leu Phe Ser Pro Gly Ser Gln Gln Asn
            20                  25

<210> SEQ ID NO 26
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gln Thr His Thr Thr Gly Gly Gln Ala Ser His Gln Val Ser Ser Leu
 1               5                  10                  15

Val Ser Leu Phe Ser Pro Gly Ala Lys Gln Lys
            20                  25

<210> SEQ ID NO 27
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Thr Thr Thr Thr Thr Gly Gly Gln Val Gly His Gln Thr Ser Gly Leu
 1               5                  10                  15

Thr Gly Leu Phe Ser Pro Gly Ala Gln Gln Asn
            20                  25

<210> SEQ ID NO 28
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Thr Thr His Val Val Gly Gly Ser Ala Ser His Ala Val Arg Gly Leu
 1               5                  10                  15

Thr Ser Leu Phe Ser Pro Gly Ser Ser Gln Asn
```

```
<210> SEQ ID NO 29
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gln Thr Thr Val Thr Gly Gln Ala Ser His Thr Thr Ser Ser Leu Thr
 1               5                  10                  15

Gly Leu Phe Ser Pro Gly Ala Ser Gln Lys
            20                  25

<210> SEQ ID NO 30
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ala Thr His Ala Thr Gly Gly Gln Ala Ala His Ser Thr His Ser Leu
 1               5                  10                  15

Thr Ser Leu Phe Ser Pro Gly Ala Ser Gln Lys
            20                  25

<210> SEQ ID NO 31
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gln Thr His Val Thr Gly Gly Ser Ala Ala His Gln Thr Gly Gly Leu
 1               5                  10                  15

Thr Gly Leu Phe Ser Pro Gly Pro Lys Gln Asn
            20                  25

<210> SEQ ID NO 32
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln Thr Thr Val Val Gly Gly Gln Ala Ser His Val Ser Arg Leu Thr
 1               5                  10                  15

Gly Leu Phe Ser Pro Gly Ser Ser Gln Lys
            20                  25

<210> SEQ ID NO 33
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 33

Gln Thr Thr Thr Ala Ala His Thr Thr Ser Gly Leu Thr Gly Leu Phe
 1               5                  10                  15

Ser Pro Gly Ala Lys Gln Asn
            20

<210> SEQ ID NO 34
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gln Thr His Val Thr Gly Val Ala Gly Arg Gln Thr Ser Gly Leu Val
 1               5                  10                  15

Ser Leu Phe Ser Pro Gly Ser Ser Gln Asn
            20                  25

<210> SEQ ID NO 35
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gln Gly Gly Val Gln Gly His Thr Thr Ser Leu Val Gly Leu Phe
 1               5                  10                  15

Ser Pro Gly Ser Gln Gln Asn
            20

<210> SEQ ID NO 36
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Thr Thr His Thr Gly Gly Gln Gln Ala His Thr Thr Ser Arg Leu Val
 1               5                  10                  15

Ser Leu Phe Ser Pro Gly Ala Ser Gln Lys
            20                  25

<210> SEQ ID NO 37
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Thr Thr Thr Thr Val Gly Gly Gln Ala Ser His Thr Thr Ser Ser Leu
 1               5                  10                  15

Thr Gly Leu Phe Ser Pro Gly Ala Ser Gln Lys
            20                  25

<210> SEQ ID NO 38
<211> LENGTH: 27
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gln Thr His Thr Thr Gly Gly Val Val Ser His Gln Thr Arg Ser Leu
 1               5                  10                  15

Val Gly Leu Phe Ser Pro Gly Pro Gln Gln Asn
            20                  25

<210> SEQ ID NO 39
<211> LENGTH: 27
<212> TYPE: PRT
<213> ORGANISM: Artificial Sequence
<220> FEATURE:
<221> NAME/KEY: SITE
<222> LOCATION: (3)
<223> OTHER INFORMATION: Xaa is His or Thr
<221> NAME/KEY: SITE
<222> LOCATION: (11)
<223> OTHER INFORMATION: Xaa is His or Arg
<221> NAME/KEY: SITE
<222> LOCATION: (18)
<223> OTHER INFORMATION: Xaa is Gly, Ser or Arg
<221> NAME/KEY: SITE
<222> LOCATION: (22)
<223> OTHER INFORMATION: Xaa is Pro, Leu or Gln
<221> NAME/KEY: SITE
<222> LOCATION: (24)
<223> OTHER INFORMATION: Xaa is Ala, Ser or Pro
<223> OTHER INFORMATION: Description of Artificial Sequence: Synthetic
      peptide

<400> SEQUENCE: 39

Gln Thr Xaa Thr Val Gly Gly Gln Ala Ser Xaa Gln Ala Ser Ser Leu
 1               5                  10                  15

Thr Xaa Leu Phe Ser Xaa Gly Xaa Lys Gln Asn
            20                  25

<210> SEQ ID NO 40
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gln Thr His Thr Val Gly Gly Gln Ala Ser His Gln Ala Ser Ser Leu
 1               5                  10                  15

Thr Ser Leu Phe Ser Pro Gly Ala Lys Gln Asn
            20                  25

<210> SEQ ID NO 41
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gln Thr His Thr Val Gly Gly Gln Ala Ser His Gln Ala Ser Ser Leu
 1               5                  10                  15

Thr Ser Leu Phe Ser Pro Gly Ser Lys Gln Asn
            20                  25
```

<210> SEQ ID NO 42
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gln Thr His Thr Val Gly Gly Gln Ala Ser His Gln Ala Ser Ser Leu
 1               5                  10                  15

Thr Ser Leu Phe Ser Pro Gly Pro Lys Gln Asn
            20                  25

<210> SEQ ID NO 43
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gln Thr His Thr Val Gly Gly Gln Ala Ser His Gln Ala Ser Ser Leu
 1               5                  10                  15

Thr Ser Leu Phe Ser Leu Gly Ala Lys Gln Asn
            20                  25

<210> SEQ ID NO 44
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Thr His Thr Val Gly Gly Gln Ala Ser His Gln Ala Ser Ser Leu
 1               5                  10                  15

Thr Ser Leu Phe Ser Leu Gly Ser Lys Gln Asn
            20                  25

<210> SEQ ID NO 45
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gln Thr His Thr Val Gly Gly Gln Ala Ser His Gln Ala Ser Ser Leu
 1               5                  10                  15

Thr Ser Leu Phe Ser Leu Gly Pro Lys Gln Asn
            20                  25

<210> SEQ ID NO 46
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gln Thr His Thr Val Gly Gly Gln Ala Ser His Gln Ala Ser Ser Leu
1               5                   10                  15

Thr Ser Leu Phe Ser Gln Gly Ala Lys Gln Asn
            20                  25

<210> SEQ ID NO 47
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gln Thr His Thr Val Gly Gly Gln Ala Ser His Gln Ala Ser Ser Leu
1               5                   10                  15

Thr Ser Leu Phe Ser Gln Gly Ser Lys Gln Asn
            20                  25

<210> SEQ ID NO 48
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gln Thr His Thr Val Gly Gly Gln Ala Ser His Gln Ala Ser Ser Leu
1               5                   10                  15

Thr Ser Leu Phe Ser Gln Gly Pro Lys Gln Asn
            20                  25

<210> SEQ ID NO 49
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gln Thr His Thr Val Gly Gly Gln Ala Ser His Gln Ala Ser Ser Leu
1               5                   10                  15

Thr Gly Leu Phe Ser Pro Gly Ala Lys Gln Asn
            20                  25

<210> SEQ ID NO 50
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gln Thr His Thr Val Gly Gly Gln Ala Ser His Gln Ala Ser Ser Leu
1               5                   10                  15

Thr Gly Leu Phe Ser Pro Gly Ser Lys Gln Asn
            20                  25

<210> SEQ ID NO 51
<211> LENGTH: 27
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 51

Gln Thr His Thr Val Gly Gly Gln Ala Ser His Gln Ala Ser Ser Leu
 1               5                  10                  15

Thr Gly Leu Phe Ser Pro Gly Pro Lys Gln Asn
            20                  25

<210> SEQ ID NO 52
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gln Thr His Thr Val Gly Gly Gln Ala Ser His Gln Ala Ser Ser Leu
 1               5                  10                  15

Thr Gly Leu Phe Ser Leu Gly Ala Lys Gln Asn
            20                  25

<210> SEQ ID NO 53
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gln Thr His Thr Val Gly Gly Gln Ala Ser His Gln Ala Ser Ser Leu
 1               5                  10                  15

Thr Gly Leu Phe Ser Leu Gly Ser Lys Gln Asn
            20                  25

<210> SEQ ID NO 54
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gln Thr His Thr Val Gly Gly Gln Ala Ser His Gln Ala Ser Ser Leu
 1               5                  10                  15

Thr Gly Leu Phe Ser Leu Gly Pro Lys Gln Asn
            20                  25

<210> SEQ ID NO 55
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gln Thr His Thr Val Gly Gly Gln Ala Ser His Gln Ala Ser Ser Leu
 1               5                  10                  15

Thr Gly Leu Phe Ser Gln Gly Ala Lys Gln Asn
```

20                  25

<210> SEQ ID NO 56
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gln Thr His Thr Val Gly Gly Gln Ala Ser His Gln Ala Ser Ser Leu
 1               5                  10                  15

Thr Gly Leu Phe Ser Gln Gly Ser Lys Gln Asn
            20                  25

<210> SEQ ID NO 57
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gln Thr His Thr Val Gly Gly Gln Ala Ser His Gln Ala Ser Ser Leu
 1               5                  10                  15

Thr Gly Leu Phe Ser Gln Gly Pro Lys Gln Asn
            20                  25

<210> SEQ ID NO 58
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gln Thr His Thr Val Gly Gly Gln Ala Ser His Gln Ala Ser Ser Leu
 1               5                  10                  15

Thr Arg Leu Phe Ser Pro Gly Ala Lys Gln Asn
            20                  25

<210> SEQ ID NO 59
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gln Thr His Thr Val Gly Gly Gln Ala Ser His Gln Ala Ser Ser Leu
 1               5                  10                  15

Thr Arg Leu Phe Ser Pro Gly Ser Lys Gln Asn
            20                  25

<210> SEQ ID NO 60
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 60

Gln Thr His Thr Val Gly Gly Gln Ala Ser His Gln Ala Ser Ser Leu
 1               5                  10                  15

Thr Arg Leu Phe Ser Pro Gly Pro Lys Gln Asn
             20                  25

<210> SEQ ID NO 61
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gln Thr His Thr Val Gly Gly Gln Ala Ser His Gln Ala Ser Ser Leu
 1               5                  10                  15

Thr Arg Leu Phe Ser Leu Gly Ala Lys Gln Asn
             20                  25

<210> SEQ ID NO 62
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gln Thr His Thr Val Gly Gly Gln Ala Ser His Gln Ala Ser Ser Leu
 1               5                  10                  15

Thr Arg Leu Phe Ser Leu Gly Ser Lys Gln Asn
             20                  25

<210> SEQ ID NO 63
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gln Thr His Thr Val Gly Gly Gln Ala Ser His Gln Ala Ser Ser Leu
 1               5                  10                  15

Thr Arg Leu Phe Ser Leu Gly Pro Lys Gln Asn
             20                  25

<210> SEQ ID NO 64
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gln Thr His Thr Val Gly Gly Gln Ala Ser His Gln Ala Ser Ser Leu
 1               5                  10                  15

Thr Arg Leu Phe Ser Gln Gly Ala Lys Gln Asn
             20                  25

<210> SEQ ID NO 65
<211> LENGTH: 27
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gln Thr His Thr Val Gly Gly Gln Ala Ser His Gln Ala Ser Ser Leu
 1               5                  10                  15

Thr Arg Leu Phe Ser Gln Gly Ser Lys Gln Asn
            20                  25

<210> SEQ ID NO 66
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gln Thr His Thr Val Gly Gly Gln Ala Ser His Gln Ala Ser Ser Leu
 1               5                  10                  15

Thr Arg Leu Phe Ser Gln Gly Pro Lys Gln Asn
            20                  25

<210> SEQ ID NO 67
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gln Thr His Thr Val Gly Gly Gln Ala Ser Arg Gln Ala Ser Ser Leu
 1               5                  10                  15

Thr Ser Leu Phe Ser Pro Gly Ala Lys Gln Asn
            20                  25

<210> SEQ ID NO 68
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gln Thr His Thr Val Gly Gly Gln Ala Ser Arg Gln Ala Ser Ser Leu
 1               5                  10                  15

Thr Ser Leu Phe Ser Pro Gly Ser Lys Gln Asn
            20                  25

<210> SEQ ID NO 69
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gln Thr His Thr Val Gly Gly Gln Ala Ser Arg Gln Ala Ser Ser Leu
 1               5                  10                  15
```

Thr Ser Leu Phe Ser Pro Gly Pro Lys Gln Asn
            20                  25

<210> SEQ ID NO 70
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gln Thr His Thr Val Gly Gly Gln Ala Ser Arg Gln Ala Ser Ser Leu
 1               5                  10                  15

Thr Ser Leu Phe Ser Leu Gly Ala Lys Gln Asn
            20                  25

<210> SEQ ID NO 71
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gln Thr His Thr Val Gly Gly Gln Ala Ser Arg Gln Ala Ser Ser Leu
 1               5                  10                  15

Thr Ser Leu Phe Ser Leu Gly Ser Lys Gln Asn
            20                  25

<210> SEQ ID NO 72
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gln Thr His Thr Val Gly Gly Gln Ala Ser Arg Gln Ala Ser Ser Leu
 1               5                  10                  15

Thr Ser Leu Phe Ser Leu Gly Pro Lys Gln Asn
            20                  25

<210> SEQ ID NO 73
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gln Thr His Thr Val Gly Gly Gln Ala Ser Arg Gln Ala Ser Ser Leu
 1               5                  10                  15

Thr Ser Leu Phe Ser Gln Gly Ala Lys Gln Asn
            20                  25

<210> SEQ ID NO 74
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gln Thr His Thr Val Gly Gly Gln Ala Ser Arg Gln Ala Ser Ser Leu
1               5                   10                  15

Thr Ser Leu Phe Ser Gln Gly Ser Lys Gln Asn
            20                  25

<210> SEQ ID NO 75
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gln Thr His Thr Val Gly Gly Gln Ala Ser Arg Gln Ala Ser Ser Leu
1               5                   10                  15

Thr Ser Leu Phe Ser Gln Gly Pro Lys Gln Asn
            20                  25

<210> SEQ ID NO 76
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gln Thr His Thr Val Gly Gly Gln Ala Ser Arg Gln Ala Ser Ser Leu
1               5                   10                  15

Thr Gly Leu Phe Ser Pro Gly Ala Lys Gln Asn
            20                  25

<210> SEQ ID NO 77
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gln Thr His Thr Val Gly Gly Gln Ala Ser Arg Gln Ala Ser Ser Leu
1               5                   10                  15

Thr Gly Leu Phe Ser Pro Gly Ser Lys Gln Asn
            20                  25

<210> SEQ ID NO 78
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gln Thr His Thr Val Gly Gly Gln Ala Ser Arg Gln Ala Ser Ser Leu
1               5                   10                  15

Thr Gly Leu Phe Ser Pro Gly Pro Lys Gln Asn
            20                  25

<210> SEQ ID NO 79

```
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gln Thr His Thr Val Gly Gly Gln Ala Ser Arg Gln Ala Ser Ser Leu
 1               5                  10                  15

Thr Gly Leu Phe Ser Leu Gly Ala Lys Gln Asn
            20                  25

<210> SEQ ID NO 80
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gln Thr His Thr Val Gly Gly Gln Ala Ser Arg Gln Ala Ser Ser Leu
 1               5                  10                  15

Thr Gly Leu Phe Ser Leu Gly Ser Lys Gln Asn
            20                  25

<210> SEQ ID NO 81
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gln Thr His Thr Val Gly Gly Gln Ala Ser Arg Gln Ala Ser Ser Leu
 1               5                  10                  15

Thr Gly Leu Phe Ser Leu Gly Pro Lys Gln Asn
            20                  25

<210> SEQ ID NO 82
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gln Thr His Thr Val Gly Gly Gln Ala Ser Arg Gln Ala Ser Ser Leu
 1               5                  10                  15

Thr Gly Leu Phe Ser Gln Gly Ala Lys Gln Asn
            20                  25

<210> SEQ ID NO 83
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gln Thr His Thr Val Gly Gly Gln Ala Ser Arg Gln Ala Ser Ser Leu
 1               5                  10                  15
```

Thr Gly Leu Phe Ser Gln Gly Ser Lys Gln Asn
            20                  25

<210> SEQ ID NO 84
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gln Thr His Thr Val Gly Gly Gln Ala Ser Arg Gln Ala Ser Ser Leu
 1               5                  10                  15

Thr Gly Leu Phe Ser Gln Gly Pro Lys Gln Asn
            20                  25

<210> SEQ ID NO 85
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gln Thr His Thr Val Gly Gly Gln Ala Ser Arg Gln Ala Ser Ser Leu
 1               5                  10                  15

Thr Arg Leu Phe Ser Pro Gly Ala Lys Gln Asn
            20                  25

<210> SEQ ID NO 86
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gln Thr His Thr Val Gly Gly Gln Ala Ser Arg Gln Ala Ser Ser Leu
 1               5                  10                  15

Thr Arg Leu Phe Ser Pro Gly Ser Lys Gln Asn
            20                  25

<210> SEQ ID NO 87
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Gln Thr His Thr Val Gly Gly Gln Ala Ser Arg Gln Ala Ser Ser Leu
 1               5                  10                  15

Thr Arg Leu Phe Ser Pro Gly Pro Lys Gln Asn
            20                  25

<210> SEQ ID NO 88
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 88

Gln Thr His Thr Val Gly Gly Gln Ala Ser Arg Gln Ala Ser Ser Leu
1               5                   10                  15

Thr Arg Leu Phe Ser Leu Gly Ala Lys Gln Asn
            20                  25

<210> SEQ ID NO 89
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gln Thr His Thr Val Gly Gly Gln Ala Ser Arg Gln Ala Ser Ser Leu
1               5                   10                  15

Thr Arg Leu Phe Ser Leu Gly Ser Lys Gln Asn
            20                  25

<210> SEQ ID NO 90
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gln Thr His Thr Val Gly Gly Gln Ala Ser Arg Gln Ala Ser Ser Leu
1               5                   10                  15

Thr Arg Leu Phe Ser Leu Gly Pro Lys Gln Asn
            20                  25

<210> SEQ ID NO 91
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gln Thr His Thr Val Gly Gly Gln Ala Ser Arg Gln Ala Ser Ser Leu
1               5                   10                  15

Thr Arg Leu Phe Ser Gln Gly Ala Lys Gln Asn
            20                  25

<210> SEQ ID NO 92
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gln Thr His Thr Val Gly Gly Gln Ala Ser Arg Gln Ala Ser Ser Leu
1               5                   10                  15

Thr Arg Leu Phe Ser Gln Gly Ser Lys Gln Asn
            20                  25

-continued

```
<210> SEQ ID NO 93
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gln Thr His Thr Val Gly Gly Gln Ala Ser Arg Gln Ala Ser Ser Leu
 1               5                  10                  15

Thr Arg Leu Phe Ser Gln Gly Pro Lys Gln Asn
             20                  25

<210> SEQ ID NO 94
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gln Thr Thr Thr Val Gly Gly Gln Ala Ser His Gln Ala Ser Ser Leu
 1               5                  10                  15

Thr Ser Leu Phe Ser Pro Gly Ala Lys Gln Asn
             20                  25

<210> SEQ ID NO 95
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gln Thr Thr Thr Val Gly Gly Gln Ala Ser His Gln Ala Ser Ser Leu
 1               5                  10                  15

Thr Ser Leu Phe Ser Pro Gly Ser Lys Gln Asn
             20                  25

<210> SEQ ID NO 96
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gln Thr Thr Thr Val Gly Gly Gln Ala Ser His Gln Ala Ser Ser Leu
 1               5                  10                  15

Thr Ser Leu Phe Ser Pro Gly Pro Lys Gln Asn
             20                  25

<210> SEQ ID NO 97
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gln Thr Thr Thr Val Gly Gly Gln Ala Ser His Gln Ala Ser Ser Leu
```

-continued

```
            1               5                  10                 15
Thr Ser Leu Phe Ser Leu Gly Ala Lys Gln Asn
                20                  25

<210> SEQ ID NO 98
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gln Thr Thr Thr Val Gly Gly Gln Ala Ser His Gln Ala Ser Ser Leu
  1               5                  10                 15
Thr Ser Leu Phe Ser Leu Gly Ser Lys Gln Asn
                20                  25

<210> SEQ ID NO 99
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gln Thr Thr Thr Val Gly Gly Gln Ala Ser His Gln Ala Ser Ser Leu
  1               5                  10                 15
Thr Ser Leu Phe Ser Leu Gly Pro Lys Gln Asn
                20                  25

<210> SEQ ID NO 100
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gln Thr Thr Thr Val Gly Gly Gln Ala Ser His Gln Ala Ser Ser Leu
  1               5                  10                 15
Thr Ser Leu Phe Ser Gln Gly Ala Lys Gln Asn
                20                  25

<210> SEQ ID NO 101
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gln Thr Thr Thr Val Gly Gly Gln Ala Ser His Gln Ala Ser Ser Leu
  1               5                  10                 15
Thr Ser Leu Phe Ser Gln Gly Ser Lys Gln Asn
                20                  25

<210> SEQ ID NO 102
<211> LENGTH: 27
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 102

Gln Thr Thr Thr Val Gly Gly Gln Ala Ser His Gln Ala Ser Ser Leu
 1               5                  10                  15

Thr Ser Leu Phe Ser Gln Gly Pro Lys Gln Asn
            20                  25

<210> SEQ ID NO 103
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gln Thr Thr Thr Val Gly Gly Gln Ala Ser His Gln Ala Ser Ser Leu
 1               5                  10                  15

Thr Gly Leu Phe Ser Pro Gly Ala Lys Gln Asn
            20                  25

<210> SEQ ID NO 104
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gln Thr Thr Thr Val Gly Gly Gln Ala Ser His Gln Ala Ser Ser Leu
 1               5                  10                  15

Thr Gly Leu Phe Ser Pro Gly Ser Lys Gln Asn
            20                  25

<210> SEQ ID NO 105
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Gln Thr Thr Thr Val Gly Gly Gln Ala Ser His Gln Ala Ser Ser Leu
 1               5                  10                  15

Thr Gly Leu Phe Ser Pro Gly Pro Lys Gln Asn
            20                  25

<210> SEQ ID NO 106
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gln Thr Thr Thr Val Gly Gly Gln Ala Ser His Gln Ala Ser Ser Leu
 1               5                  10                  15

Thr Gly Leu Phe Ser Leu Gly Ala Lys Gln Asn
            20                  25

<210> SEQ ID NO 107
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gln Thr Thr Thr Val Gly Gly Gln Ala Ser His Gln Ala Ser Ser Leu
  1               5                  10                  15

Thr Gly Leu Phe Ser Leu Gly Ser Lys Gln Asn
            20                  25

<210> SEQ ID NO 108
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Gln Thr Thr Thr Val Gly Gly Gln Ala Ser His Gln Ala Ser Ser Leu
  1               5                  10                  15

Thr Gly Leu Phe Ser Leu Gly Pro Lys Gln Asn
            20                  25

<210> SEQ ID NO 109
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Gln Thr Thr Thr Val Gly Gly Gln Ala Ser His Gln Ala Ser Ser Leu
  1               5                  10                  15

Thr Gly Leu Phe Ser Gln Gly Ala Lys Gln Asn
            20                  25

<210> SEQ ID NO 110
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gln Thr Thr Thr Val Gly Gly Gln Ala Ser His Gln Ala Ser Ser Leu
  1               5                  10                  15

Thr Gly Leu Phe Ser Gln Gly Ser Lys Gln Asn
            20                  25

<210> SEQ ID NO 111
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

-continued

```
Gln Thr Thr Thr Val Gly Gly Gln Ala Ser His Gln Ala Ser Ser Leu
 1               5                  10                  15

Thr Gly Leu Phe Ser Gln Gly Pro Lys Gln Asn
            20                  25
```

<210> SEQ ID NO 112
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

```
Gln Thr Thr Thr Val Gly Gly Gln Ala Ser His Gln Ala Ser Ser Leu
 1               5                  10                  15

Thr Arg Leu Phe Ser Pro Gly Ala Lys Gln Asn
            20                  25
```

<210> SEQ ID NO 113
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

```
Gln Thr Thr Thr Val Gly Gly Gln Ala Ser His Gln Ala Ser Ser Leu
 1               5                  10                  15

Thr Arg Leu Phe Ser Pro Gly Ser Lys Gln Asn
            20                  25
```

<210> SEQ ID NO 114
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

```
Gln Thr Thr Thr Val Gly Gly Gln Ala Ser His Gln Ala Ser Ser Leu
 1               5                  10                  15

Thr Arg Leu Phe Ser Pro Gly Pro Lys Gln Asn
            20                  25
```

<210> SEQ ID NO 115
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

```
Gln Thr Thr Thr Val Gly Gly Gln Ala Ser His Gln Ala Ser Ser Leu
 1               5                  10                  15

Thr Arg Leu Phe Ser Leu Gly Ala Lys Gln Asn
            20                  25
```

<210> SEQ ID NO 116
<211> LENGTH: 27
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 116

Gln Thr Thr Thr Val Gly Gly Gln Ala Ser His Gln Ala Ser Ser Leu
 1               5                  10                  15

Thr Arg Leu Phe Ser Leu Gly Ser Lys Gln Asn
            20                  25

<210> SEQ ID NO 117
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Gln Thr Thr Thr Val Gly Gly Gln Ala Ser His Gln Ala Ser Ser Leu
 1               5                  10                  15

Thr Arg Leu Phe Ser Leu Gly Pro Lys Gln Asn
            20                  25

<210> SEQ ID NO 118
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Gln Thr Thr Thr Val Gly Gly Gln Ala Ser His Gln Ala Ser Ser Leu
 1               5                  10                  15

Thr Arg Leu Phe Ser Gln Gly Ala Lys Gln Asn
            20                  25

<210> SEQ ID NO 119
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Gln Thr Thr Thr Val Gly Gly Gln Ala Ser His Gln Ala Ser Ser Leu
 1               5                  10                  15

Thr Arg Leu Phe Ser Gln Gly Ser Lys Gln Asn
            20                  25

<210> SEQ ID NO 120
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Gln Thr Thr Thr Val Gly Gly Gln Ala Ser His Gln Ala Ser Ser Leu
 1               5                  10                  15

Thr Arg Leu Phe Ser Gln Gly Pro Lys Gln Asn
            20                  25
```

<210> SEQ ID NO 121
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 121

Gln Thr Thr Thr Val Gly Gly Gln Ala Ser Arg Gln Ala Ser Ser Leu
 1               5                  10                  15

Thr Ser Leu Phe Ser Pro Gly Ala Lys Gln Asn
            20                  25

<210> SEQ ID NO 122
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 122

Gln Thr Thr Thr Val Gly Gly Gln Ala Ser Arg Gln Ala Ser Ser Leu
 1               5                  10                  15

Thr Ser Leu Phe Ser Pro Gly Ser Lys Gln Asn
            20                  25

<210> SEQ ID NO 123
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 123

Gln Thr Thr Thr Val Gly Gly Gln Ala Ser Arg Gln Ala Ser Ser Leu
 1               5                  10                  15

Thr Ser Leu Phe Ser Pro Gly Pro Lys Gln Asn
            20                  25

<210> SEQ ID NO 124
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 124

Gln Thr Thr Thr Val Gly Gly Gln Ala Ser Arg Gln Ala Ser Ser Leu
 1               5                  10                  15

Thr Ser Leu Phe Ser Leu Gly Ala Lys Gln Asn
            20                  25

<210> SEQ ID NO 125
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 125

Gln Thr Thr Thr Val Gly Gly Gln Ala Ser Arg Gln Ala Ser Ser Leu
1               5                   10                  15

Thr Ser Leu Phe Ser Leu Gly Ser Lys Gln Asn
            20                  25

<210> SEQ ID NO 126
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Gln Thr Thr Thr Val Gly Gly Gln Ala Ser Arg Gln Ala Ser Ser Leu
1               5                   10                  15

Thr Ser Leu Phe Ser Leu Gly Pro Lys Gln Asn
            20                  25

<210> SEQ ID NO 127
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Gln Thr Thr Thr Val Gly Gly Gln Ala Ser Arg Gln Ala Ser Ser Leu
1               5                   10                  15

Thr Ser Leu Phe Ser Gln Gly Ala Lys Gln Asn
            20                  25

<210> SEQ ID NO 128
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Gln Thr Thr Thr Val Gly Gly Gln Ala Ser Arg Gln Ala Ser Ser Leu
1               5                   10                  15

Thr Ser Leu Phe Ser Gln Gly Ser Lys Gln Asn
            20                  25

<210> SEQ ID NO 129
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Gln Thr Thr Thr Val Gly Gly Gln Ala Ser Arg Gln Ala Ser Ser Leu
1               5                   10                  15

Thr Ser Leu Phe Ser Gln Gly Pro Lys Gln Asn
            20                  25

<210> SEQ ID NO 130
<211> LENGTH: 27
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 130

Gln Thr Thr Thr Val Gly Gly Gln Ala Ser Arg Gln Ala Ser Ser Leu
 1               5                  10                  15

Thr Gly Leu Phe Ser Pro Gly Ala Lys Gln Asn
            20                  25

<210> SEQ ID NO 131
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Gln Thr Thr Thr Val Gly Gly Gln Ala Ser Arg Gln Ala Ser Ser Leu
 1               5                  10                  15

Thr Gly Leu Phe Ser Pro Gly Ser Lys Gln Asn
            20                  25

<210> SEQ ID NO 132
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Gln Thr Thr Thr Val Gly Gly Gln Ala Ser Arg Gln Ala Ser Ser Leu
 1               5                  10                  15

Thr Gly Leu Phe Ser Pro Gly Pro Lys Gln Asn
            20                  25

<210> SEQ ID NO 133
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Gln Thr Thr Thr Val Gly Gly Gln Ala Ser Arg Gln Ala Ser Ser Leu
 1               5                  10                  15

Thr Gly Leu Phe Ser Leu Gly Ala Lys Gln Asn
            20                  25

<210> SEQ ID NO 134
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Gln Thr Thr Thr Val Gly Gly Gln Ala Ser Arg Gln Ala Ser Ser Leu
 1               5                  10                  15

Thr Gly Leu Phe Ser Leu Gly Ser Lys Gln Asn
```

20              25

<210> SEQ ID NO 135
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Gln Thr Thr Thr Val Gly Gly Gln Ala Ser Arg Gln Ala Ser Ser Leu
 1               5                  10                  15

Thr Gly Leu Phe Ser Leu Gly Pro Lys Gln Asn
            20                  25

<210> SEQ ID NO 136
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Gln Thr Thr Thr Val Gly Gly Gln Ala Ser Arg Gln Ala Ser Ser Leu
 1               5                  10                  15

Thr Gly Leu Phe Ser Gln Gly Ala Lys Gln Asn
            20                  25

<210> SEQ ID NO 137
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Gln Thr Thr Thr Val Gly Gly Gln Ala Ser Arg Gln Ala Ser Ser Leu
 1               5                  10                  15

Thr Gly Leu Phe Ser Gln Gly Ser Lys Gln Asn
            20                  25

<210> SEQ ID NO 138
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Gln Thr Thr Thr Val Gly Gly Gln Ala Ser Arg Gln Ala Ser Ser Leu
 1               5                  10                  15

Thr Gly Leu Phe Ser Gln Gly Pro Lys Gln Asn
            20                  25

<210> SEQ ID NO 139
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 139

Gln Thr Thr Thr Val Gly Gly Gln Ala Ser Arg Gln Ala Ser Ser Leu
 1               5                  10                  15

Thr Arg Leu Phe Ser Pro Gly Ala Lys Gln Asn
            20                  25

<210> SEQ ID NO 140
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Gln Thr Thr Thr Val Gly Gly Gln Ala Ser Arg Gln Ala Ser Ser Leu
 1               5                  10                  15

Thr Arg Leu Phe Ser Pro Gly Ser Lys Gln Asn
            20                  25

<210> SEQ ID NO 141
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Gln Thr Thr Thr Val Gly Gly Gln Ala Ser Arg Gln Ala Ser Ser Leu
 1               5                  10                  15

Thr Arg Leu Phe Ser Pro Gly Pro Lys Gln Asn
            20                  25

<210> SEQ ID NO 142
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Gln Thr Thr Thr Val Gly Gly Gln Ala Ser Arg Gln Ala Ser Ser Leu
 1               5                  10                  15

Thr Arg Leu Phe Ser Leu Gly Ala Lys Gln Asn
            20                  25

<210> SEQ ID NO 143
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Gln Thr Thr Thr Val Gly Gly Gln Ala Ser Arg Gln Ala Ser Ser Leu
 1               5                  10                  15

Thr Arg Leu Phe Ser Leu Gly Ser Lys Gln Asn
            20                  25

<210> SEQ ID NO 144
<211> LENGTH: 27
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Gln Thr Thr Thr Val Gly Gly Gln Ala Ser Arg Gln Ala Ser Ser Leu
 1               5                  10                  15

Thr Arg Leu Phe Ser Leu Gly Pro Lys Gln Asn
            20                  25

<210> SEQ ID NO 145
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Gln Thr Thr Thr Val Gly Gly Gln Ala Ser Arg Gln Ala Ser Ser Leu
 1               5                  10                  15

Thr Arg Leu Phe Ser Gln Gly Ala Lys Gln Asn
            20                  25

<210> SEQ ID NO 146
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Gln Thr Thr Thr Val Gly Gly Gln Ala Ser Arg Gln Ala Ser Ser Leu
 1               5                  10                  15

Thr Arg Leu Phe Ser Gln Gly Ser Lys Gln Asn
            20                  25

<210> SEQ ID NO 147
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Gln Thr Thr Thr Val Gly Gly Gln Ala Ser Arg Gln Ala Ser Ser Leu
 1               5                  10                  15

Thr Arg Leu Phe Ser Gln Gly Pro Lys Gln Asn
            20                  25

<210> SEQ ID NO 148
<211> LENGTH: 27
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Gln or Thr
<221> NAME/KEY: SITE
<222> LOCATION: (3)
<223> OTHER INFORMATION: Xaa is His or Thr
<221> NAME/KEY: SITE
<222> LOCATION: (4)
```

```
<223> OTHER INFORMATION: Xaa is Thr or Val
<223> OTHER INFORMATION: Description of Artificial Sequence: Synthetic
      peptide
<221> NAME/KEY: SITE
<222> LOCATION: (5)
<223> OTHER INFORMATION: Xaa is Val or Thr
<221> NAME/KEY: SITE
<222> LOCATION: (8)
<223> OTHER INFORMATION: Xaa is Gln, Ser or Val
<221> NAME/KEY: SITE
<222> LOCATION: (9)
<223> OTHER INFORMATION: Xaa is Ala, Gln or Val
<221> NAME/KEY: SITE
<222> LOCATION: (10)
<223> OTHER INFORMATION: Xaa is Ser, Gly or Ala
<221> NAME/KEY: SITE
<222> LOCATION: (12)
<223> OTHER INFORMATION: Xaa is Gln, Ala or Thr
<221> NAME/KEY: SITE
<222> LOCATION: (13)
<223> OTHER INFORMATION: Xaa is Ala, Thr or Val
<221> NAME/KEY: SITE
<222> LOCATION: (14)
<223> OTHER INFORMATION: Xaa is Ser, His or Arg
<221> NAME/KEY: SITE
<222> LOCATION: (15)
<223> OTHER INFORMATION: Xaa is Ser, Gly or Arg
<221> NAME/KEY: SITE
<222> LOCATION: (17)
<223> OTHER INFORMATION: Xaa is Thr or Val
<221> NAME/KEY: SITE
<222> LOCATION: (18)
<223> OTHER INFORMATION: Xaa is Ser or Gly
<221> NAME/KEY: SITE
<222> LOCATION: (24)
<223> OTHER INFORMATION: Xaa is Ala, Ser or Pro
<221> NAME/KEY: SITE
<222> LOCATION: (25)
<223> OTHER INFORMATION: Xaa is Lys, Ser or Gln
<221> NAME/KEY: SITE
<222> LOCATION: (27)
<223> OTHER INFORMATION: Xaa is Asn or Lys

<400> SEQUENCE: 148

Xaa Thr Xaa Xaa Xaa Gly Gly Xaa Xaa Xaa His Xaa Xaa Xaa Xaa Leu
 1               5                  10                  15

Xaa Xaa Leu Phe Ser Pro Gly Xaa Xaa Gln Xaa
            20                  25

<210> SEQ ID NO 149
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Thr Thr Thr Thr Thr Gly Gly Val Gln Gly His Thr Thr Arg Gly Leu
 1               5                  10                  15

Val Arg Leu Phe Ser Leu Gly Ser Lys Gln Asn
            20                  25

<210> SEQ ID NO 150
<211> LENGTH: 27
<212> TYPE: PRT
<213> ORGANISM: Hepatitis C virus

<400> SEQUENCE: 150

Gln Thr Arg Thr Val Gly Gly Gln Met Gly His Gly Val Arg Gly Leu
 1               5                  10                  15
```

Thr Ser Leu Phe Ser Ala Gly Ser Ala Arg Asn
            20                  25

<210> SEQ ID NO 151
<211> LENGTH: 27
<212> TYPE: PRT
<213> ORGANISM: Hepatitis C virus

<400> SEQUENCE: 151

Ser Thr His Val Thr Gly Ala Leu Gln Gly Arg Ala Ala Tyr Gly Ile
 1               5                  10                  15

Thr Ser Phe Leu Ser His Gly Pro Ser Gln Lys
            20                  25

<210> SEQ ID NO 152
<211> LENGTH: 27
<212> TYPE: PRT
<213> ORGANISM: Hepatitis C virus

<400> SEQUENCE: 152

His Thr Arg Val Thr Gly Gly Val Gln Gly His Val Thr Ser Thr Leu
 1               5                  10                  15

Thr Ser Leu Phe Arg Pro Gly Ala Ser Gln Lys
            20                  25

<210> SEQ ID NO 153
<211> LENGTH: 27
<212> TYPE: PRT
<213> ORGANISM: Hepatitis C virus

<400> SEQUENCE: 153

Glu Thr His Thr Ser Gly Gly Ser Val Ala Arg Ala Ala Phe Gly Leu
 1               5                  10                  15

Thr Ser Ile Phe Ser Pro Gly Ala Lys Gln Asn
            20                  25

<210> SEQ ID NO 154
<211> LENGTH: 27
<212> TYPE: PRT
<213> ORGANISM: Hepatitis C virus

<400> SEQUENCE: 154

Glu Thr His Val Thr Gly Gly Ser Ala Gly Arg Thr Thr Ala Gly Leu
 1               5                  10                  15

Val Gly Leu Leu Thr Pro Gly Ala Lys Gln Asn
            20                  25

<210> SEQ ID NO 155
<211> LENGTH: 27
<212> TYPE: PRT
<213> ORGANISM: Hepatitis C virus

<400> SEQUENCE: 155

Ala Thr Tyr Thr Thr Gly Gly Ser Ala Ala Lys Thr Ala His Arg Leu
 1               5                  10                  15

Ala Ser Phe Phe Thr Val Gly Pro Lys Gln Asp
            20                  25

<210> SEQ ID NO 156
<211> LENGTH: 27
<212> TYPE: PRT
<213> ORGANISM: Hepatitis C virus

```
<400> SEQUENCE: 156

Asp Thr His Val Gly Gly Ala Thr Glu Arg Thr Ala Tyr Ser Leu
 1               5                  10                  15

Thr Gly Leu Phe Thr Ala Gly Pro Lys Gln Asn
            20                  25

<210> SEQ ID NO 157
<211> LENGTH: 27
<212> TYPE: PRT
<213> ORGANISM: Hepatitis C virus

<400> SEQUENCE: 157

Gly Thr Thr Cys Gln Gly Gly Val Tyr Ala Arg Gly Ala Gly Gly Ile
 1               5                  10                  15

Ala Ser Leu Phe Ser Val Gly Ala Asn Gln Lys
            20                  25

<210> SEQ ID NO 158
<211> LENGTH: 27
<212> TYPE: PRT
<213> ORGANISM: Hepatitis C virus

<400> SEQUENCE: 158

Arg Thr Leu Ser Phe Gly Gly Leu Pro Gly His Thr Thr His Gly Phe
 1               5                  10                  15

Ala Ser Leu Ser Ala Pro Gly Ala Lys Gln Asn
            20                  25

<210> SEQ ID NO 159
<211> LENGTH: 27
<212> TYPE: PRT
<213> ORGANISM: Hepatitis C virus

<400> SEQUENCE: 159

Arg Thr Ile Leu Met Ala Gly Arg Gln Ala Glu Val Thr Gln Ser Phe
 1               5                  10                  15

Pro Gly Leu Phe Ser Leu Ala Pro Ser Gln Lys
            20                  25

<210> SEQ ID NO 160
<211> LENGTH: 27
<212> TYPE: PRT
<213> ORGANISM: Hepatitis C virus

<400> SEQUENCE: 160

Asn Thr His Ala Met Gly Gly Val Val Ala Arg Ser Ala Tyr Arg Ile
 1               5                  10                  15

Thr Ser Phe Leu Ser Pro Gly Ala Ala Gln Asn
            20                  25

<210> SEQ ID NO 161
<211> LENGTH: 27
<212> TYPE: PRT
<213> ORGANISM: Hepatitis C virus

<400> SEQUENCE: 161

Ser Thr Arg Ile Thr Gly Gly Ser Met Ala Arg Asp Val Tyr Arg Phe
 1               5                  10                  15

Thr Gly Phe Phe Ala Arg Gly Pro Ser Gln Asn
            20                  25
```

```
<210> SEQ ID NO 162
<211> LENGTH: 27
<212> TYPE: PRT
<213> ORGANISM: Hepatitis C virus

<400> SEQUENCE: 162

Gly Thr His Thr Ile Gly Gly Ser Gln Ala Gln Gln Ala Asn Arg Phe
 1               5                  10                  15

Val Ser Met Phe Ser Arg Gly Pro Ser Gln Lys
            20                  25

<210> SEQ ID NO 163
<211> LENGTH: 27
<212> TYPE: PRT
<213> ORGANISM: Hepatitis C virus

<400> SEQUENCE: 163

Asn Thr Tyr Val Thr Gly Gly Ala Ala Ala Arg Gly Ala Ser Gly Ile
 1               5                  10                  15

Thr Ser Leu Phe Ser Arg Gly Pro Ser Gln Lys
            20                  25

<210> SEQ ID NO 164
<211> LENGTH: 27
<212> TYPE: PRT
<213> ORGANISM: Hepatitis C virus

<400> SEQUENCE: 164

Asn Thr Tyr Ala Ser Gly Gly Ala Val Gly His Gln Thr Ala Ser Phe
 1               5                  10                  15

Val Arg Leu Leu Ala Pro Gly Pro Gln Gln Asn
            20                  25

<210> SEQ ID NO 165
<211> LENGTH: 27
<212> TYPE: PRT
<213> ORGANISM: Hepatitis C virus

<400> SEQUENCE: 165

Glu Thr His Thr Thr Gly Gly Glu Ala Ala Arg Thr Thr Leu Gly Ile
 1               5                  10                  15

Ala Ser Leu Phe Thr Ser Gly Ala Asn Gln Lys
            20                  25

<210> SEQ ID NO 166
<211> LENGTH: 27
<212> TYPE: PRT
<213> ORGANISM: Hepatitis C virus

<400> SEQUENCE: 166

Glu Thr His Thr Thr Gly Gly Ser Ala Ala Arg Ala Thr Phe Gly Ile
 1               5                  10                  15

Ala Asn Phe Phe Thr Pro Gly Ala Lys Gln Asn
            20                  25

<210> SEQ ID NO 167
<211> LENGTH: 27
<212> TYPE: PRT
<213> ORGANISM: Hepatitis C virus

<400> SEQUENCE: 167

Glu Thr Tyr Thr Ser Gly Gly Ser Ala Ala His Thr Thr Ser Gly Phe
 1               5                  10                  15
```

Val Ser Phe Phe Ser Pro Gly Ala Lys Gln Asn
            20                  25

<210> SEQ ID NO 168
<211> LENGTH: 27
<212> TYPE: PRT
<213> ORGANISM: Hepatitis C virus

<400> SEQUENCE: 168

Gly Thr Thr Arg Val Gly Gly Ala Ala Arg Thr Thr Ser Ser Phe
 1               5                  10                  15

Ala Ser Leu Leu Thr His Gly Pro Ser Gln Asn
            20                  25

<210> SEQ ID NO 169
<211> LENGTH: 27
<212> TYPE: PRT
<213> ORGANISM: Hepatitis C virus

<400> SEQUENCE: 169

Asn Thr His Thr Val Gly Ala Ala Ala Ser Arg Ser Thr Ala Gly Leu
 1               5                  10                  15

Thr Ser Leu Phe Ser Ile Gly Arg Ser Gln Lys
            20                  25

<210> SEQ ID NO 170
<211> LENGTH: 27
<212> TYPE: PRT
<213> ORGANISM: Hepatitis C virus

<400> SEQUENCE: 170

Asn Thr Arg Val Thr Gly Gly Val Gln Ser Arg Thr Thr Gly Thr Phe
 1               5                  10                  15

Val Gly Leu Phe Thr Pro Gly Pro Ser Gln Arg
            20                  25

<210> SEQ ID NO 171
<211> LENGTH: 27
<212> TYPE: PRT
<213> ORGANISM: Hepatitis C virus

<400> SEQUENCE: 171

Asn Thr His Val Ser Gly Gly Arg Val Gly His Thr Thr Arg Ser Leu
 1               5                  10                  15

Thr Ser Phe Phe Thr Pro Gly Pro Gln Gln Lys
            20                  25

<210> SEQ ID NO 172
<211> LENGTH: 27
<212> TYPE: PRT
<213> ORGANISM: Hepatitis C virus

<400> SEQUENCE: 172

Ser Thr Arg Val Ser Gly Gly Gln Gln Gly Arg Ala Ala His Ser Leu
 1               5                  10                  15

Thr Ser Leu Phe Thr Leu Gly Ala Ser Gln Asn
            20                  25

<210> SEQ ID NO 173
<211> LENGTH: 27
<212> TYPE: PRT
<213> ORGANISM: Hepatitis C virus -continued

```
<400> SEQUENCE: 173

Ser Thr Arg Ile Thr Ala Gln Ala Glu Gly Arg Gly Ala Ser Thr Leu
1               5                   10                  15

Thr Ser Leu Phe Thr Ser Gly Ala Ser Gln Lys
            20                  25

<210> SEQ ID NO 174
<211> LENGTH: 27
<212> TYPE: PRT
<213> ORGANISM: Hepatitis C virus

<400> SEQUENCE: 174

Ser Thr Ile Val Ser Gly Gly Thr Val Ala Arg Thr Thr His Ser Leu
1               5                   10                  15

Ala Ser Leu Phe Thr Gln Gly Ala Ser Gln Lys
            20                  25

<210> SEQ ID NO 175
<211> LENGTH: 27
<212> TYPE: PRT
<213> ORGANISM: Hepatitis C virus

<400> SEQUENCE: 175

Glu Thr Arg Val Thr Gly Gly Ala Ala Gly His Thr Ala Phe Gly Phe
1               5                   10                  15

Ala Ser Phe Leu Ala Pro Gly Ala Lys Gln Lys
            20                  25

<210> SEQ ID NO 176
<211> LENGTH: 27
<212> TYPE: PRT
<213> ORGANISM: Hepatitis C virus

<400> SEQUENCE: 176

Asn Thr Tyr Val Thr Gly Gly Ser Ala Gly Arg Ala Val Ala Gly Phe
1               5                   10                  15

Ala Gly Leu Leu Gln Pro Gly Ala Lys Gln Asn
            20                  25

<210> SEQ ID NO 177
<211> LENGTH: 27
<212> TYPE: PRT
<213> ORGANISM: Hepatitis C virus

<400> SEQUENCE: 177

Glu Thr His Ser Val Gly Gly Ser Ala Ala His Thr Thr Ser Arg Phe
1               5                   10                  15

Thr Ser Leu Phe Ser Pro Gly Pro Gln Gln Asn
            20                  25

<210> SEQ ID NO 178
<211> LENGTH: 27
<212> TYPE: PRT
<213> ORGANISM: Hepatitis C virus

<400> SEQUENCE: 178

Glu Thr His Val Thr Gly Gly Ser Ala Ala Ser Thr Thr Ser Thr Leu
1               5                   10                  15

Thr Lys Leu Phe Met Pro Gly Ala Ser Gln Asn
            20                  25
```

<210> SEQ ID NO 179
<211> LENGTH: 27
<212> TYPE: PRT
<213> ORGANISM: Hepatitis C virus

<400> SEQUENCE: 179

Gln Thr Arg Thr Val Gly Gly Ala Asn Ala Arg Asn Thr Tyr Gly Leu
 1               5                  10                  15

Thr Thr Leu Phe Thr Thr Gly Pro Lys Gln Asn
            20                  25

<210> SEQ ID NO 180
<211> LENGTH: 27
<212> TYPE: PRT
<213> ORGANISM: Hepatitis C virus

<400> SEQUENCE: 180

Gly Thr Thr Thr Val Gly Ser Ala Val Ser Ser Thr Thr Tyr Arg Phe
 1               5                  10                  15

Ala Gly Met Phe Ser Gln Gly Ala Gln Gln Asn
            20                  25

<210> SEQ ID NO 181
<211> LENGTH: 27
<212> TYPE: PRT
<213> ORGANISM: Hepatitis C virus

<400> SEQUENCE: 181

Asn Thr His Thr Val Gly Gly Thr Glu Gly Phe Ala Thr Gln Arg Leu
 1               5                  10                  15

Thr Ser Leu Phe Ala Leu Gly Pro Ser Gln Lys
            20                  25

<210> SEQ ID NO 182
<211> LENGTH: 27
<212> TYPE: PRT
<213> ORGANISM: Hepatitis C virus

<400> SEQUENCE: 182

Asn Thr His Val Thr Gly Gly Val Val Ala Arg Asn Ala Tyr Arg Ile
 1               5                  10                  15

Thr Thr Phe Leu Asn Pro Gly Pro Ala Gln Asn
            20                  25

<210> SEQ ID NO 183
<211> LENGTH: 27
<212> TYPE: PRT
<213> ORGANISM: Hepatitis C virus

<400> SEQUENCE: 183

His Thr Tyr Thr Thr Gly Gly Thr Ala Ser Arg His Thr Gln Ala Phe
 1               5                  10                  15

Ala Gly Leu Phe Asp Ile Gly Pro Gln Gln Lys
            20                  25

<210> SEQ ID NO 184
<211> LENGTH: 27
<212> TYPE: PRT
<213> ORGANISM: Hepatitis C virus

<400> SEQUENCE: 184

Lys Thr His Val Thr Gly Met Val Ala Gly Lys Asn Ala His Thr Leu

-continued

```
                 1               5              10              15
Ser Ser Ile Phe Thr Ser Gly Pro Ser Gln Asn
             20                  25
```

<210> SEQ ID NO 185
<211> LENGTH: 27
<212> TYPE: PRT
<213> ORGANISM: Hepatitis C virus

<400> SEQUENCE: 185

```
Gly Thr His Val Thr Gly Gly Lys Val Ala Tyr Thr Thr Gln Gly Phe
 1               5                  10                  15
Thr Ser Phe Phe Ser Arg Gly Pro Ser Gln Lys
             20                  25
```

<210> SEQ ID NO 186
<211> LENGTH: 27
<212> TYPE: PRT
<213> ORGANISM: Hepatitis C virus

<400> SEQUENCE: 186

```
Glu Thr Tyr Thr Ser Gly Gly Asn Ala Gly His Thr Met Thr Gly Ile
 1               5                  10                  15
Val Arg Phe Phe Ala Pro Gly Pro Lys Gln Asn
             20                  25
```

<210> SEQ ID NO 187
<211> LENGTH: 27
<212> TYPE: PRT
<213> ORGANISM: Hepatitis C virus

<400> SEQUENCE: 187

```
Ser Thr Tyr Ser Met Gly Gly Ala Ala Ala His Asn Ala Arg Gly Leu
 1               5                  10                  15
Thr Ser Leu Phe Ser Ser Gly Ala Ser Gln Arg
             20                  25
```

<210> SEQ ID NO 188
<211> LENGTH: 27
<212> TYPE: PRT
<213> ORGANISM: Hepatitis C virus

<400> SEQUENCE: 188

```
Glu Thr His Val Thr Gly Gly Ser Ala Gly Arg Ser Val Leu Gly Ile
 1               5                  10                  15
Ala Ser Phe Leu Thr Arg Gly Pro Lys Gln Asn
             20                  25
```

<210> SEQ ID NO 189
<211> LENGTH: 27
<212> TYPE: PRT
<213> ORGANISM: Hepatitis C virus

<400> SEQUENCE: 189

```
Glu Thr Tyr Ile Ile Gly Ala Ala Thr Gly Arg Thr Thr Ala Gly Leu
 1               5                  10                  15
Thr Ser Leu Phe Ser Ser Gly Ser Gln Gln Asn
             20                  25
```

<210> SEQ ID NO 190
<211> LENGTH: 27
<212> TYPE: PRT

<213> ORGANISM: Hepatitis C virus

<400> SEQUENCE: 190

Glu Thr His Val Thr Gly Gly Asn Ala Gly Arg Thr Thr Ala Gly Leu
1               5                   10                  15

Val Gly Leu Leu Thr Pro Gly Ala Lys Gln Asn
            20                  25

<210> SEQ ID NO 191
<211> LENGTH: 27
<212> TYPE: PRT
<213> ORGANISM: Hepatitis C virus

<400> SEQUENCE: 191

Glu Thr His Val Thr Gly Gly Ser Ala Gly His Thr Ala Ala Gly Ile
1               5                   10                  15

Ala Ser Phe Phe Ala Pro Gly Pro Lys Gln Asn
            20                  25

<210> SEQ ID NO 192
<211> LENGTH: 27
<212> TYPE: PRT
<213> ORGANISM: Hepatitis C virus

<400> SEQUENCE: 192

Asn Thr Arg Val Thr Gly Gly Val Gln Ser His Thr Thr Arg Gly Phe
1               5                   10                  15

Val Gly Met Phe Ser Leu Gly Pro Ser Gln Arg
            20                  25

<210> SEQ ID NO 193
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 193
gcgagatctt aattaacgat atccagctta taaac                         35

<210> SEQ ID NO 194
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 194
tccggatcct tagtggtggt ggtggtggtg cggtag                        36

<210> SEQ ID NO 195
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 195
ggcggccgtt taattaac                                            18

<210> SEQ ID NO 196
<211> LENGTH: 32
<212> TYPE: DNA
<213> ORGANISM: Artificial Sequence

```
<220> FEATURE:
<223> OTHER INFORMATION: Description of Artificial Sequence: Primer

<400> SEQUENCE: 196
gcgagatctt aattaaccag acccatacca cc                                    32

<210> SEQ ID NO 197
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 197
tccggatcct tagtggtggt ggtggtggtg gttctgtttc gcgcc                      45

<210> SEQ ID NO 198
<211> LENGTH: 6
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Ser, Gly, Ala, Asp, Lys, Arg or Thr
<221> NAME/KEY: SITE
<222> LOCATION: (2)
<223> OTHER INFORMATION: Xaa is Leu, Phe, Ile, Met or Trp
<221> NAME/KEY: SITE
<222> LOCATION: (3)
<223> OTHER INFORMATION: Xaa is Phe or Leu
<221> NAME/KEY: SITE
<222> LOCATION: (4)..(5)
<223> OTHER INFORMATION: Xaa is any amino acid
<221> NAME/KEY: SITE
<222> LOCATION: (6)
<223> OTHER INFORMATION: Xaa is Gly or Ala
<223> OTHER INFORMATION: Description of Artificial Sequence: Consensus
      sequence

<400> SEQUENCE: 198

Xaa Xaa Xaa Xaa Xaa Xaa
 1               5

<210> SEQ ID NO 199
<211> LENGTH: 7
<212> TYPE: PRT
<213> ORGANISM: Artificial Sequence
<220> FEATURE:
<221> NAME/KEY: SITE
<222> LOCATION: (1)
<223> OTHER INFORMATION: Xaa is Ser, Gly, Ala, Asp, Lys, Arg or Thr
<221> NAME/KEY: SITE
<222> LOCATION: (2)
<223> OTHER INFORMATION: Xaa is Leu, Phe, Ile, Met or Trp
<221> NAME/KEY: SITE
<222> LOCATION: (3)
<223> OTHER INFORMATION: Xaa is Phe or Leu
<221> NAME/KEY: SITE
<222> LOCATION: (4)..(5)
<223> OTHER INFORMATION: Xaa is any amino acid
<221> NAME/KEY: SITE
<222> LOCATION: (6)
<223> OTHER INFORMATION: Xaa is Gly or Ala
<221> NAME/KEY: SITE
<222> LOCATION: (7)
<223> OTHER INFORMATION: Xaa is Ala, Pro or Ser
<223> OTHER INFORMATION: Description of Artificial Sequence: Consensus
      sequence
```

<400> SEQUENCE: 199

Xaa Xaa Xaa Xaa Xaa Xaa Xaa
1               5

MIMOTOPES OF HYPERVARIABLE REGION 1 OF THE E2 GLYCOPROTEIN OF HCV AND USES THEREOF

The present invention is concerned with peptides, specifically peptides which are mimotopes of the hypervariable region 1 (HVR1) of the putative envelope protein E2 of hepatitis C virus (HCV). Employing a combination of techniques the present inventors have devised a large number of peptides with sequences based on consensus analysis of naturally occurring HVR1 sequences and experimental determination of cross-reactivity to antibodies against different isolates, none of which peptides occurs in nature. The peptides are individually useful in raising and obtaining antibodies, for in vitro (e.g. diagnostic) and in vivo purposes, and libraries of peptides are useful in identifying peptides of particular cross-reactivity with antibodies able to bind a plurality of HVR1's of different HCV strains. Peptides may be used in themselves or as part of fusion proteins, for instance in recombinant HCV E2 polypeptides, which may be incorporated into recombinant HCV particles.

The HVR1 region of HCV is the most variable antigenic fragment in the whole viral genome and is mainly responsible of the large inter and intra-individual heterogeneity of the infecting virus. It contains a principal neutralization epitope and has been proposed as the major player in the mechanism of escape from host immune response. Since anti-HVR1 antibodies are the only species shown to possess protective activity up to date, the development of an efficient prevention therapy is a very difficult task.

In devising the present invention, the inventors approached the problem of the HVR1 variability by deriving a consensus profile from more than two hundred HVR1 sequences from different viral isolates and used this consensus as a template for generating a vast repertoire of synthetic HVR1 surrogates. These were provided as fusions to the major coat protein VIII of M13 bacteriophage for display on the surface of bacteriophage particles. This library was affinity selected using many different sera from infected patients. Phage were identified which displayed high frequency of reactivity with patients' sera, but not with sera from uninfected controls. The selected sequences were shown to bind serum antibodies cross-reacting with a large panel of peptides reproducing the HVR1 from natural HCV variants.

In these "mimotopes" was identified a sequence pattern responsible for the observed cross-reactivity. When injected in experimental animals, the mimotopes with the highest cross-reactivity induced antibodies able to recognise the same panel of natural HVR1 variants.

Hepatitis C virus (HCV) is the major etiologic agent of both blood-transfusion-associated and sporadic non-A non-B hepatitis worldwide, with an estimated prevalence between 0.4 and 2% in the blood donor population (Choo et al., 1989). HCV infection leads to viral persistence and chronic disease in at least 70% of cases, among which a significant proportion eventually develops cirrhosis and hepatocellular carcinoma (for a review see H. Alter, 1995). In spite of the availability of reliable serological tests for HCV diagnosis, community-acquired infection is still common and causes significant morbidity and mortality worldwide (Mast and Alter, 1993). In addition, interferon treatment, which is the only anti-viral therapy available at the moment, is effective only in 20–30% of patients (Fried and Hoofnagle, 1995). Thus, development of an HCV vaccine represents a high priority project in the field.

The high frequency with which the virus establishes a persistent infection, despite a wide array of humoral and cell-mediated host immune responses, raised in the past some concerns about the existence of a protective immunity against HCV (Farci et al., 1992). As a matter of fact, protective immunity against challenge with homologous virus could be induced by vaccination of chimpanzees (the only other species susceptible to HCV infection) using recombinant forms of the putative envelope proteins E1 and E2 (Choo et al., 1994). However, it remains to be established how effective this response would be against heterologous viral inocula.

HCV exists in the bloodstream of infected patients as a quasispecies (Weiner et al., 1991; Martell et al., 1992; Martell et al., 1994; Kurosaki et al., 1994; Bukh et al., 1995) which fluctuates during the course of the disease mainly as a result of immune pressure (Weiner et al., 1992; Kato et al., 1993; Kojima et al., 1994; Shimizu et al., 1994; van Doorn et al., 1995; Weiner et al., 1995). The emerging view is that chronic infection by HCV is not due to lack of humoral or cellular responses, but rather to such responses being rendered ineffective by the high mutation rate of the virus which leads to the emergence of escape variants.

The existence of neutralising antibodies and their role in protection from viral infection was documented by ex vivo neutralization of a pedigreed viral inoculum prior to injection into chimpanzees (Farci et al., 1994). This notwithstanding, neutralising antibodies were isolate-specific and seemed to be able to block only viral variants which were present before the onset of the corresponding humoral response (Farci et al., 1994). Even if the specificity of such neutralising antibodies is not well defined, both immunological and molecular evidence indicate that epitopes recognised by neutralising antibodies are localised in the hypervariable region 1 (HVR1) of the HCV genome (Farci et al., 1994). This consists of the N-terminal 27 amino acids of the E2 glycoprotein, the most variable region of the whole HCV polyprotein (Weiner et al., 1991). Direct proof for the role of anti-HVR1 antibodies in virus clearance came recently from ex vivo neutralization experiments. A rabbit anti-HVR1 hyperimmune serum raised against the predominant variant of an infectious HCV inoculum abolished its infectivity in one chimp, and partially protected a second animal by blocking propagation of the major variant present in the inoculum (Farci et al., 1996).

Thus, the evidence is that the HVR1 contains a principal neutralization determinant for HCV, and that it should constitute an essential component of an acellular HCV vaccine if one could surmount the problem of its variability. Relevant to this issue is the observation that anti-HVR1 antibodies from human sera display some degree of cross-reactivity to different HVR1 variants (Scarselli et al., 1995).

WO94/26306 (Chiron Corporation) discloses an attempt at identifying a consensus sequence within the HVR1 of HCV, based on sequence comparison on the 90 strains said to have been known as of 12 May 1993. The disclosed formula is of a peptide including the following sequence: aa1-aa2-aa3-aa4-aa5 -aa6 (SEQ ID NO: 198), wherein aa1 is S, G, A, D, K, R or T; aa2 is L, F, I, M or W; aa3 is F or L; aa4 is any amino acid; aa5 is any amino acid; and aa6 is G or A; with the proviso that the motif is not contained within a 31 amino acid sequence of a naturally occurring E2HV domain of an HCV isolate known as of May 12, 1993. In a further embodiment, aa7 is present and attached to aa6 (SEQ ID NO: 199); aa7 being A, P or S. The 6 amino acid motif represents around 55,000 different sequence. The 7 amino acid motif represents around 165,000 different sequences.

Aspects of the present invention are based in part on a close inspection of the variability in HVR1 revealing that some positions of the HVR1 are less variable than others, suggesting that the actual structural, and immunological variability is more limited than that suggested by the heterogeneity in primary sequence. The invention is concerned in various aspects with providing "synthetic variants" of the HCV HVR1 which are immunologically similar to a plurality, preferably a great number of natural HVR1 variants and, therefore, may be used to induce neutralising antibodies which cross-react with different HCV variants, preferably most or all. As explained further below, the formulae arrived at for peptides of the present invention differs from that provided in WO94/26306, and is based on actual cross-reactivity scoring rather than just sequence comparison.

Phage displayed peptide libraries offer the unique chance to rapidly survey large collections of peptidic sequences ($10^8$ or more) through a cyclic selection/rescue/amplification procedure. They allow identification of ligands for any type of ligate ranging from linear peptides to folded protein domains, and even carbohydrates (Cortese et al., 1994, Cortese et al., 1996). These ligands are true mimotopes as they do not necessarily share the same amino acid sequence of the original epitope, but they mimic its binding properties. A strategy for the identification of disease-specific phage-displayed mimotopes was reported previously, which avails itself only of clinically characterized sera from immune and non immune individuals (Folgori et al., 1994, hereby incorporated by reference). Furthermore, disease-specific mimotopes proved to be good immunogenic mimics of the natural antigen as they were able to induce a specific immune response to the natural antigen when injected into different animals (Folgori et al., 1994, and Meola et al., 1995, (both hereby incorporated by reference) Prezzi et al., 1996, Mecchia et al., 1996). Thus, phage libraries may be used as a source of artificial ligands recognised by disease-specific antibodies, with the advantage that additional desirable features can be built-in, providing that they can be selected for during library enrichment.

In making the present invention, the inventors approached the problem of the HVR1 variability by generating a vast repertoire of HVR1 surrogates as fusion to the major coat protein (pVIII) of bacteriophage M13. Using the power of selection and many sera from clinically characterized HCV infected individuals peptides were isolated which revealed to be good antigenic and immunogenic mimics of a large number of naturally occurring HCV variants.

Experimental details are provided below.

In accordance with various aspects of the present invention there are provided libraries of peptides containing large numbers of different peptides, individual peptides which contain epitopes cross-reactive with a plurality of HCV HVR1 epitopes, and mixtures of different such peptides.

One aspect of the present invention provides a library of peptide conforming with the following consensus profile (SEQ ID NO: 1):

This profile represents a total of $9 \times 10^7$ individual sequences, i.e. a number very close to the upper practical limit (about $10^8$) of current DNA cloning and transformation techniques. As described below, this consensus profile was used for the construction of a 27aa peptide library by cloning a degenerated synthetic oligonucleotide as a fusion to the 5' end of the gene coding for the major coat protein (pVIII) in a phagemid vector for M13. The library was extensively screened using human sera, and more than one hundred different clones (mimotopes) were selected for their characteristic to specifically recognise human anti HCV-HVR1 antibodies. Nearly all these mimotopes have different amino acid sequences and none of them could be found to correspond to published (up to January 98) natural HVR1.

In a preferred embodiment of a peptide library according to the present invention there are at least about $10^5$ different peptides present, preferably at least about $10^6$ different peptides, more preferably at least about $10^7$, e.g. about $9 \times 10^7$ different peptides.

A library of peptides may be displayed on the surface of bacteriophage, particularly filamentous bacteriophage such as fd or M13, for instance as fusions with the major coat protein (pVIII) of such bacteriophage. Phage display of peptides is standard in the art and its power lies in the fact that bacteriophage particles are constructed so that packaged within each particle is nucleic acid encoding the peptide displayed on its surface. Following selection of phage particles displaying a peptide of interest, such as a peptide able to bind one or more antibodies (e.g. antibodies able to bind a number of epitopes of HVR1 of different strains of HCV), the nucleic acid encoding the displayed peptide can be retrieved and used in production of further peptide with that amino acid sequence.

In the experimental work described below, the inventors tested mimotopes in a library according to the present invention with a panel of human sera, and individual mimotopes were characterised as having a different overall frequency of reactivity with the sera. The 24 clones that only reacted with less than 3 sera were defined as "weak" while the 27 reacting with more than 11 sera were defined as "strong".

Statistical analysis of the consensus sequences of "strong" and "weak" clones, lead to the discovery of a sequence motif in the HVR1 that is correlated with high frequency of reaction with human sera, crossreactivity with human anti HVR1 antibodies and induction of highly crossreactive sera in experimental animals.

Peptides according to the present invention, and mixtures thereof, may be defined as follows, further explanation of which is given below in the experimental section:

(1)—A library of peptides fully described by the following formula ("Formula I"; SEQ ID NO: 1):

```
Q T H V T G G S A A R T T S G L T S L F S P G A S Q N
T   T T V     V Q G H A A H S   V G   R L   P K   K
    R         Q V S   Q V R R   R     S     S Q
                                      Q
```

```
Q T H V T G G S A A R T T S G L T S L F S P G A S Q N
T   T T V     V Q G H A A H S   V G     R L   P K   K
    R         Q V S   Q V R R     R       S   S Q
                                          Q
``` which may be written as (aa1)T(aa3)(aa4)(aa5)GG(aa8)(aa9)(aa10)(aa11)(aa12)(aa13) (aa14)(aa15)L(aa17)(aa18)LF(aa21)(aa22)G(aa24)(aa25)Q(aa27) wherein aa1 is Q or T; aa3 is H, T or R; aa4 is V or T; aa5 is T or V; aa8 is S, V or Q; aa9 is A, Q or V; aa10 is A, G or S; aa11 is R or H; aa12 is T, A or Q; aa13 is T, A or V; aa14 is S, H or R; aa15 is G, S or R; aa17 is T or V; aa18 is S, G or R; aa21 is S or R; aa22 is P, L, S or Q; aa24 is A, P or S; aa25 is S, K or Q; aa27 is N or K.

(2)-27 "strong" peptides obtainable from such a library are preferred peptides according to various aspects of the present invention, having an amino acid sequence as follows:

```
2.11 QT H TVGGVQG R QAHSLT S LF S P G A SQN  (SEQ ID NO: 2)
D6   QT T TTGGQVS H ATHGLT G LF S L G P QQK  (SEQ ID NO: 3)
D18  QT H TTGGSAS H QASGLT R LF S Q G P SQN  (SEQ ID NO: 4)
F63  QT H VVGGQQG R QVSSLV S LF S P G A SQK  (SEQ ID NO: 5)
G31  TT H TVGGSVA R QVHSLT G LF S P G P QQK  (SEQ ID NO: 6)
L13  QT H TVGGSQA H AAHSLT R LF S P G S SQN  (SEQ ID NO: 7)
M69  QT T VVGGSQA R AAHGLV S LF S L G S KQN  (SEQ ID NO: 8)
Z61  QT H VVGGVQG R QTSGLV G LF S P G S KQN  (SEQ ID NO: 9)
R9   QT T VVGGSQS H TVRGLT S LF S P G A SQN  (SEQ ID NO: 10)
B26  TT T TTGGQAG H QAHSLT S LF S P G A SQK  (SEQ ID NO: 11)
B22  QT H VVGGVQS H QTSGLT S LF S P G A SQK  (SEQ ID NO: 12)
B35  QT H TTGGVQG H QTSRLT S LF S P G P SQN  (SEQ ID NO: 13)
D29  TT T VVGGQAA H QTHSLT S LF S P G A KQN  (SEQ ID NO: 14)
D33  TT T TTGGQQS H TVHGLV G LF S P G S KQN  (SEQ ID NO: 15)
E26  QT H TVGGVQA H TVRGLT S LF S P G S SQN  (SEQ ID NO: 16)
F80  QT H TTGGQAG H TASSLT G LF S P G A KQN  (SEQ ID NO: 17)
F19  QT T TVGGVAS H QAHSLT G LF S P G A KQK  (SEQ ID NO: 18)
F78  QT H TTGGQAG H QAHSLT G LF S P G A KQN  (SEQ ID NO: 19)
H1   QT H TTGGVVG H ATSGLT S LF S P G P SQK  (SEQ ID NO: 20)
L76  TT T TVGGQAS H QTSSLT G LF S P G S KQN  (SEQ ID NO: 21)
M27  QT T TTGGVAS H AAHRLT S LF S P G P QQK  (SEQ ID NO: 22)
M122 QT T TTGGSAS H AVSSLT G LF S P G S KQN  (SEQ ID NO: 23)
M129 QT T VVGGSAG H TASSLV G LF S P G S KQN  (SEQ ID NO: 24)
M119 TT T TVGGQAS H TTSSLT G LF S P G S QQN  (SEQ ID NO: 25)
R5   QT H TTGGQAS H QVSSLV S LF S P G A KQK  (SEQ ID NO: 26)
R6   TT T TTGGQVG H QTSGLT G LF S P G A QQN  (SEQ ID NO: 27)
R27  TT H VVGGSAS H AVRGLT S LF S P G S SQN  (SEQ ID NO: 28)
```

Further preferred peptides according to the present invention have any of the following sequences:

```
B14  QT T VTG_QAS H TTSSLT G LF S P G A SQK  (SEQ ID NO: 29)

B33  aT H aTGGQAA H STHSLT S LF S P G A SQK  (SEQ ID NO: 30)

F81  QT H VTGGSAA H QTgGLT G LF S P G P KQN  (SEQ ID NO: 31)

B18  QT T VVGGQAS H _VSRLT G LF S P G S SQK  (SEQ ID NO: 32)

L72  QT T T___AA H TTSGLT G LF S P G A KQN   (SEQ ID NO: 33)

D20  QT H VTG_VAG R QTSGLV S LF S P G S SQN  (SEQ ID NO: 34)

D30  Q_ _ __GGVQG H TTSSLV G LF S P G S QQN  (SEQ ID NO: 35)

E19  TT H T_GGQQA H TTSRLV S LF S P G A SQK  (SEQ ID NO: 36)

B24  TT T TVGGQAS H TTSSLT G LF S P G A SQK  (SEQ ID NO: 37)

M63  QT H TTGGVVS H QTRSLV G LF S P G P QQN  (SEQ ID NO: 38)
```

The lower case letters are used to identify amino acid residues that vary from Formula 1, while the underlined spaces are included to signify deletions compared with Formula 1, though the flanking amino acids are of course contiguous in the relevant peptides.

These are variants of peptides obtainable from a library in accordance with the present invention, not themselves conforming with Formula I. They were identified in the course of the experiments identified below and originated by PCR errors during library amplification. (See Materials and Methods, "Construction of the HVR1 library".)

(3)—A "strong consensus" ("Formula II"), derived from the consensus of the highly cross-reactive peptides of (2) above.

The statistical analysis of the frequencies of aa in any position in the 27 "strong" in comparison with the frequency in 25 "weak" is shown in Table II, and discussed further below in the experimental section.

```
Formula II (SEQ ID NO: 39):

QT(aa3)TVGGQQS(aa11)QVHSLT(aa18)LF(aa21) (aa22)G(aa24)SQN where: aa3 is H or T; aa11 is H or R; aa18 is G, S or R; aa21
is S; aa22 is P, L or Q; aa24 is A, S or P;
``` which may also be written:

```
QT H TVGGQAS H QASSLT S LF S P G A KQN
   T           R          G      L   S
                          R      Q   P
```

Residues in italics are included because although they have low frequencies they are found in some of the best reactive mimotopes tested (highlighted with an asterisk among the 27 "strong" peptides at II above.

The 27 mimotopes used to derive Formula II are not in it.

108 peptides conform to Formula II and each is an aspect of the invention. The sequences are:

```
1  QTHTV GGQAS HQASS LTSLF SPGAK QN  (SEQ ID NO: 40)

2  QTHTV GGQAS HQASS LTSLF SPGSK QN  (SEQ ID NO: 41)

3  QTHTV GGQAS HQASS LTSLF SPGPK QN  (SEQ ID NO: 42)

4  QTHTV GGQAS HQASS LTSLF SLGAK QN  (SEQ ID NO: 43)

5  QTHTV GGQAS HQASS LTSLF SLGSK QN  (SEQ ID NO: 44)

6  QTHTV GGQAS HQASS LTSLF SLGPK QN  (SEQ ID NO: 45)

7  QTHTV GGQAS HQASS LTSLF SQGAK QN  (SEQ ID NO: 46)
```

-continued

```
 8  QTHTV GGQAS HQASS LTSLF SQGSK QN  (SEQ ID NO: 47)
 9  QTHTV GGQAS HQASS LTSLF SQGPK QN  (SEQ ID NO: 48)
10  QTHTV GGQAS HQASS LTGLF SPGAK QN  (SEQ ID NO: 49)
11  QTHTV GGQAS HQASS LTGLF SPGSK QN  (SEQ ID NO: 50)
12  QTHTV GGQAS HQASS LTGLF SPGPK QN  (SEQ ID NO: 51)
13  QTHTV GGQAS HQASS LTGLF SLGAK QN  (SEQ ID NO: 52)
14  QTHTV GGQAS HQASS LTGLF SLGSK QN  (SEQ ID NO: 53)
15  QTHTV GGQAS HQASS LTGLF SLGPK QN  (SEQ ID NO: 54)
16  QTHTV GGQAS HQASS LTGLF SQGAK QN  (SEQ ID NO: 55)
17  QTHTV GGQAS HQASS LTGLF SQGSK QN  (SEQ ID NO: 56)
18  QTHTV GGQAS HQASS LTGLF SQGPK QN  (SEQ ID NO: 57)
19  QTHTV GGQAS HQASS LTRLF SPGAK QN  (SEQ ID NO: 58)
20  QTHTV GGQAS HQASS LTRLF SPGSK QN  (SEQ ID NO: 59)
21  QTHTV GGQAS HQASS LTRLF SPGPK QN  (SEQ ID NO: 60)
22  QTHTV GGQAS HQASS LTRLF SLGAK QN  (SEQ ID NO: 61)
23  QTHTV GGQAS HQASS LTRLF SLGSK QN  (SEQ ID NO: 62)
24  QTHTV GGQAS HQASS LTRLF SLGPK QN  (SEQ ID NO: 63)
25  QTHTV GGQAS HQASS LTRLF SQGAK QN  (SEQ ID NO: 64)
26  QTHTV GGQAS HQASS LTRLF SQGSK QN  (SEQ ID NO: 65)
27  QTHTV GGQAS HQASS LTRLF SQGPK QN  (SEQ ID NO: 66)
28  QTHTV GGQAS RQASS LTSLF SPGAK QN  (SEQ ID NO: 67)
29  QTHTV GGQAS RQASS LTSLF SPGSK QN  (SEQ ID NO: 68)
30  QTHTV GGQAS RQASS LTSLF SPGPK QN  (SEQ ID NO: 69)
31  QTHTV GGQAS RQASS LTSLF SLGAK QN  (SEQ ID NO: 70)
32  QTHTV GGQAS RQASS LTSLF SLGSK QN  (SEQ ID NO: 71)
33  QTHTV GGQAS RQASS LTSLF SLGPK QN  (SEQ ID NO: 72)
34  QTHTV GGQAS RQASS LTSLF SQGAK QN  (SEQ ID NO: 73)
35  QTHTV GGQAS RQASS LTSLF SQGSK QN  (SEQ ID NO: 74)
36  QTHTV GGQAS RQASS LTSLF SQGPK QN  (SEQ ID NO: 75)
37  QTHTV GGQAS RQASS LTGLF SPGAK QN  (SEQ ID NO: 76)
38  QTHTV GGQAS RQASS LTGLF SPGSK QN  (SEQ ID NO: 77)
39  QTHTV GGQAS RQASS LTGLF SPGPK QN  (SEQ ID NO: 78)
40  QTHTV GGQAS RQASS LTGLF SLGAK QN  (SEQ ID NO: 79)
41  QTHTV GGQAS RQASS LTGLF SLGSK QN  (SEQ ID NO: 80)
42  QTHTV GGQAS RQASS LTGLF SLGPK QN  (SEQ ID NO: 81)
43  QTHTV GGQAS RQASS LTGLF SQGAK QN  (SEQ ID NO: 82)
44  QTHTV GGQAS RQASS LTGLF SQGSK QN  (SEQ ID NO: 83)
45  QTHTV GGQAS RQASS LTGLF SQGPK QN  (SEQ ID NO: 84)
46  QTHTV GGQAS RQASS LTRLF SPGAK QN  (SEQ ID NO: 85)
47  QTHTV GGQAS RQASS LTRLF SPGSK QN  (SEQ ID NO: 86)
```

-continued

```
48  QTHTV GGQAS RQASS LTRLF SPGPK QN   (SEQ ID NO: 87)
49  QTHTV GGQAS RQASS LTRLF SLGAK QN   (SEQ ID NO: 88)
50  QTHTV GGQAS RQASS LTRLF SLGSK QN   (SEQ ID NO: 89)
51  QTHTV GGQAS RQASS LTRLF SLGPK QN   (SEQ ID NO: 90)
52  QTHTV GGQAS RQASS LTRLF SQGAK QN   (SEQ ID NO: 91)
53  QTHTV GGQAS RQASS LTRLF SQGSK QN   (SEQ ID NO: 92)
54  QTHTV GGQAS RQASS LTRLF SQGPK QN   (SEQ ID NO: 93)
55  QTTTV GGQAS HQASS LTSLF SPGAK QN   (SEQ ID NO: 94)
56  QTTTV GGQAS HQASS LTSLF SPGSK QN   (SEQ ID NO: 95)
57  QTTTV GGQAS HQASS LTSLF SPGPK QN   (SEQ ID NO: 96)
58  QTTTV GGQAS HQASS LTSLF SLGAK QN   (SEQ ID NO: 97)
59  QTTTV GGQAS HQASS LTSLF SLGSK QN   (SEQ ID NO: 98)
60  QTTTV GGQAS HQASS LTSLF SLGPK QN   (SEQ ID NO: 99)
61  QTTTV GGQAS HQASS LTSLF SQGAK QN   (SEQ ID NO: 100)
62  QTTTV GGQAS HQASS LTSLF SQGSK QN   (SEQ ID NO: 101)
63  QTTTV GGQAS HQASS LTSLF SQGPK QN   (SEQ ID NO: 102)
64  QTTTV GGQAS HQASS LTGLF SPGAK QN   (SEQ ID NO: 103)
65  QTTTV GGQAS HQASS LTGLF SPGSK QN   (SEQ ID NO: 104)
66  QTTTV GGQAS HQASS LTGLF SPGPK QN   (SEQ ID NO: 105)
67  QTTTV GGQAS HQASS LTGLF SLGAK QN   (SEQ ID NO: 106)
68  QTTTV GGQAS HQASS LTGLF SLGSK QN   (SEQ ID NO: 107)
69  QTTTV GGQAS HQASS LTGLF SLGPK QN   (SEQ ID NO: 108)
70  QTTTV GGQAS HQASS LTGLF SQGAK QN   (SEQ ID NO: 109)
71  QTTTV GGQAS HQASS LTGLF SQGSK QN   (SEQ ID NO: 110)
72  QTTTV GGQAS HQASS LTGLF SQGPK QN   (SEQ ID NO: 111)
73  QTTTV GGQAS HQASS LTRLF SPGAK QN   (SEQ ID NO: 112)
74  QTTTV GGQAS HQASS LTRLF SPGSK QN   (SEQ ID NO: 113)
75  QTTTV GGQAS HQASS LTRLF SPGPK QN   (SEQ ID NO: 114)
76  QTTTV GGQAS HQASS LTRLF SLGAK QN   (SEQ ID NO: 115)
77  QTTTV GGQAS HQASS LTRLF SLGSK QN   (SEQ ID NO: 116)
78  QTTTV GGQAS HQASS LTRLF SLGPK QN   (SEQ ID NO: 117)
79  QTTTV GGQAS HQASS LTRLF SQGAK QN   (SEQ ID NO: 118)
80  QTTTV GGQAS HQASS LTRLF SQGSK QN   (SEQ ID NO: 119)
81  QTTTV GGQAS HQASS LTRLF SQGPK QN   (SEQ ID NO: 120)
82  QTTTV GGQAS RQASS LTSLF SPGAK QN   (SEQ ID NO: 121)
83  QTTTV GGQAS RQASS LTSLF SPGSK QN   (SEQ ID NO: 122)
84  QTTTV GGQAS RQASS LTSLF SPGPK QN   (SEQ ID NO: 123)
85  QTTTV GGQAS RQASS LTSLF SLGAK QN   (SEQ ID NO: 124)
86  QTTTV GGQAS RQASS LTSLF SLGSK QN   (SEQ ID NO: 125)
87  QTTTV GGQAS RQASS LTSLF SLGPK QN   (SEQ ID NO: 126)
```

```
-continued
88   QTTTV GGQAS RQASS LTSLF SQGAK QN    (SEQ ID NO: 127)

89   QTTTV GGQAS RQASS LTSLF SQGSK QN    (SEQ ID NO: 128)

90   QTTTV GGQAS RQASS LTSLF SQGPK QN    (SEQ ID NO: 129)

91   QTTTV GGQAS RQASS LTGLF SPGAK QN    (SEQ ID NO: 130)

92   QTTTV GGQAS RQASS LTGLF SPGSK QN    (SEQ ID NO: 131)

93   QTTTV GGQAS RQASS LTGLF SPGPK QN    (SEQ ID NO: 132)

94   QTTTV GGQAS RQASS LTGLF SLGAK QN    (SEQ ID NO: 133)

95   QTTTV GGQAS RQASS LTGLF SLGSK QN    (SEQ ID NO: 134)

96   QTTTV GGQAS RQASS LTGLF SLGPK QN    (SEQ ID NO: 135)

97   QTTTV GGQAS RQASS LTGLF SQGAK QN    (SEQ ID NO: 136)

98   QTTTV GGQAS RQASS LTGLF SQGSK QN    (SEQ ID NO: 137)

99   QTTTV GGQAS RQASS LTGLF SQGPK QN    (SEQ ID NO: 138)

100  QTTTV GGQAS RQASS LTRLF SPGAK QN    (SEQ ID NO: 139)

101  QTTTV GGQAS RQASS LTRLF SPGSK QN    (SEQ ID NO: 140)

102  QTTTV GGQAS RQASS LTRLF SPGPK QN    (SEQ ID NO: 141)

103  QTTTV GGQAS RQASS LTRLF SLGAK QN    (SEQ ID NO: 142)

104  QTTTV GGQAS RQASS LTRLF SLGSK QN    (SEQ ID NO: 143)

105  QTTTV GGQAS RQASS LTRLF SLGPK QN    (SEQ ID NO: 144)

106  QTTTV GGQAS RQASS LTRLF SQGAK QN    (SEQ ID NO: 145)

107  QTTTV GGQAS RQASS LTRLF SQGSK QN    (SEQ ID NO: 146)

108  QTTTV GGQAS RQASS LTRLF SQGPK QN    (SEQ ID NO: 147)
```

(4)—A further library of peptides within the library of Formula I, including the sequences of Formula II, defining $2.5 \times 10^6$ sequences and conforming to the following Formula III (SEQ ID NO: 148):

```
Q T H T V G G Q A S H Q A S S L T S L F S P G A K Q N
  T V T       S Q G   A T H G   V G           S S   K
              V V A   T V R R                 P Q
```

A peptide according to the present invention may be provided in a fusion with additional amino acids. Additional amino acids may be fused at one or both of the N-terminus and the C-terminus of the peptide. The additional amino acids may be an amino acid sequence that is not a fragment of HCV E2 protein, or may be an amino acid sequence that is part of that protein. Furthermore, a fusion including a peptide according to the present invention may include a HCV E2/NS1 protein with the peptide amino acid sequence in the HVR1 position, i.e. such that the mimotope HVR1 peptide of the invention substitutes for the natural HVR1 sequence. Another way of expressing this is to refer to a "recombinant HCV E2/NS1 protein in which a peptide of the present invention is substituted for the HVR1". As noted below, nucleic acid encoding peptides and polypeptides, including fusions, according to invention are provided as further aspects of the invention, as is a recombinant HCV genome including a nucleotide sequence encoding a peptide of the invention, for instance within the E2/NS1 coding sequence to provide for production of a recombinant HCV E2/NS1 protein in which a peptide of the invention is substituted for the HVR1 and incorporation of the recombinant protein into an assembled HCV particle. A recombinant HCV particle including one or more peptides or polypeptides as disclosed herein is provided as a further aspect of the present invention.

Generally, a peptide according to the present invention is immunogenic or able to raise an immune response on administration to an individual or includes an epitope immunologically cross-reactive with an epitope of a plurality of strains of HCV.

Another aspect of the present invention provides a method of obtaining one or more peptides containing an epitope immunologically cross-reactive with an epitope in the HVR1 of an HCV strain, the method including bringing into contact a library of peptides as disclosed and an antibody molecule able to bind said HVR1 of an HCV strain, and selecting one or more peptides of the library able to bind said antibody molecule.

The peptide or peptides selected may contain an epitope immunologically cross-reactive with the HVR1 of a plurality of strains of HCV.

Such a method may include bringing into contact a library of peptides and a plurality of antibody molecules collectively able to bind the HVR1 of a plurality of strains of HCV. In one embodiment, said plurality of antibody molecules is derived from sera of individuals infected with HCV.

As noted, said library may be displayed on the surface of bacteriophage particles, each particle containing nucleic acid encoding the peptide displayed on its surface. Following selection, nucleic acid may be taken from a bacteriophage particle displaying a said selected peptide. Nucleic acid with the sequence of nucleic acid taken from a bacteriophage particle displaying a said selected peptide may be used in production of such a peptide by means of expression (using recombinant DNA technology as standard in the art and discussed further below).

A peptide with the amino acid sequence of a said selected peptide may provided in isolated form, e.g. after its production by expression from encoding nucleic acid. As noted further below, one or more peptides in accordance with the present invention may be provided by peptide synthesis.

A plurality of peptides each with the amino acid sequence of a different selected peptide may provided in isolated form, individually or in a mixture.

A selected peptide or selected peptides may each have an amino acid sequence according to the Formula II given above. All 108 of the different peptides according to Formula II may be provided as a mixture, and furthermore each individually represents an aspect of the present invention. Each peptide of these 108 has a high probability of being cross-reactive with epitopes in the HVR1 of the E2/NS2 protein of a number of strains of HCV, and therefore is particularly useful for obtaining antibodies or otherwise raising an immune response.

A composition according to the present invention may include a plurality of peptides obtainable from a mixture of the 108 peptides of Formula II. Such a composition may include from 2 to about 20, 15, 10, 9, 8, 7, 6, 5, 4 or 3 different peptides obtainable from said mixture.

Preferred peptides which may be provided in a mixture or individually include those denoted G31, F78, R9, D6, M122 and H1 of which the amino acid sequences are shown in FIG. 7(A). Preferred mixtures included peptides R9, F78, H1 and D6 ("MIX1"), include peptides M122 and G31 ("MIX2"), or include peptides G31, F78, R9, D6, M122 and H1 ("MIX3").

Immunological cross-reactivity of each peptide of the invention with the HVR1 of HCV strains can be assessed experimentally, as exemplified below. Various mixtures of these peptides may also be made and similarly tested, again as experimentally exemplified below.

Linear or branched (e.g. MAP) peptides and polypeptides (e.g. fusion molecules including a peptide as discussed) in accordance with the present invention may be made using any of a variety of techniques at the disposal of the ordinary person skilled in the art.

Linear or branched peptides may be synthesized using standard peptide chemistry such as by the common method employing Fmoc (Fluorenilmetil-ossicarbonil)t-Bu (tertbutil), as described in Atherton and Sheppard (1989), *Solid Phase Peptide Synthesis, a Practical Approach*, IRL Press, Oxford.

A convenient way of producing a peptide or polypeptide according to the present invention is to express nucleic acid encoding it, by use of the nucleic acid in an expression system.

Accordingly, the present invention also encompasses a method of making a peptide or polypeptide (as disclosed), the method including expression from nucleic acid encoding the peptide or polypeptide (generally nucleic acid according to the invention). This may conveniently be achieved by growing a host cell in culture, containing such a vector, under appropriate conditions which cause or allow expression of the polypeptide. Peptides and polypeptides may also be expressed in in vitro systems, such as reticulocyte lysate.

Polynucleotides encoding peptides and polypeptides according to the present invention represent further aspects of the invention.

In one aspect there is provided a polynucleotide encoding a peptide as disclosed. In a further aspect, there is provided a polynucleotide encoding a fusion as disclosed, particularly a HCV E2/NS1 protein including the amino acid sequence of a peptide of the invention in the HVR1 position. In a further aspect, there is provided a recombinant HCV genome including a nucleotide sequence encoding a peptide according to the invention or a fusion as disclosed, particularly a HCV E2/NS1 protein with the relevant peptide amino acid sequence in the HVR1 position.

In a still further aspect, a polynucleotide is provided which includes a plurality of nucleotide sequences encoding peptides or polypeptides according to the invention. This allows for production of a mixture of peptides or polypeptides in a single expression reaction.

Nucleic acid encoding a peptide or polypeptide according to the present invention may be used in nucleic acid immunisation in order to raise an immune response in a mammal, such as a human individual for a therapeutic or prophylactic purpose, or a non-human mammal for such a purpose or in order to produce antibodies for subsequent manipulation and/or use (e.g. in diagnostic or therapeutic contexts as discussed further below.)

Nucleic acid encoding a peptide or polypeptide according to the present invention may be used in a method of gene therapy, in prevention and/or treatment of HCV infection. This requires use of suitable regulatory elements for expression and a suitable vector for deliver of the expression unit (coding sequence and regulatory elements) to host cells. A variety of vectors, both viral vectors and plasmid vectors, are known in the art, see e.g. U.S. Pat. No. 5,252,479 and WO 93/07282. In particular, a number of viruses have been used as gene transfer vectors, including papovaviruses, such as SV40, vaccinia virus, herpesviruses, including HSV and EBV, and retroviruses. Many gene therapy protocols in the prior art have used disabled murine retroviruses. A variety of adenovirus and adeno-associated viral vectors have been developed. Alternatives to viral vectors include transfer mediated by liposomes and direct DNA uptake and receptor-mediated DNA transfer.

Host cells containing nucleic acid encoding a peptide or polypeptide (or mixture thereof) according to the present invention may themselves be used in therapeutic or prophylactic treatment of individuals for or against HCV infection (i.e. therapeutic treatment of an individual with an HCV infection or prophylactic treatment of an individual prior to HCV infection).

Nucleic acid is generally provided as DNA or RNA, though may include one or more nucleotide analogues, and may be wholly or partially synthetic. Nucleic acid molecules and vectors according to the present invention may be provided in isolated and/or purified form, e.g. in substantially pure or homogeneous form. The term "isolate" may be used to reflect all these possibilities. Where a DNA sequence is specified, e.g. with reference to a figure, unless context requires otherwise the RNA equivalent, with U substituted for T where it occurs, is encompassed.

Where it is desired to express a peptide or polypeptide from encoding nucleic acid, the nucleic acid includes appropriate regulatory control sequences. Suitable vectors can be chosen or constructed, containing appropriate regulatory sequences, including promoter sequences, terminator fragments, polyadenylation sequences, enhancer sequences, marker genes and other sequences as appropriate. Vectors may be plasmids, viral e.g. phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Ausubel et al. eds., John Wiley & Sons, 1992.

Systems for cloning and expression of a polypeptide in a variety of different host cells are well known. Suitable host cells include bacteria, eukaryotic cells such as mammalian and yeast, and baculovirus systems. Mammalian cell lines available in the art for expression of a heterologous polypeptide include Chinese hamster ovary cells, HeLa cells, baby hamster kidney cells, COS cells and many others. A common, preferred bacterial host is *E. coli.*

A further aspect of the present invention provides a host cell containing nucleic acid as disclosed herein. The nucleic acid of the invention may be integrated into the genome (e.g. chromosome) of the host cell; Integration may be promoted by inclusion of sequences which promote recombination with the genome, in accordance with standard techniques. The nucleic acid may be on an extra-chromosomal vector within the cell.

A still further aspect provides a method which includes introducing the nucleic acid into a host cell. The introduction, which may (particularly for in vitro introduction) be generally referred to without limitation as "transformation", may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. As an alternative, direct injection of the nucleic acid could be employed. Marker genes such as antibiotic resistance or sensitivity genes may be used in identifying clones containing nucleic acid of interest, as is well known in the art.

The introduction may be followed by causing or allowing expression from the nucleic acid, e.g. by culturing host cells (which may include cells actually transformed although more likely the cells will be descendants of the transformed cells) under conditions for expression of the gene, so that the encoded peptide or polypeptide is produced. If the peptide or polypeptide is expressed coupled to an appropriate signal leader peptide it may be secreted from the cell into the culture medium. Following production by expression, a peptide or polypeptide may be isolated and/or purified from the host cell and/or culture medium, as the case may be, and subsequently used as desired, e.g. in the formulation of a composition which may include one or more additional components, such as a pharmaceutical composition which includes one or more pharmaceutically acceptable excipients, vehicles or carriers (e.g. see below).

A peptide or polypeptide according to the present invention may be used as an immunogen or otherwise in obtaining binding antibodies. Antibodies are useful in purification and other manipulation of polypeptides and peptides, diagnostic screening and therapeutic contexts, including passive immunisation. This is discussed further below.

According to a further aspect of the present invention there is provided a method of obtaining one or more antibody molecules containing a binding site able to bind an epitope in the HVR1 of a plurality of HCV strains, the method including bringing into contact a population of antibody molecules and a peptide according to the present invention, and selecting one or more antibody molecules of the population able to bind said peptide.

The method may involve bringing the population of antibodies into contact with a plurality of peptides according to the invention.

As noted, the peptides may be provided in a fusion with additional amino acids.

The peptide or peptides may be administered to a non-human mammal to bring them into contact with a population of antibody molecules produced by the mammal's immune system, then one or more antibody molecules able to bind the peptide or peptides may be taken from the mammal, or cells producing such antibody molecules may be taken from the mammal.

The mammal may be sacrificed.

If cells are taken from the mammal, antibody molecules may be taken from said cells or descendants thereof. Such descendants in particular may include hybridoma cells.

Instead or as well as immunising an animal, a method of obtaining antibodies as disclosed may involve displaying the population of antibody molecules on the surface of bacteriophage particles, each particle containing nucleic acid encoding the antibody molecule displayed on its surface. Nucleic acid may be taken from a bacteriophage particle displaying an antibody molecule able to bind a peptide or peptides of interest, for manipulation and/or use in production of the encoded antibody molecule or a derivative thereof (e.g. a fusion protein, a molecule including a constant region or other amino acids, and so on). Instead of using bacteriophage for display, ribosomes or polysomes may be used, e.g. as disclosed in U.S. Pat. No. 5,643,768, U.S. Pat. No. 5,658,754, WO95/11922.

Antibody molecules may be provided in isolated form, either individually or in a mixture. A plurality of antibody molecules may be provided in isolated form.

Preferred antibodies according to the invention are isolated, in the sense of being free from contaminants such as antibodies able to bind other polypeptides and/or free of serum components. Monoclonal antibodies are preferred for some purposes, though polyclonal antibodies are within the scope of the present invention. Indeed, polyclonal mixtures able to bind one or more peptides or polypeptides according to the present invention are preferred in some embodiments, as discussed. Thus, the present invention in a further aspect is directed to a mixture of different antibodies able to bind one or more peptides or polypeptides according to the invention. Such a mixture may be provided in a composition including at least one additional component, such as a pharmaceutically acceptable excipient or vehicle.

The present invention also extends to methods of obtaining and/or raising antibodies to one or more peptides or polypeptides of the invention. Such methods may include administering a peptide or polypeptide or mixture of peptides or polypeptides to a mammal in order to raise an antibody response. In a therapeutic or prophylactic context the mammal may be human or non-human. For the production of antibodies or antibody-producing cells to be isolated and used for any of a variety of purposes, a step of sacrificing a non-human mammal may be included. Such a non-human mammal may be for example mouse, rat, rabbit, dog, cat, pig, horse, donkey, goat, sheep, camel, Old World monkey, chimpanzee or other primate. Antibodies may be obtained from immunised animals using any of a variety of techniques known in the art, and screened, preferably using binding of antibody to peptide or polypeptide of interest. For instance, Western blotting techniques or immunoprecipitation may be used (Armitage et al, Nature, 357:80–82, 1992).

The production of polyclonal and monoclonal antibodies is well established in the art. Monoclonal antibodies can be subjected to the techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP-A-184187, GB-A-2188638 or EP-A-239400. Humanised antibodies in which CDRs from a non-human source are grafted onto human framework regions, typically with the alteration of some of the framework amino acid residues, to provide antibodies which are less immunogenic than the parent non-human antibodies, are also included within the present invention. A hybridoma producing a monoclonal antibody according to the present invention may be subject to genetic mutation or other changes, which may or may not alter the binding specificity of antibodies produced. Cloning and expression of chimeric antibodies are described in EP-A-0120694 and EP-A-0125023.

As an alternative or supplement to immunising a mammal with a peptide, an antibody specific for a protein may be obtained from a recombinantly produced library of expressed immunoglobulin variable domains, e.g. using bacteriophage which display functional immunoglobulin binding domains on their surfaces—for instance see WO92/01047—or ribosomes/polysomes as noted above. The library may be naive, that is constructed from sequences obtained from an organism which has not been immunised with any of the proteins (or fragments), or may be one constructed using sequences obtained from an organism which has been exposed to the antigen of interest.

Antibodies according to the present invention may be modified in a number of ways. Indeed the term "antibody" should be construed as covering any binding substance having a binding domain with the required specificity. Thus the invention covers antibody fragments, derivatives, functional equivalents and homologues of antibodies, including synthetic molecules and molecules whose shape mimics that of an antibody enabling it to bind an antigen or epitope.

Example antibody fragments, capable of binding an antigen or other binding partner are the Fab fragment consisting of the VL, VH, Cl and CH1 domains; the Fd fragment consisting of the VH and CH1 domains; the Fv fragment consisting of the VL and VH domains of a single arm of an antibody; the dAb fragment which consists of a VH domain; isolated CDR regions and F(ab')2 fragments, a bivalent fragment including two Fab fragments linked by a disulphide bridge at the hinge region. Single chain Fv fragments are also included.

Hybridomas capable of producing antibody with desired binding characteristics are within the scope of the present invention, as are host cells, eukaryotic or prokaryotic, containing nucleic acid encoding antibodies (including antibody fragments) and capable of their expression. The invention also provides methods of production of the antibodies including growing a cell capable of producing the antibody under conditions in which the antibody is produced, and preferably secreted.

The reactivities of antibodies on a sample (e.g. in a diagnostic test) may be determined by any appropriate means. Tagging with individual reporter molecules is one possibility. The reporter molecules may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule.

One favoured mode is by covalent linkage of each antibody with an individual fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

The mode of determining binding is not a feature of the present invention and those skilled in the art are able to choose a suitable mode according to their preference and general knowledge.

Antibodies according to the present invention may be used in screening for the presence of a peptide or polypeptide, for example in a test sample containing cells or cell lysate as discussed, and may be used in purifying and/or isolating a peptide or polypeptide according to the present invention, for instance following production of the polypeptide by expression from encoding nucleic acid therefor.

Antibodies are also useful in prophylaxis, by way of passive immunisation, and in therapy. Where antibodies are to be administered, it may be preferable to include a mixture of antibodies, such as antibodies collectively cross-reactive with a plurality of peptides according to the present invention.

Antibodies which bind a peptide in accordance with the present invention may themselves be used as immunogens in the production of anti-idiotypic antibodies. These may be used to mimic a peptide epitope in raising an immune response in an individual, e.g. for therapeutic and/or prophylactic purposes.

An antibody may be provided in a kit, which may include instructions for use of the antibody, e.g. in determining the presence of a particular substance in a test sample. One or more other reagents may be included, such as labelling molecules, buffer solutions, elutants and so on. Reagents may be provided within containers which protect them from the external environment, such as a sealed vial.

Diagnostic methods make use of biological samples from individuals that may contain one or more HCV strains.

Examples of biological samples include fluid such as blood, plasma, serum, urine and saliva, and tissue samples.

There are various methods for determining the presence or absence in a test sample of a particular peptide or polypeptide, including methods wherein the polypeptide to be detected is an antibody.

A sample may be tested for the presence of a specific binding member such as an antibody (or mixture of antibodies) directed to one or more peptides of the invention.

Peptides according to the present invention may be used to determine the presence or absence of antibodies against HCV strains in test samples, by assessment of binding the peptides to anti-HCV E2HVR1 antibodies if present in the sample.

In theory it may be possible to identify the presence in a sample of a binding partner for a specific binding member such as an antibody (or mixture of antibodies) directed to one or more peptides of the invention. However, to date no-one has succeeded in isolating HCV virions from a human sample. In the future, should it prove possible to identify HCV virions in human samples and/or detect such virions immunologically, peptides of the invention and particularly antibodies directed thereto will be useful in such detection.

For detection of antibodies to HCV, a biological or other sample may be tested by being contacted with one or more peptides of the invention under appropriate conditions for specific binding, before binding is determined, for instance using a reporter system as discussed. Where a panel of peptides is used, different reporting labels may be employed for each peptide so that binding of each can be determined.

A specific binding member such as a peptide may be used to isolate and/or purify its binding partner antibody from a test sample, to allow for sequence and/or biochemical analysis of the antibody. Amino acid sequencing is routine in the art using automated sequencing machines.

A typical immunoassay may involve incubating a test sample with peptides according to the invention under conditions to allow formation of immune complexes if an appropriate antibody is present in the sample, and detecting the presence or absence of immune complex.

As noted, although not technically feasible at the moment, in principle antibodies according to the present invention may be used to determine the presence or absence of HCV strains in test samples, by assessment of binding of the antibodies to E2HVR1 epitopes if present in the sample.

A typical immunoassay may involve incubating a test sample with peptides or anti-idiotypic antibodies according to the invention under conditions to allow formation of immune complexes if an appropriate antibody is present in the sample, and detecting the presence or absence of immune complex.

A sample may be tested for the presence of an antibody directed to one or more peptides of the invention, using one or more such peptides (or polypeptide including such peptide) or one or more anti-idiotypic antibodies.

A biological or other sample may be tested by being contacted with a peptide or polypeptide or anti-idiotypic antibody under appropriate conditions for specific binding, before binding is determined, for instance using a reporter system as discussed.

The detection of formation of a binding complex in an immunoassay in accordance with the present invention may be performed using any available technique without limitation to the scope of the invention. Some suitable techniques are described above with reference to antibody labelling. Assays may involve immobilising antibody or peptide, as the case may be, on a suitable solid phase or support, such as latex particles, magnetic or non-magnetic beads, a membrane, chip, plastic, metal, silicon or glass surface, or any other suitable material at the disposal of the skilled person. Detection may be qualitative or quantitative. One or more appropriate controls may be included, in accordance with standard practice.

As noted already, peptides, polypeptides, antibodies and nucleic acid in accordance with the present invention may be formulated into compositions, and are useful in pharmaceutical contexts. These compositions may include, in addition to one of the above substances, a pharmaceutically acceptable excipient, carrier, buffer, stabiliser or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

Compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Branched peptides, such as MAP (Tam, J. P, 1988) may be used for the preparation of immunogens, either alone or linked to an appropriate carrier.

A linear peptide for use in raising an immune response may also be linked to an appropriate carrier. Various methods of coupling peptides to other molecules are known in the art, including disulphide forming reagents (where the peptide includes a cysteine—or a cysteine is added to the peptide for this purpose), thio-ether forming coupling agents and so on. Carriers include human serum albumin (HSA), tetanus toxoid, other rather large proteins that have reasonable half-lives under physiological conditions, and stable non-proteinaceous molecules such as polysaccharides and copolymers of amino acids.

An adjuvant may be included, such as alum, oil-in-water emulsions or Freund's Adjuvant (Complete or Incomplete). Cytokines may be used to potentiate immunogenicity of the peptide or polypeptide composition.

Mimotope sequences may be cloned into the context of the HCV envelope (E2) protein in order to use the natural folding environment for correct presentation of the epitope or epitopes to the immune system.

Naked DNA may be used for immunization (see e.g. Cohen, J, 1993), and one or more mimotope sequences may be cloned into suitable vectors (see e.g. Major et al., 1995). Naked DNA may be delivered using direct injection or by use of gene-guns (Yang et al., 1990) or any other suitable technique.

Whether it is a polypeptide, antibody, peptide, nucleic acid molecule, small molecule or other pharmaceutically useful compound according to the present invention that is to be given to an individual, administration may be in an immunogenic amount, that is sufficient to raise an immune (particularly antibody) response in the individual, or in a "prophylactically effective amount" or a "therapeutically effective amount" (as the case may be, although prophylaxis may be considered therapy). A prophylactic effect is sufficient to potentiate the immune response of an individual to a subsequent challenge with HCV, E2HV polypeptide, or HVR1 peptide, or to a subsequent infection with HCV, preferably in the latter case (HCV infection) to sufficient to antagonise the infection, wholly or partially. Most preferably the effect is sufficient to prevent the individual from suffering one or more clinical symptoms as a result of subsequent HCV infection, and/or protect the individual from hepatitis C. A therapeutic effect is sufficient to potentiate the immune response of an individual to pre-existing HCV infection, preferably sufficient to antagonise the infection, wholly or partially. Most preferably the effect is sufficient to ameliorate one or more clinical symptoms, and/or cure the hepatitis C and/or reduce viral titre in the individual. The actual amount administered, and rate and time-course of administration, will depend on the nature and severity of what is being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980.

Further aspects of the invention provide methods of treatment including administration of a peptide, mixture of peptides, antibody molecule or mixture of antibody molecules, as provided, pharmaceutical compositions including such a peptide, mixture of peptides, antibody molecule or mixture of antibody molecules, and use of such a peptide, mixture of peptides, antibody molecule or mixture of antibody molecules, in the manufacture of a medicament for administration, for example in a method of making a medicament or pharmaceutical composition including formulating the specific binding member with a pharmaceutically acceptable excipient.

A composition may be administered alone or in combination with other treatments, either simultaneously or sequentially dependent upon the condition to be treated and the availability of alternative or additional treatments.

One aspect of the present invention provides use of a peptide as disclosed in the manufacture of a medicament for raising in a mammal antibodies able to bind HCV HVR1 epitopes.

Another aspect provides a method of immunising a mammal against HCV infection, the method including administering a peptide or mixture of peptides to the mammal.

A still further aspect provides a method of (passively) immunising a mammal against HCV infection, the method including administering an antibody according to the invention to the mammal, or a mixture of antibodies.

Similarly, further aspects of the invention provide a method of treating a mammal with an HCV infection, the method including administering a peptide according to the invention, or a mixture of peptides, or an antibody, or a mixture of antibodies, to the mammal.

The antibodies may be anti-idiotypic antibodies.

Aspects and embodiments of the present invention will now be illustrated further and experimentally exemplified with reference to various figures. Further aspects and embodiments of the present invention will be apparent to those of ordinary skill in the art.

IN THE FIGURES

FIG. 1(A) illustrates derivation of the consensus pattern of the 234 natural variants of the HCV HVR1 sequences used in this work. Non shaded residues within the box account alone for about 80% of the observed variability. Residues are listed in decreasing order of observed frequency from top to bottom.

FIG. 1(B) shows the composition in the initial HVR1 peptide library which was displayed on bacteriophage (SEQ ID NO: 1).

FIG. 2 shows reactivity of phage pools yielded by the first round of affinity selection to antibodies present in the selecting sera. For each serum sample ($\sigma 1$, $\sigma 4R$, $\sigma 3$, $\sigma 2P$, $\sigma 2R$, $\sigma 3R$ and $\sigma N$) antibody recognition of the phage pools (pool 1, 4R 3, 2P, 2R, 3R and N), wild type phage (wt) and the unselected library (HVR1 lib) was measured. Average values ($A_{405\ nm}$) from two independent experiments have been determined.

FIG. 3 shows distribution of HCV-specific phage selected from the HVR1 library as function of their frequency of reactivity with sera from infected patients. Binding is shown for phage enriched by one (top panel) or two (bottom panel) cycles of affinity selection to antibodies present in twenty human sera different from those used for the selections. For each serum, average values ($A_{405\ nm}$) from two independent experiments have been determined on the selected phage and on wild type phage. Values were considered statistically significant when differing more than $3\sigma_{max}$ ($p<0.003$) from the background signal observed for the wild type phage. Each histogram represents the number of phage (shown on the vertical axis) reacting with the indicated number of sera expressed as percentage over total number of tested samples (horizontal axis).

FIG. 4 shows that the selected mimotopes are frequently recognized by antibodies present in human sera from HCV infected patients. Binding of the selected mimotopes to antibodies present in human sera was detected by ELISA on immobilised phage. Mimotopes' names are indicated at the top of each column. For each serum (indicated on the left of each row), average values ($A_{405\ nm}$) from two independent experiments have been determined. Results are expressed as the difference between the average value of the tested phagotope and that of wild type phage. Positive values are indicated in bold. Values were considered statistically significant when differing more than $3\sigma_{max}$ ($p<0.003$) from the background signal observed for the wild type phage. The frequency of reactivity of each mimotope and that resulting from the sum of the reactivities observed with all four mimotopes are shown at the bottom of each panel.

FIG. 4(A) shows reactivity of selected mimotopes with the panel of twenty HCV patients' sera used for the screening step.

FIG. 4(B) shows reactivity of selected mimotopes with an additional panel of sera from HCV-infected viremic patients.

FIG. 4(C) shows reactivity with sera from non viremic patients that were scored positive for anti-HCV antibodies using commercially available kits.

Figure 5:
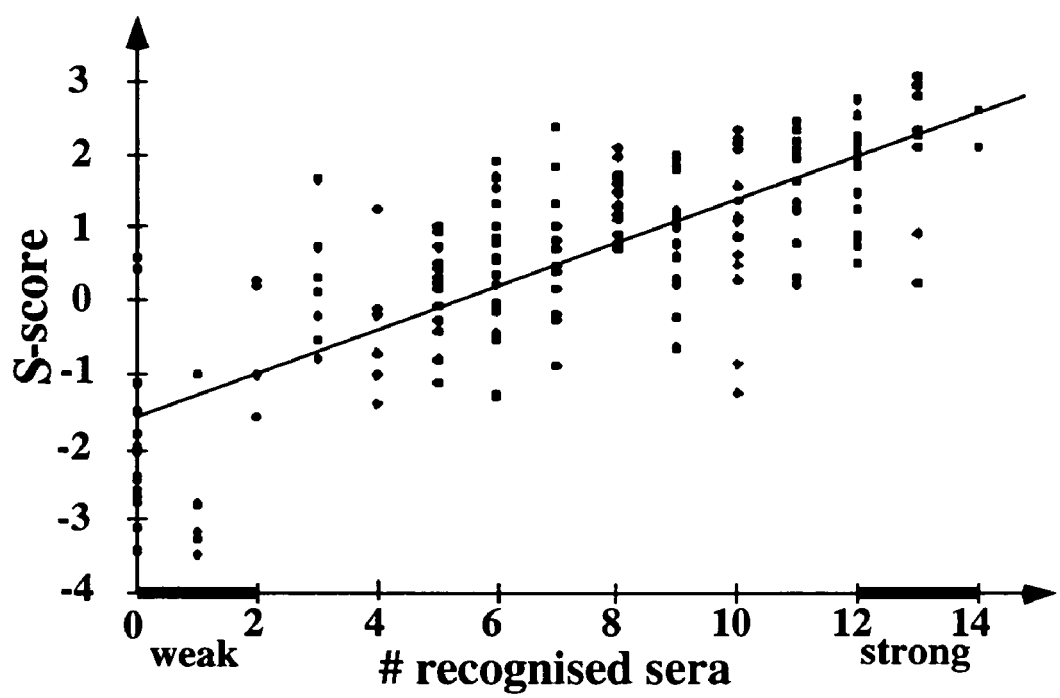

FIG. 5 shows correlation between the S-score and the frequency of reactivity of the selected mimotopes. The straight line represents the linear least square fit of the data. The correlation coefficient is 0.79.

Figure 6:
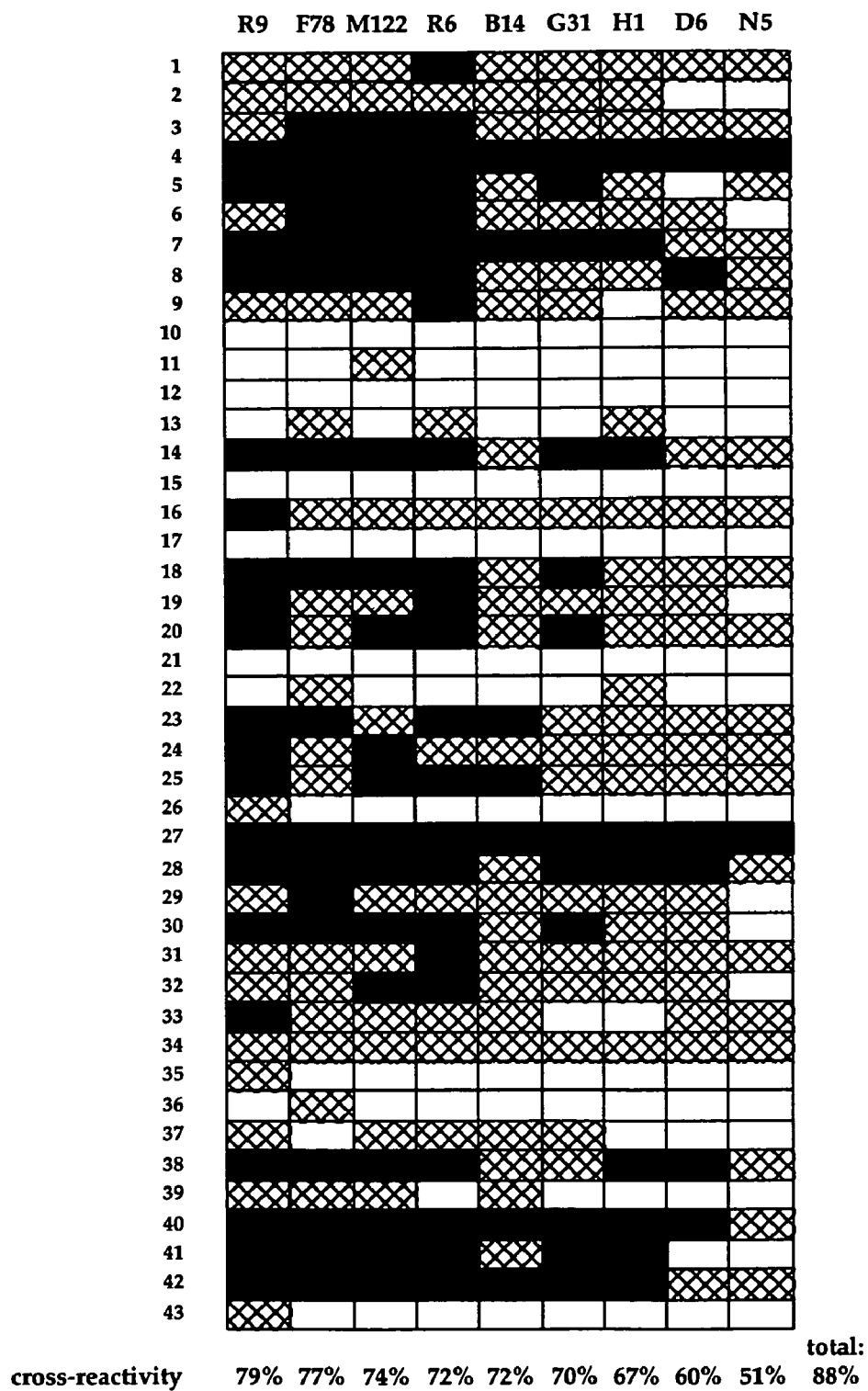

FIG. 6 shows that the selected mimotopes are antigenic mimics of a large number of naturally occurring HVR1.

Antibodies from a pool of sera from HCV infected patients were immunopurified on MAPs reproducing the sequence of selected mimotopes (indicated at the top of the figure). Reactivity of equal amounts of the immunopurified antibodies was measured by ELISA on a representative panel of HVR1 sequences synthesized as MAPs (indicated in the left column). Average values from two independent experiments were determined. Values were considered statistically significant when two criteria were contemporarily fulfilled: (1) values were differing more than $3\sigma_{max}$ (p<0.003) from the background signal observed on two unrelated peptides; (2) values were differing more than $3\sigma_{max}$ (p<0.003) from the average signal observed using ten sera from non infected individuals on each peptide representing a natural HVR1. Grey boxes indicate signals differing from those observed on the unrelated MAPs between 0.15 and 0.5 OD (405 nm); black boxes indicate values differing more than 0.5 OD (405 nm). The level of cross-reactivity of each pool of immunopurified antibodies is indicated at the bottom of each column.

Figure 7:
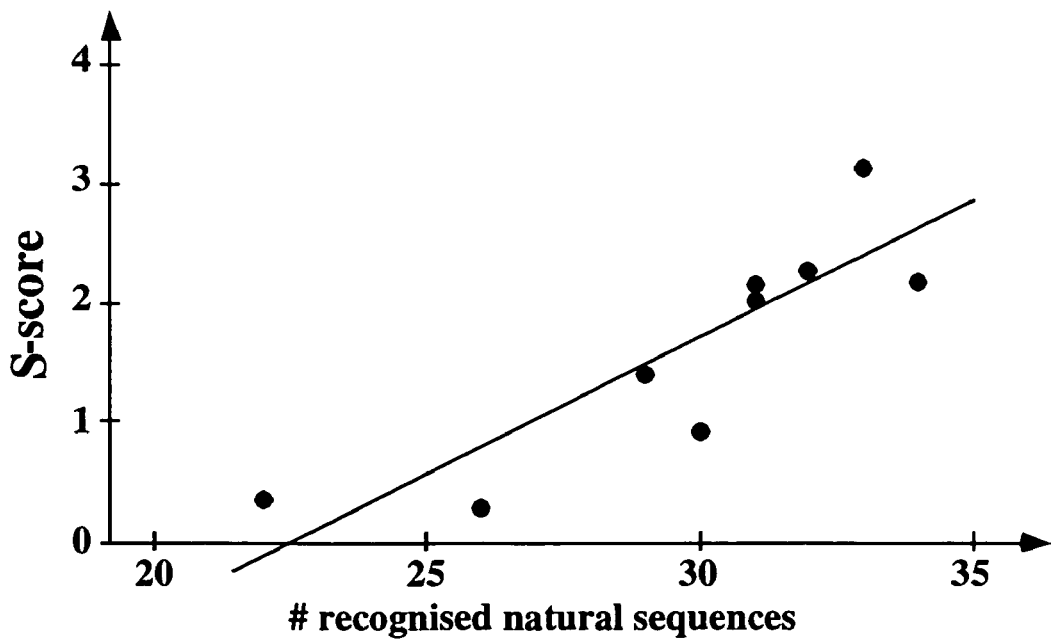

FIG. 7 shows correlation between mimotope sequence and cross-reactivity.

FIG. 7(A) shows the sequences of the mimotopes used in the analysis (SEQ ID NOS: 149, 27, 3, 10, 20, 6, 23, 29 and 19).

FIG. 7(B) shows correlation between the S-score of the mimotopes and the cross-reactivity of immunopurified human antibodies with a panel of 43 natural HVR1 sequences. The straight line represents the linear least square fit of the data. The correlation coefficient is 0.86.

Figure 8:
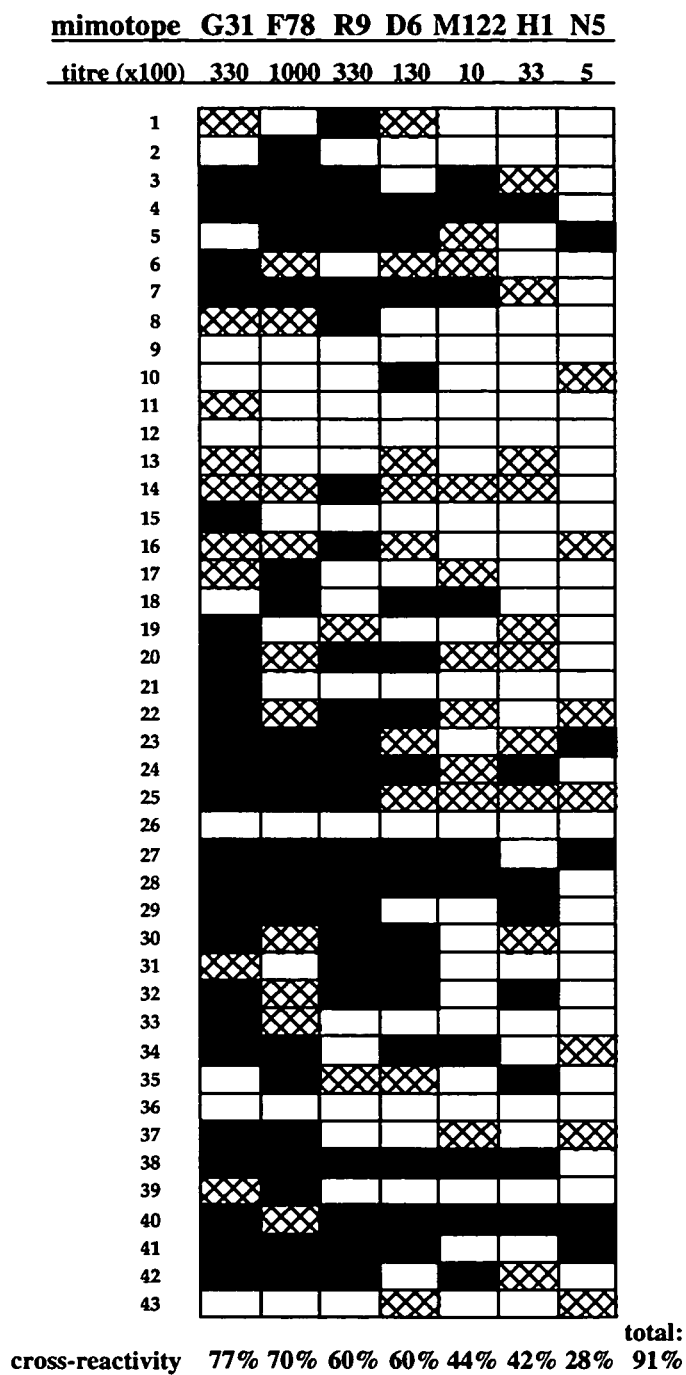
Figure 8:
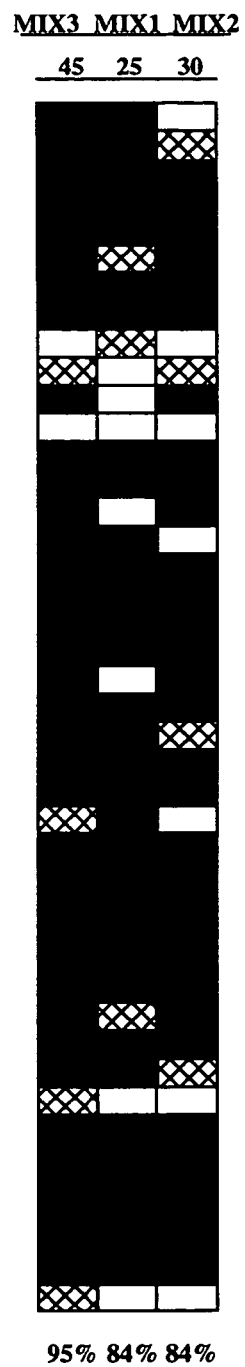

FIG. 8 shows that the selected mimotopes are immunogenic mimics of a large number of naturally occurring HVR1. Reactivity of sera from mice immunised with single HVR1 mimotopes (FIG. 8(A)) and mixtures of mimotopes (FIG. 8(B)) in the form of MAP was assayed by ELISA on the panel of natural HVR1 sequences (indicated in the left column). Immunizing mimotopes are shown in the first row. MIX1 includes mimotopes R9, F78, H1 and D6; MIX2 contains M122 and G31 peptides; MIX3 is composed of all six MAPs. Titres (defined as the dilution required to obtain half maximal signal in ELISA on the homologous peptide) are shown in the second row. Sera were diluted 1:100. Average values from two independent experiments have been determined. Values were considered statistically significant when differing more than $3\sigma_{max}$ (p<0.003) from the background signal observed on two unrelated peptides. Grey boxes indicate signals differing from those observed on the unrelated MAPs between 0.15 and 0.5 OD (405 nm); black boxes indicate values differing more than 0.5 OD (405 nm). The level of cross-reactivity of each serum is indicated at the bottom of each column.

Figure 9:
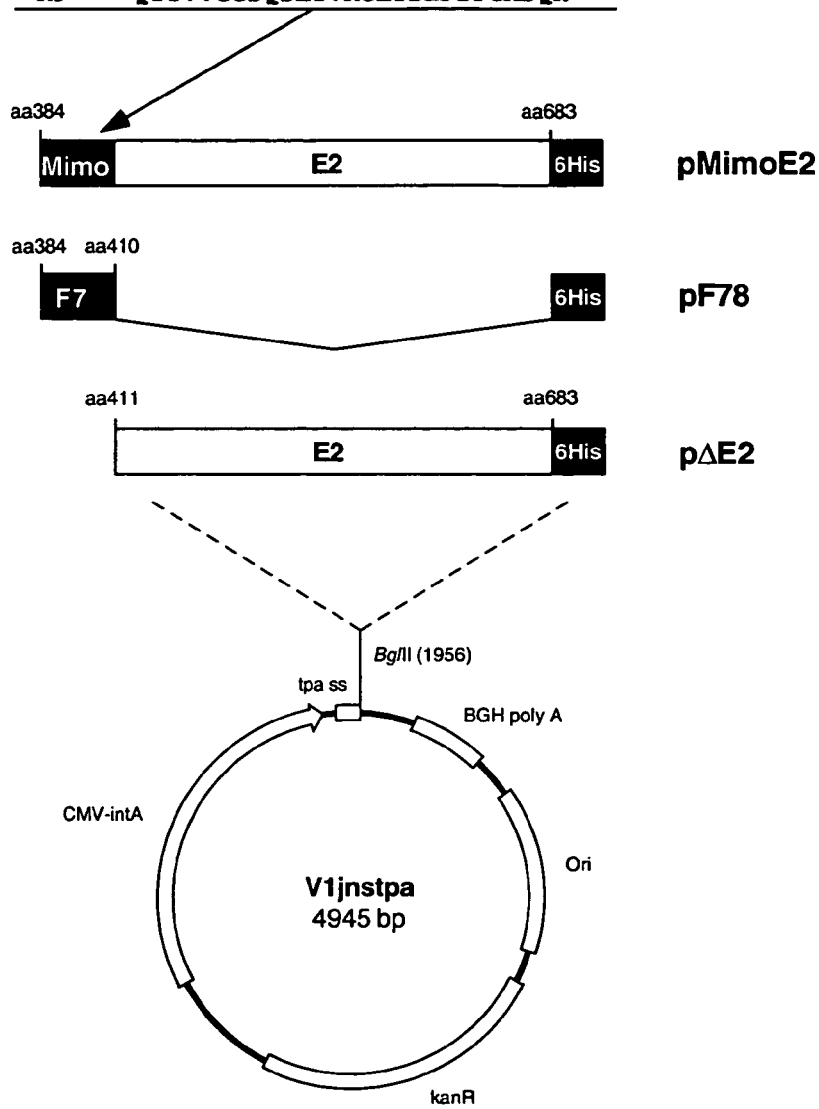

FIG. 9 illustrates plasmids employed in in vivo nucleic acid immunisation experiments described in Example 6 (SEQ ID NOS: 29, 37, 3, 36, 19, 6, 20, 38, 23, 27 and 10).

EXAMPLE 1

Design and Construction of a Specialised Phage Library Mimicking the HVR1 Variability A multiple sequence alignment of 234 unique HVR1 sequences extracted from the sequence databases was made to characterise the variation in residue composition at each of the N-terminal 27 positions of the HCV E2 glycoprotein. A sequence pattern emerged from this analysis (FIG. 1A) allowing the definition of a degenerate consensus sequence. A synthetic repertoire of HVR1 sequences was designed to contain such conserved constraints while reproducing the observed natural variability in the remaining positions.

Figure 1:
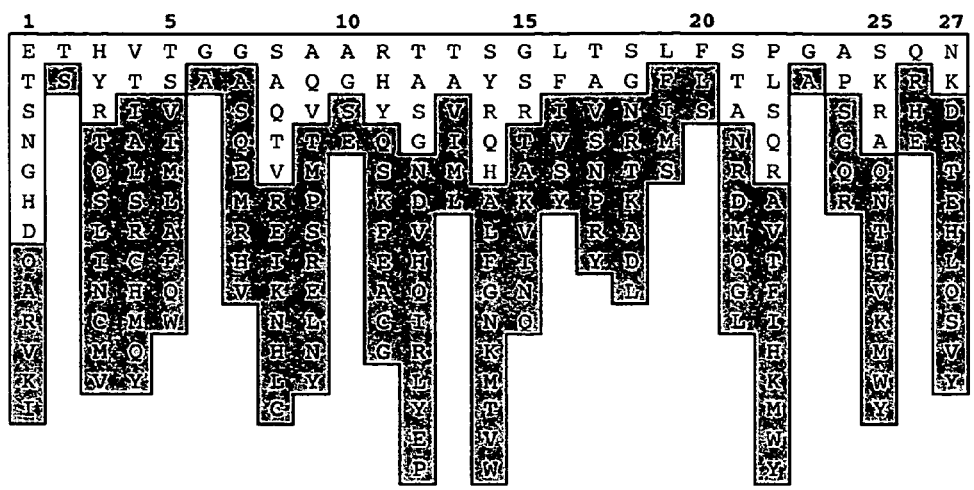

A "consensus-profile" accounting for approximately 80% of the total sequence variability was derived by selecting the most frequent residues at each position. When similar amino acids were present at a given position, only one was chosen as representative of the variability, preferring those residues which could more effectively form interactions. For example, in position 5 both Ser and Thr are present in the natural repertoire, but only Thr was selected to design the library (FIG. 1). In some cases, a residue not present in the consensus was included in the library to better mirror the overall variability. For example, Thr was included in position 3 to account for the presence of Ser, Thr, Asn in the natural repertoire of HVR1s.

The resulting final consensus profile (FIG. 1B) has a complexity of $9 \times 10^7$ very close to the upper practical limit (about $10^8$) of current DNA cloning and transformation techniques. The amino acid most frequently observed in the natural repertoire was always included with the exception of position 1, (where Gln and Thr were selected although Glu is the most frequently observed amino acid). Eight positions (2, 6, 7, 16, 19, 20, 23 and 26) where kept constant given the high local sequence conservation throughout the 234 natural HVR1 variants. Noteworthy also is the total absence of negatively charged residues. With the exception of position 1, where Gln was chosen to represent the His, Glu, Asp, Gln, Asn group, no acidic residues were present within the 80% fraction. Qualitatively, the profile can be described as a generally more variable central region flanked by N-terminal and C-terminal tails containing conserved elements.

Construction of the library proceeded by cloning a degenerated synthetic oligonucleotide as a fusion to the 5' end of the gene coding for the major coat protein (pVIII) in a phagemid vector for M13 display (see Materials and Methods). About $2 \times 10^8$ independent transformants were obtained. To verify the quality and complexity of the library (HVR1 library), the inserts of fifty-six randomly chosen individual clones were sequenced. This analysis led to the following results:

(1) all clones displayed different sequences;
(2) 63% of the clones contained full-length inserts while the remaining ones had small deletions;
(3) none of the sequenced clones encoded for peptides corresponding to known HVR1 from viral isolates, searched on 15 Mar. 1998.

From these data it was inferred that the library has a complexity close to the number of individual transformants.

EXAMPLE 2

Identification of HVR1 Mimotopes Frequently Reacting with HCV Patients' Sera

The more complex and diverse the repertoire of antibodies used for the selection, the higher should be the probability to enrich phage recognised by many different antibodies against HVR1 epitopes. Sera from chronically infected, viremic patients appear to meet these requirements as these individuals have a rather long history of viral persistence, during which a large number of HCV variants have been generated and have challenged the immune system, presumably leading to the accumulation of a highly heterogeneous population of anti-HVR1 antibodies.

Figure 2:
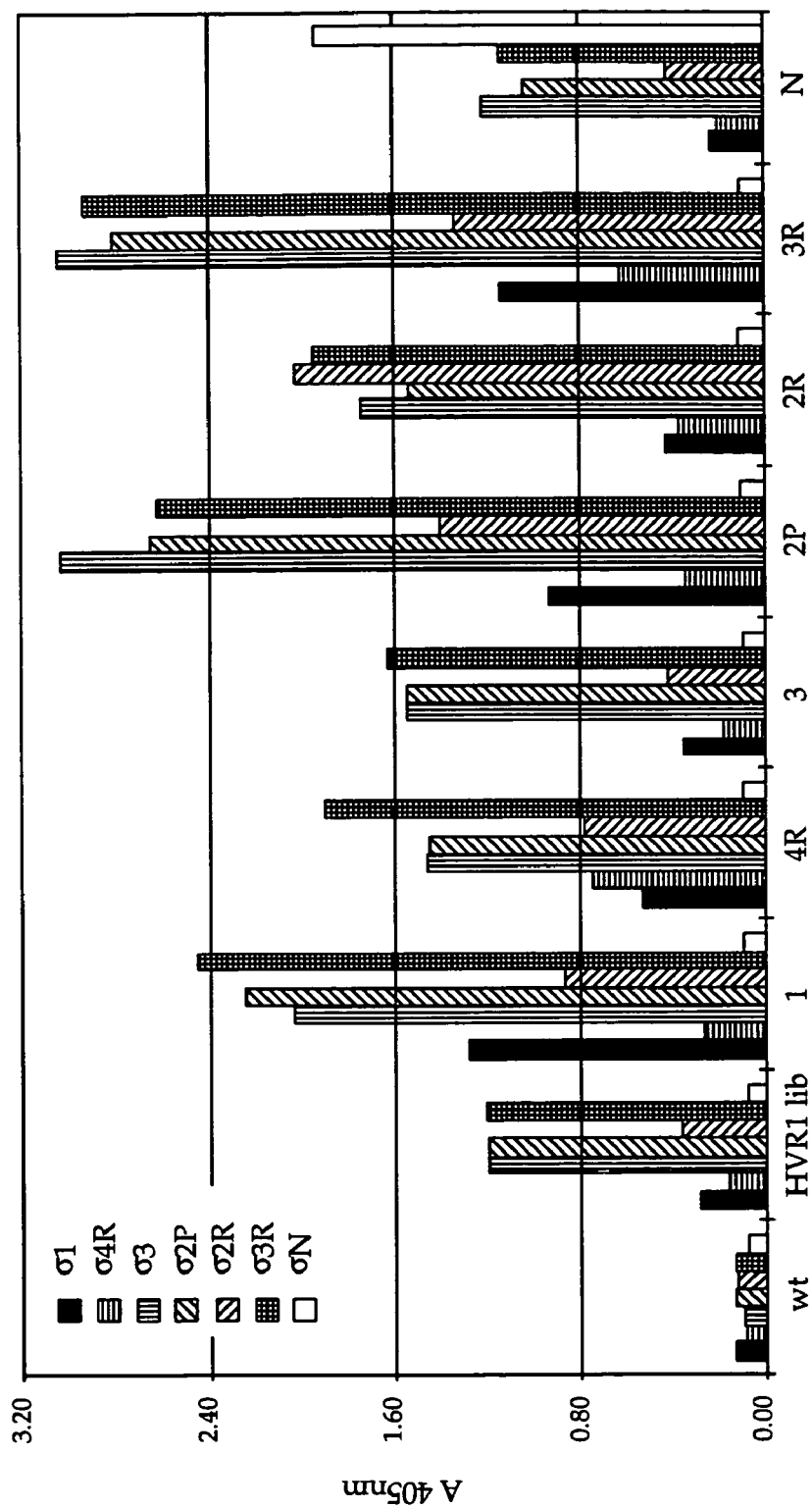

Eight sera from chronic patients infected by viruses of five different genotypes: 1a, 1b, 2a, 2b, 3a (Simmonds et al., 1993) were used to perform six affinity selections of the HVR1 library (Table 1). As control, a serum from a non infected individual was also used. Pools of phage obtained from all seven selections were amplified and tested for their reactivity to each of the selecting sera in ELISA. The results of this experiment showed a significant enrichment of phage recognised by the selector antibodies, as evidenced by the increase in reactivity with respect to the unselected library (FIG. 2). In most cases, phage pools enriched by HCV sera reacted with more than one patient's serum. Peptides recognised by antibodies unrelated to HCV infection were also enriched from the library. In fact, the pool of phage selected with the control serum has a higher reactivity with this serum than the unselected library (FIG. 2). However, patients' sera drove selection toward HCV-related mimotopes as no reactivity to phage pools enriched by HCV sera was detected using sera from healthy individuals (FIG. 2 and data not shown).

To gain insight into the frequency of reactivity of the selected mimotopes with different patients' sera, forty individual clones from two pools (4R and 2R, Table 1) were randomly chosen and tested for their reactivity in ELISA with a panel of twenty sera from HCV infected patients different from those used for the selection. An equivalent number of sera from non-infected healthy controls were used to assess the specificity for anti-HCV antibodies. Twenty-four clones turned out to be HCV-specific. Their distribution as a function of their frequency of reactivity with patients' sera is reported in FIG. 3 (upper panel). Among them, phage reacting with more than one serum were identified; some of these were recognised by up to 55% of the tested sera.

Figure 3:
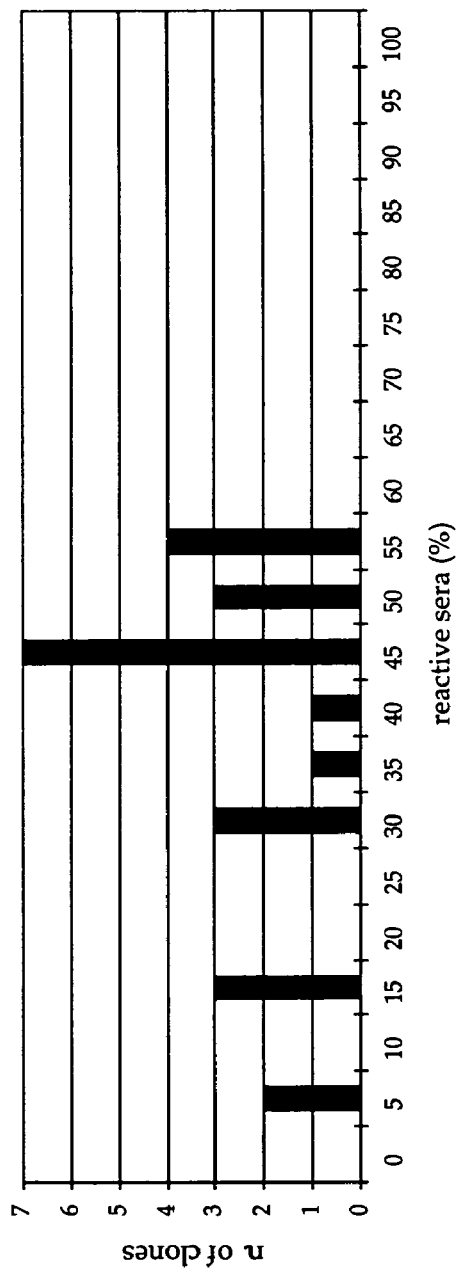
Figure 3:
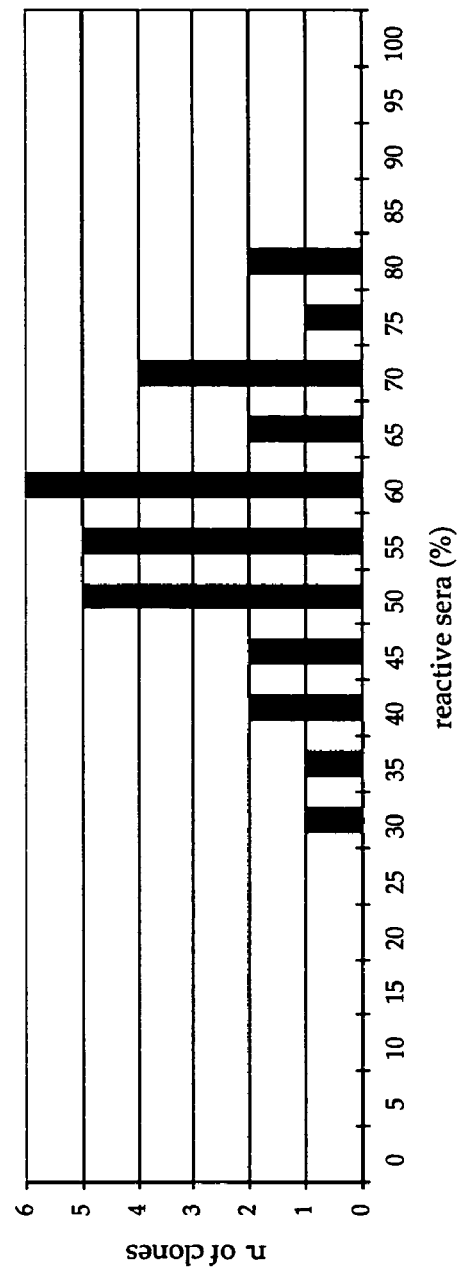

To further improve the isolation of mimotopes reacting with many different anti-HVR1 antibodies, the enriched phage pools were subjected to a second round of affinity selection using patients' sera different from those used for the first round. In this way nine new pools were generated (Table 1) and analysed by ELISA. As before, a general increase in reactivity with the selector antibodies was observed. In addition, all second round phage pools reacted more frequently than those selected in the first round with a panel of sera from HCV-infected patients different from those used for either selection, reflecting a higher recognition frequency of the isolated peptides. This was confirmed by comparing the reactivity with HCV sera of clones randomly chosen among those eluted after one round of affinity selection (FIG. 3, upper panel) and those obtained by re-selecting them with a second different serum (FIG. 3, lower panel). Not only the frequency, but also the distribution of reactivity appeared to be significantly different after the second selection step. While recognition of phage from the first selection appears to be rather scattered, clones isolated through two rounds of selection show a bell-shaped distribution of their frequency of reactivity with an average value of 60% (FIG. 3, lower panel), indicating that the whole phage population had indeed acquired more of the desired binding properties. It was decided to omit additional selection cycles to avoid introduction of a bias toward biologically favoured phage during amplification.

A total of one hundred and seventy one clones reacting exclusively with HCV sera were identified by screening all second-round pools. Their distribution as a function of the recognition frequency by HCV sera mirrored that of the subset displayed in FIG. 3, lower panel, with the best clones reacting with 80% of the tested samples. More importantly, the profiles of reactivity of the selected mimotopes highlight another relevant feature. Despite their quantitative similar overall frequency of recognition by the HCV sera, different clones display a characteristic pattern of reactivity with the net result that few mimotopes can score for the presence of anti-HVR1 antibodies in all tested sera (FIG. 4A).

Next, it was verified whether the observed high frequency of recognition by HCV sera was limited to the tested patients' population or whether it reflected an intrinsic property of the selected mimotopes. For this purpose another set of sera from infected patients was assayed by ELISA revealing that both the frequency of reactivity of each individual phage and the total coverage of the sera remained unaltered (FIG. 4B).

HCV infected individuals who have resolved the infection most likely came in contact with a lower number of viral variants and presumably developed a narrower spectrum of variant-specific anti-HVR1 antibodies than chronically infected patients. This is supported by the finding that sera from the former population react with synthetic peptides reproducing the HVR1 of natural isolates much more rarely than those of chronically infected viremic patients (Scarselli et al., 1995). Therefore, non viremic sera could constitute a better and more stringent test for assaying the cross-reactivity of HVR1 mimotopes with different anti-HVR1 antibodies. Some of the selected mimotopes were thus tested against forty-one samples from HCV seropositive individuals who were repeatedly found negative for the presence of viral RNA in the blood. Again, the mimotopes reacted with many of these sera albeit at a lower frequency than that observed with sera from viremic patients (compare FIGS. 4(A), 4(B) and 4(C)). These data provide an indication of the ability of the selected mimotopes to cross-react with a large number of different anti-HVR1 antibodies.

EXAMPLE 3

Determination of a Relationship between the Sequence of the Selected HVR1 Mimotopes and their Frequency of Reactivity with HCV Sera The inventors wished to verify whether the amino acid sequence of the selected clones correlates with their frequency of reactivity. No obvious pattern arises from a visual comparison of the sequences so it was decided to analyse separately the sequence patterns of the least and most frequently reacting clones.

Defined as "weak" were the 24 clones that only reacted with less than 3 sera and defined as "strong" were the 27 reacting with more than 11 sera. The amino acid frequencies at each position of weak and strong clones are listed in the Materials and Methods section below, and in Table II.

There is a clear trend for some positions to be occupied by different amino acids in the sets of weak and strong clones and this allowed us to heuristically define a position-based scoring system described in Materials and Methods (see below). The higher is the score of a clone (S-score) the more similar its sequence is to those of the strong clones and the more different from those of the weak ones. As shown in FIG. 5, the S-score correlates reasonably well (correlation coefficient=0.75) with the experimentally determined frequency of reactivity of each clone. It should be emphasised that the S-score was calculated using only the sequences of the "weak" and "strong" clones (51 out of 171), but it correlates well with the frequency of reactivity of all clones. Interestingly, a nearly identical result (correlation coefficient=0.72) can be obtained using only 6 positions where the residue preference of the weak and strong mimotopes differ most (positions 3, 11, 18, 21, 22, 24).

EXAMPLE 4

The HVR1 Mimotopes Antigenicallly Mimic a Large Number of HVR1 Variants from HCV Isolates The inventors set to measure the cross-reactivity of human antibodies which recognise the mimotopes, with sequences representing naturally occurring HVR1.

For this purpose the mimotopes were used as immunoadsorbents to purify the specific antibodies from the bulk of anti-HVR1 present in infected patients' sera. Mimotopes R9, F78, M122, R6, B14, G31, H1 and D6 (FIG. 7) were chosen for these experiments because they were among those which displayed the highest frequency of reactivity with the HCV sera. Mimotope N5 which was recognised by a significantly lower percentage of HCV sera than the average "good" mimotopes (35% and 60–80%, respectively) was also used.

Although some lymphocyte cell lines have been shown to support limited replication of HCV (Shimizu et al., 1992), these systems are not suited for viral propagation and for a detailed study of the cross-reactivity of anti-HVR1 antibodies. Therefore, the cross-reactivity of the immunopurified antibodies on a panel of synthetic peptides reproducing natural HVR1 variants which approximately cover the observed sequence variability was determined.

To this end, a multi-dimensional cluster analysis (Casari et al., 1995) was performed on the same set of 234 aligned natural HVR1 sequences used for the construction of the library. Out of these, forty-three sequences nearly homogeneously distributed over the HVR1 "sequence space" were chosen (see Materials and Methods below) and synthesised as multiple antigenic peptides (MAP; Tam, J. P, 1988; Pessi et al., 1990). A pool of eight sera from infected patients collectively reacting with the entire panel of forty-three MAPs was used as a source of antibodies. The immunopurified antibodies displayed the same reactivity to the mimotope used for the purification compared to the total serum. In contrast, no reactivity to a recombinant HCV core antigen or to the antigens included in a commercially available kit (see below in Materials and Methods) was retained after purification thus testifying to the efficiency and the specificity of the purification.

All immunopurified antibodies reacted with a significant number of natural HVR1 sequences with mimotope R9 yielding antibodies cross-reacting with 79% of natural HVR1 (FIG. 6). As most immunopurified antibodies also displayed some non-overlapping reactivities to the natural sequences, an even higher level of overall cross-reactivity (88%) can be reached by adding up the individual contributions of antibodies purified from only three different mimotopes (R9, F78 and M122, FIG. 6). From these data it was concluded that a limited set of HVR1 mimotopes can antigenically mimic a large number of natural HCV HVR1 variants.

Antibodies immunopurified by mimotopes with higher S-score, and consequently with a higher frequency of reactivity, also showed to be more cross-reactive. Eight mimotopes were used and, as shown in FIG. 7B, the correlation between this sequence related score and the cross-reactivity of the corresponding antibodies is very good (r=0.86; FIG. 7B).

EXAMPLE 5

The HVR1 Mimotopes Induce Antibodies Recognising many Natural HVR1 Variants

A problem prior to the present work was the generation of immunogens able to induce antibodies cross-reacting with the largest number of HCV HVR1 natural variants. The immunogenic potential of some of the best HVR1 mimotopes (R9, F78, M122, G31, H1 and D6) was investigated by injecting them in mice both as whole purified phage and, outside of the original context in which they were selected, as MAPs.

MAPs turned out to be much more potent immunogens presumably due to the insufficient loading of HVR1 peptides on each phage as indicated by mass spectrometry analysis (less than 1% of the total pVIII content). Some variability in the efficiency of immunization was observed between the mimotopes as shown by the difference in titre, with F78 being able to induce antibody titres higher than 1/100,000 as measured by ELISA on the same peptide used for the immunisation (FIG. 8A). Anti-HVR1 mimotope sera were then tested for their ability to recognise heterologous HVR1 variants by ELISA on the panel of forty-three MAPs reproducing HCV sequences from natural isolates. Most of these MAPs were recognised by the immune sera (FIG. 8A), while no reactivity was observed on unrelated control peptides.

The cross-reactivities of the sera of mice immunised with mimotopes did not rank as that of human antibodies immunopurified with the same mimotopes. However, mimotope N5, which showed significantly lower levels of reactivity in both types of assays, revealed to be a much less efficient immunogen, leading to an anti-HVR1 response able to recognize only a minority of the natural HVR1 sequences (FIG. 8A).

The extent of cross-reactivity of the immune sera generally reflects the immunogenicity of the individual MAPs as, in most cases, a higher titer corresponds to a higher level of cross-reactivity (FIG. 8A). Nevertheless, titer alone cannot always explain the difference in cross-reactivity and in the pattern of reactivity displayed by the mimotope induced sera as clearly shown in the case of the anti-G31 serum which has a lower titer than the anti-F78, but reacts with a larger number of natural HVR1 peptides. Similarly, the anti-D6 serum displays the same level of cross-reactivity of the anti-R9 despite a three fold lower titer (FIG. 8A).

The pattern of reactivity displayed by each antiserum is only partially overlapping with that of the others, and, in some cases, unique reactivities were observed. As a consequence of this feature of the induced sera, by adding up all the reactivities, almost all natural HVR1 peptides are recognized (91%, FIG. 8A). This observation is a significant improvement toward the goal of generating broadly reacting antibodies, provided one can obtain a similar increase in cross-reactivity a single immunization with a cocktail of mimotopes. Therefore, three groups of Balb/c mice were immunised with mixtures of mimotopes. Mixture 1 contained mimotopes R9, F78, H1 and D6; mixture 2 was composed of mimotopes M122, and G31, while mixture 3 comprised all six mimotopes. All three mixtures were immunogenic, and induced highly cross-reactive antisera (FIG. 8B). Each of the three antisera displayed the same or an even higher cross-reactivity than that measured by adding up the reactivities of the antisera induced by each of the mimotopes included in the mixture (84% vs 84% for MIX1, 84% vs 81% for MIX2 and 95% vs 91% for MIX3, FIG. 8B). The titers of these sera although high, were not better than those obtained with individual MAPs. It was therefore concluded that the ability of inducing highly cross-reacting response is not simply a consequence of the efficiency of the immunisation.

Materials and Methods

Human Sera

Human sera from HCV-infected patients and from healthy individuals were characterised for the presence of antibodies to HCV by a second-generation HCV ELISA test system (Ortho-HCV ELISA, Ortho Diagnostic Systems, Bersee, Belgium) and by a first generation dot blot immunoassay (RIBA-HCV test, Chiron Co., Emeryville, Calif.). The presence of HCV RNA was detected by nested reverse transcription-PCR using conserved primers localised in the 5' non-coding region of the viral genome and total RNA extracted from 100 µl of serum as previously described (Silini et al., 1995).

Construction of the HVR1 Library

To back-translate the consensus profile described above with reference to FIG. 1B into the corresponding nucleotide sequence, the E. coli codon usage table was employed selecting codons most frequent in highly expressed genes. To facilitate insertion of the library into the phagemid vector two additional constant sequences containing the recognition sites for the restriction enzymes PacI and NotI were added 5' and 3' to the 81 bp segment, respectively giving a total of 116 bp. Absence of NotI and PacI restriction sites in the backtranslation of the consensus profile was verified by computer-assisted sequence analysis. For the chemical synthesis a codon-based "split-and-pool" method (Cormack et al., 1993) was applied in order to keep both library composition and complexity at the desired level. The 116 bp oligonucleotides were amplified with primers complementary to the flanking constant sequences in a 9600 DNA Thermal Cycler (Perkin-Elmer Cetus, Foster City Calif.). The PCR product was digested with PacI and NotI enzymes and gel-purified. The recovered DNA fragment was cloned between the PacI and NotI sites of the pe18PN phagemid vector (a derivative of pc89; Felici et al., 1991) downstream of the pe1B secretion leader and upstream of the entire gene VIII coding sequence. Recombinant phagemids were electroporated into DH10B competent cells. Since DH10B cells cannot be infected by filamentous phage and do not allow for blue/white selection, transformed cells were collected and plasmid DNA was prepared. This DNA was used to transform by electroporation XL1-blue competent cells. Ampicillin resistant colonies were scraped from the plates and resuspended in LB/100 µg ampicillin/ml and 10% (v/v) glycerol. A portion of this bacterial suspension was inoculated into six liters of LB medium containing 100 µg ampicillin/ml at 0.05 $O.D._{600\,nm}$ and grown with vigorous shaking until 0.25 $O.D._{600\,nm}$ was reached. The culture was then superinfected with M13K07 helper phage and grown for additional five hours to obtain the phage particles in the supernatant. The phage were precipitated twice with polyethylene glycol and purified by equilibrium centrifugation in CsCl as described (Felici et al., 1991).

DNA-sequencing was performed as described (Bartoli et al., 1996) using an Applied Biosystem 373 DNA sequencer.

Library Affinity Selection

ELISA multiwell plates (Nunc Maxisorp, Roskilde, Denmark) were coated overnight at 4° C. with 0.5 µg/ml of anti-human (Fc-specific) polyclonal Ab (Immunopure goat anti-human IgG Fc-specific; Pierce, Rockford, Ill.) in 50 mM $NaHCO_3$ pH 9.6. The plates were washed with PBS/ 0.1% Tween 20 (washing buffer) and incubated for 1 hr at 37° C. with 100 µl/well of blocking buffer (5% non fat dry milk, PBS/0.05% Tween 20). 1 µl of human serum diluted 1:100 in PBS/0.1% BSA was added to each well and incubated overnight at 4° C. After washing, $10^{12}$ particles of U.V. killed M13K07 diluted in PBS/0.1% Tween 20, 0.01% BSA, were then added to each well and incubated for 4 h at 4° C. After this pre-incubation, $10^{12}$ particles/well of HVR1 library were added and incubated overnight at 4° C. Unbound phage were removed and several rounds of washing were performed. Bound phage were eluted with 200 µl of elution buffer (0.1M HCl adjusted to pH 2.5 with glycine, 1 mg/ml BSA) and neutralised with 2M Tris-HCl pH 9. Eluted phage were titrated by infection of XL1-blue bacteria and the percentage of clones containing a productive insert was determined by plating infected bacteria on X-gal/IPTG indicator plates (Felici et al., 1991). After amplification (see above) enriched phage were subjected to a second cycle of affinity selection following the same procedure.

Sequence Analysis of the Mimotopes and Definition of the S-Score

Out of a total of 193 selected clones, 171 showed no point mutation (with respect to the original library design) or deletions and were divided in three classes: 24 weak clones (reacting with less than 3 out of the 20 tested sera), 27 strong clones (reacting with at least 12 sera) and intermediate (the remaining clones).

For each amino acid at position i of a 27-mer amino acid sequence, we call Fs(i, aa) and Fw(i, aa) the observed frequency of the same amino acid in position i of the set of strong and weak clones, respectively.

The frequency values are shown in Table II.

S-score(i) was then defined as the difference between the square roots of Fs(i,aa) and Fw(i,aa). The sum over the all 27-mer sequence of S-score(i) is our sequence based S-score. In practice:

$$S\text{-score}=\Sigma_i(\sqrt{Fs(i,aa)}-\sqrt{Fw(i,aa)})$$

where aa is the observed amino acid in position i of the sequence for which the S-score is calculated. The square root of the frequencies was used to amplify differences. For clones where a point mutation or deletion had occurred, the corresponding position was omitted in the score calculation.

Selection of a Representative Set of Natural HVR1 Sequences

The NS1 HVR1 sequence from the HCV BK strain (residues 384–411) was used to search various databases (on 13 Dec. 1995), both protein (SwissProt, PIR and Genpept, the latter representing assigned open reading frames from Genbank and EMBL) and nucleotide sequence (EMBL, Genbank and EST). Duplicated and incomplete sequences were removed from the list of matching sequences to obtain a unique set of 234 natural HVR1 sequences.

Principle component analysis was used to select 40 sequences homogeneously distributed over the set. First, all pairwise distances between the 234 sequences were calculated using the first six eigenvalues calculated using Sequencespace (Casari et al., 1995). Sequences with the smallest distances to neighbouring sequences were eliminated in a stepwise procedure until only 40 sequences remained. Projections into two dimensions along all possible pairs of Eigenvectors showed that the set of 40 sequences did not cluster and were homogenously distributed.

Accession numbers and sequences are:

```
 1 Genbank:D12967   QTRTVGGQMGHGVRGLTSLFSAGSARN  bp   46-bp  126 (SEQ ID NO: 150)

2 PIR:PC1193       STHVTGALQGRAAYGITSFLSHGPSQK  aa   16-aa   42 (SEQ ID NO: 151)

3 Genbank:D00574   HTRVTGGVQGHVTSTLTSLFRPGASQK  bp 1240-bp 1320 (SEQ ID NO: 152)

4 Genbank:L19383   ETHTSGGSVARAAFGLTSIFSPGAKQN  bp   46-bp  126 (SEQ ID NO: 153)

5 Genbank:M62381   ETHVTGGSAGRTTAGLVGLLTPGAKQN  bp 1426-bp 1506 (SEQ ID NO: 154)

6 Genbank:U24616   ATYTTGGSAAKTAHRLASFFTVGPKQD  bp   22-bp  102 (SEQ ID NO: 155)

7 PIR:C48776       DTHVVGGATERTAYSLTGLFTAGPKQN  aa   13-aa   39 (SEQ ID NO: 156)

8 Genbank:U24607   GTTCQGGVYARGAGGIASLFSVGANQK  bp   22-bp  102 (SEQ ID NO: 157)

9 PIR:D48766       RTLSFGGLPGHTTHGFASLSAPGAKQN  aa   13-aa   39 (SEQ ID NO: 158)

10 Genbank:X60573   RTILMAGRQAEVTQSFPGLFSLAPSQK  bp   46-bp  126 (SEQ ID NO: 159)

11 Genbank:D43650   NTHAMGGVVARSAYRITSFLSPGAAQN  bp    1-bp   81 (SEQ ID NO: 160)

12 PIR:PQ0835       STRITGGSMARDVYRFTGFFARGPSQN  aa    6-aa   32 (SEQ ID NO: 161)

13*Genbank:S73387  GTHTIGGSQAQQANRFVSMFSRGPSQK  aa  190-aa  216 (SEQ ID NO: 162)

14 Genbank:D10934   NTYVTGGAAARGASGITSLFSRGPSQK  bp 1491-bp 1571 (SEQ ID NO: 163)

15 Genbank:D31972   NTYASGGAVGHQTASFVRLLAPGPQQN  bp 1409-bp 1489 (SEQ ID NO: 164)

16 Genbank:U14231   ETHTTGGEAARTTLGIASLFTSGANQK  bp  103-bp  183 (SEQ ID NO: 165)

17 Genbank:U24602   ETHTTGGSAARATFGIANFFTPGAKQN  bp   22-bp  102 (SEQ ID NO: 166)

18 Genbank:L19380   ETYTSGGSAAHTTSGFVSFFSPGAKQN  bp   46-bp  126 (SEQ ID NO: 167)

19 Genbank:M74888   GTTRVGGAAARTTSSFASLLTHGPSQN  bp 1147-bp 1227 (SEQ ID NO: 168)

20 Genbank:L12354   NTHTVGAAASRSTAGLTSLFSIGRSQK  bp 1468-bp 1548 (SEQ ID NO: 169)

21 Genbank:X79672   NTRVTGGVQSRTTGTFVGLFTPGPSQR  bp    1-bp   81 (SEQ ID NO: 170)

22 PIR:A48776       NTHVSGGRVGHTTRSLTSFFTPGPQQK  aa   13-aa   39 (SEQ ID NO: 171)

23 Genbank:D12952   STRVSGGQQGRAAHSLTSLFTLGASQN  bp   46-bp  126 (SEQ ID NO: 172)

24 Genbank:D16566   STRITAQAEGRGASTLTSLFTSGASQK  bp    8-bp   88 (SEQ ID NO: 173)

25 Genbank:M84754   STIVSGGTVARTTHSLASLFTQGASQK  bp 1491-bp 1571 (SEQ ID NO: 174)

26 Genbank:D14853   ETRVTGGAAGHTAFGFASFLAPGAKQK  bp 1491-bp 1571 (SEQ ID NO: 175)

27 Genbank:S24080   NTYVTGGSAGRAVAGFAGLLQPGAKQN  bp   46-bp  126 (SEQ ID NO: 176)

28 Genbank:S35631   ETHSVGGSAAHTTSRFTSLFSPGPQQN  bp  580-bp  660 (SEQ ID NO: 177)

29 Genbank:S62395   ETHVTGGSAASTTSTLTKLFMPGASQN  bp   43-bp  123 (SEQ ID NO: 178)

30 Genbank:S70291   QTRTVGGANARNTYGLTTLFTTGPKQN  bp    1-bp   81 (SEQ ID NO: 179)

31 Genbank:D88472   GTTTVGSAVSSTTYRFAGMFSQGAQQN  bp 1485-bp 1565 (SEQ ID NO: 180)

32 Genbank:D10687   NTHTVGGTEGFATQRLTSLFALGPSQK  bp 1180-bp 1260 (SEQ ID NO: 181)

33 Genbank:D43651   NTHVTGGVVARNAYRITTFLNPGPAQN  bp   39-bp  119 (SEQ ID NO: 182)

34 Genbank:D14305   HTYTTGGTASRHTQAFAGLFDIGPQQK  bp 1427-bp 1507 (SEQ ID NO: 183)

35 Genbank:X60590   KTHVTGMVAGKNAHTLSSIFTSGPSQN  bp   46-bp  126 (SEQ ID NO: 184)

36 Genbank:D30613   GTHVTGGKVAYTTQGFTSFFSRGPSQK  bp 1491-bp 1571 (SEQ ID NO: 185)

37 Genbank:X53131   ETYTSGGNAGHTMTGIVRFFAPGPKQN  bp  802-bp  882 (SEQ ID NO: 186)

38 Genbank:U24619   STYSMGGAAAHNARGLTSLFSSGASQR  bp   22-bp  102 (SEQ ID NO: 187)
```

```
-continued
39 Genbank:M62382  ETHVTGGSAGRSVLGIASFLTRGPKQN  bp1426-bp1506 (SEQ ID NO: 188)

40 Genbank:D88474  ETYIIGAATGRTTAGLTSLFSSGSQQN  bp1488-bp1568 (SEQ ID NO: 189)

*Sequence 13 corresponds to the translated amino acid sequence
(aa190-aa216) reported in the CDS feature of Genbank entry S73387.
```

*Sequence 13 corresponds to the translated amino acid sequence (aa190–aa216) reported in the CDS feature of Genbank entry S73387.

Three additional sequences were also synthesized as MAPS: Two sequences are derived from the pedigreed HCV inoculum H77 (FIG. 2 of Farci et al., 1994):

```
41 (H77-1)  ETHVTGGNAGRTTAGLVGLLTPGAKQN  bp1-bp81 (SEQ ID NO: 190)

42 (H79)    ETHVTGGSAGHTAAGIASFFAPGPKQN  bp1-bp81 (SEQ ID NO: 191)
``` and one from the major isolate of a patient whose immunoreaction has been characterized (Scarselli et al., 1995):

```
43 Genbank:X79669  NTRVTGGVQSHTTRGFVGMFSLGPSQR  bp1-bp81 (SEQ ID NO: 192)
```

Phage Preparation and ELISA

Phage supernatants were prepared from XL-1 blue infected cells as previously described (Folgori et al. 1994). ELISA were performed according to Dente et al., (1994) using 25 µl of phage supernatant/well. Sera were diluted 1:100 if not otherwise specified and revealed by addition of species-specific anti-IgG (Fc-specific) alkaline phosphatase-conjugated secondary antibodies (Sigma A-9544; dilution 1:5000 in ELISA blocking buffer). Results were recorded as differences between $O.D._{405\ nm}$ and $O.D._{620\ nm}$ by an automated ELISA reader (Labsystems Multiskan Bichromatic, Helsinki, Finland).

ELISA with phage pools were performed in the same way by using equivalent amounts ($10^{10}$ ampicillin transducing units) of amplified phage after CsCl purification (see above). 100 µl of MAPs representing natural HVR1 sequences were used to coat ELISA plates (Nunc Maxisorp, Roskilde, Denmark) at a final concentration of 10 µg/ml in coating buffer (50 mM $NaHCO_3$ pH 9.6). After blocking of free binding sites, 100 µl/well of sera or affinity-purified antibodies were added. Mouse and rabbit sera were tested at final 1:100 dilution in blocking buffer; affinity purified antibodies were tested at final concentration of 150 ng/ml. Plates were incubated overnight at 4° C. After washing, 100 µl/well of alkaline phosphatase conjugated secondary antibodies (goat anti-mouse IgG Sigma A-7434 diluted 1:2000; goat anti rabbit IgG Sigma A-8025 diluted 1:5000; goat anti human IgG Sigma A-9544 diluted 1:5000) were added and incubated one hour at room temperature. Plates were washed and alkaline phosphatase revealed as described above.

Affinity Purification of Antibodies from Human Sera

Multiple antigenic peptides reproducing the sequence of different mimotopes were used since they showed the same binding profile with HCV sera in ELISA as the phage, but proved to be more efficient in the affinity selection of the antibodies. Activated CH Sepharose 4B column (Pharmacia Biotech 17–0490-01) was coupled with the MAP of interest at the ratio of 1 g of dried Sepharose/1 mg of MAP in coupling buffer (0.1 M $NaHCO_3$ pH8/0.5M NaCl). Coupling was followed by blocking of free amino-groups with 0.1M Tris-HCl pH8. Sample was loaded as a pool of eight HCV sera diluted 1:5 in coupling buffer. After adsorption at room temperature and extensive washing with PBS, bound antibodies were eluted with 0.1M glycine-HCl pH 2.7 supplemented with BSA at final concentration of 10 µg/ml and immediately neutralised by 2M Tris-HCl pH9.4. The concentration of eluted antibodies was determined by ELISA using as standard human IgG (Sigma I- 2511). Affinity-purified antibodies were checked for their reactivity in ELISA with the mimotope used for the purification (both in the form of MAP and phage) and, as control, with HCV-unrelated MAPs. The specificity of the purification was further confirmed by testing the eluted antibodies by ELISA on recombinant bacterially expressed HCV core protein (Prezzi et al., 1996) and by the second-generation HCV ELISA test (Ortho Diagnostic Systems, Bersee, Belgium). The total amounts of immunoglobulins recovered in each affinity purification from a standard amount of 1 ml of serum pool were comparable, ranging from 0.8 to 1.5 µg. For ELISA on the test MAPs the concentration was adjusted in every case to 150 ng/ml.

Animal Immunisations

Immunising phage were prepared from XL1-blue infected cells and CsCl purified as previously described (Felici et al., 1991). Three to five weeks old female BALB/C mice (Charles River, Como, Italy) were immunised by intraperitoneal injection of 100 µl of antigen solution at day 0, 21 and 42 and bled at day 52 (third bleed) and day 148 (fourth bleed). Phage were injected as 0.9% NaCl suspensions at a concentration of about 0.3 mg/ml ($2.5 \times 10^{13}$ phage particles/ml) without added adjuvant.

For peptide immunisations, MAPs were dissolved in PBS at a final total concentration of 400 µg/ml and injected as a 1:2 dilution in either Complete Freund's Adjuvant (first injection) or Incomplete Freund's Adjuvant (booster injections). Four to seven weeks old female Balb/c mice (Charles River, Como, Italy) were immunised by i.p. injection of 100 µl of antigen solution at weeks 0, 3 and 6 and bled at days 0 (pre-bleed) and 10 days after each additional injection. When more than one peptide were used for the immunization, equal amounts of each mimotope were mixed, and 100 µl of a 400 µg/ml solution was used.

EXAMPLE 6

Immunogenic Properties of Peptides and E2 Recombinant Proteins. DNA Immunisation In Vivo Immunogenic properties of some of the selected HVR1 mimotopes were explored either alone or as N-terminal fusion to the ectodomain of the E2 protein.

The hcv E2 peptide is generally identified by the peptide spanning from amino acid 384 to amino acid 809 of the HCV polyprotein. The HVR1 region is generally identified as amino acid 384 to 410. In the following examples ΔE2 identifies peptides corresponding to aa411 to aa683 of the HCV polyprotein.

Construction of Recombinant Plasmids

Three types of plasmids were produced and their structure is reported in FIG. 9:

(i) pΔE2—directing the synthesis of an E2 protein fragment (HCV strain N, Nishihara et al.; Gene; 1993; 129 pp 207–214; from aa411 to aa683 of the HCV polyprotein) carrying a deletion of both the HVR1 and the C-terminal hydrophobic region;

(ii) a second plasmid pF78 expressing one of the HVR1 mimotopes;

(iii) a set of 11 constructs (pMimoE2) in which DNA sequences encoding for the eleven different HVR1 mimotopes were fused at the 5' end of the ΔE2 coding sequence in the plasmid pΔE2. All recombinants were cloned in frame downstream of the tissue plasminogen activator (TPA) signal sequence to enforce secretion of the antigen.

ΔE2 gene (therefore coding for the peptides spanning from aa 411 to aa 683) was cloned using as PCR template an E2 N strain containing vector (Nishihara et al.; Gene; 1993; 129 pp 207–214). A PCR fragment was obtained using synthetic oligonucleotide primers:(oligo fwd=GCGAGATCTTAATTAACGATATCCAGCTTATAAAC (SEQ ID NO: 193); oligo rev=TCCGGATCCTTAGTGGTGGTGGTGGTGGTGCGGTAG (SEQ ID NO: 194)).

By the use of these primers the resulting PCR product comprises, besides the ΔE2 gene, BglII, PacI and EcoRV restriction sites at the 5' end, and a sequence coding for six histidine residues (His tag), and a TAA termination codon followed by BamHI restriction site at the 3' end. This PCR product is than digested with BglII and BamHI and ligated at the BglII site of V1JnsTPA vector (J. J. Donnelly et al. The Journal of Infect. Diseases; 1996; 713; pp314–320) in frame with TPA leader sequence to obtain the plasmid V1JnsTPA-ΔE2 (designated pΔE2 in FIG. 9).

HVR1 mimotope sequences were subcloned at the 5' end of ΔE2 gene in pΔE2. HVR1 fragments were PCR-amplified directly from selected phage supernatant. The 5' primer contained PacI restriction site and was complementary to a 5' sequence (GGCGGCCGTTTAATTAAC; SEQ ID NO: 195) which is a constant part of HVR1 mimotope sequences; the 3' primers were complementary to the last 15 nucleotides and were different according to the mimotope sequence cloned. PCR-amplified fragments were PacI digested and ligated into pΔE2 plasmid. A total number of 11 pMimoE2 (FIG. 9) plasmids were generated.

Furthermore a pF78 (FIG. 9) pasmid was constructed by PCR amplification of F78 sequence (oligo fwd=GCGAGATCTTAATTAACCAGACCCATACCACC (SEQ ID NO: 196); oligo rev=TCCGGATCCTTAGTGGTGGTGGTGGTGGTTCTGTTTCGCGCC (SEQ ID NO: 197)) and cloning at the BglII site of V1JnsTPA vector. Large-scale DNA preparations were performed using Qiagen 2500-Tip columns, following manufacturer's instructions (Qiagen, Hilden, Germany).

Characterisation of Mimotope/E2 Recombinant Proteins

The ability of pF78, pΔE2 and pMimoE2 plasmids to drive the expression of recombinant proteins in a mammalian system was assessed by transient transfection of 293 cells. pΔE2 and pMimoE2 transfected cells showed a strong and specific staining when probed with an anti-E2 monoclonal antibody (mAb-185) recognising an epitope located downstream of the HVR1. Also mF78 expression was demonstrated by immunocytochemistry of transfected 293 cells using a mice antiserum obtained by immunisation with a MAP reproducing the amino acid sequence of mimotope F78. These data were confirmed by ELISA on whole cell extracts from transfected cells. Significant amounts of all recombinant proteins were also secreted in the medium as measured by ELISA on cell culture supernatants from transfected cells.

Both intracellular and secreted proteins were heterogeneously glycosylated as suggested by their appearance as a cluster of slow migrating bands in SDS PAGE. The higher molecular weight displayed by the extracellular protein fraction is indicative of a different extent of glycosylation and confirms that the protein is actively secreted and not simply released by lysed cells. In both cases, endoglycosydase treatment leads to an increase of the migration rate to the one expected from the amino acid composition.

All recombinant mimotope/E2 fusion proteins as well as the ΔE2 mutant were efficiently recognised by two different conformation-sensitive monoclonal antibodies. Furthermore, no cysteine-bridged multimeric aggregate was visible by Western blot on non reducing SDS PAGE of either the cellular or the secreted fraction from each clone. Similar results were obtained by transfecting mouse rabdomyosarcoma cells thereby providing indication that efficient expression will be achieved upon in vivo transfection of mouse muscle cells.

Plasmid DNA Immunisation

Four weeks old female Balb/c mice (Charles River, Como, Italy) were used for immunisations. Fully anaesthetised mice received from 100 μg of plasmid DNA dissolved in 100 μl of saline buffer (PBS). Fifty microliters of DNA were injected bilaterally into quadriceps muscle via insulin syringe (B-D, U-100 28G1/2 microfine needle). Mice were given three or four injections at 3-weeks intervals and were bled two weeks after each injection. Sera were analysed for antibody titre and cross-reactivity.

Serology of αΔE2 and α HVR1 Antibodies

ELISA 96 well plates (Immunoplate Maxisorp; Nunc, Roskilde, Denmark) were coated with 1 μg/well GNA (Sigma L8275) in 50 mM $NaHCO_3$ at pH 9.6 and incubated overnight at 4° C. Plates were washed (PBS/0.1% Tween 20) and incubated 1 hr at 37° C. with 250 μl/well of blocking buffer (2% BSA, 1×PBS, 0.1% Tween 20). F78E2 or ΔE2 proteins were produced by transient transfection in 293 cells. 10× concentrated supernatant were used as target antigen in ELISA. Saturating amount of each protein/well were incubated in blocking buffer 3 hrs at RT on GNA-coated plates. Serial dilutions of immune sera (from 1:100 to 1:72900) were pre-incubated for 2 hrs at RT with 1 μl/well of 10× supernatant from mock transfected 293 cells in blocking buffer. Sera incubation was performed o/n at 4° C. After 1 hr at RT of IIAb incubation (α-mouse IgG Fc-specific AP conjugated, SIGMA 7434, diluted 1:2000 in blocking buffer), plates were developed for 30 minutes at 37° C.

Anti HVR1 mimotope antibodies were titrated (dilutions of sera from 1:100 to 1:72900) by ELISA assay using for each serum the homologous peptide sequence in the form of MAP.

In all cases sera titre was defined as the highest serum dilution that resulted in an absorbance value of 0.3 O.D. (almost 6 times the background value).

Cross-Reactivity Assay

Sera were assayed for their cross-reactivity to different HVR1 natural variants using a set of 43 representative MAPS as described in Materials and Methods.

Intramuscular Injection of Mimotope Encoding Constructs Induces a Strong Humoral Response Plasmids pΔE2 and pF78E2 were used to set up the optimal conditions for induction of humoral response. Induction of antibodies against epitopes located outside of the HVR1 was monitored by ELISA using the ΔE2 protein expressed by transiently transfected 293 cells. Balb/C and C57black mice were immunised to test the immunogenicity of the mimotope the number of injections (from one to four) and the amount of injected DNA directly correlated with the magnitude of antibody response. The highest antibody titres against the ΔE2 protein were obtained after three injections at three weeks-intervals using fifty or one hundred micrograms of pΔE2 DNA per mouse. Further injections did not improve titres. A similar kinetic of induction of antibodies against the ΔE2 protein was observed following mice immunisation with plasmid pF78E2. Induction of anti-HVR1 antibodies in this latter group of animals was tested by ELISA on MAPF78. No significant difference was observed between the two strains of mice under investigation as far as the optimal conditions of immunisation are concerned, but C57black mice showed on average better responses.

Antisera from mice immunised with the construct expressing only the F78 HVR1 mimotope (pF78) also induced a specific response, but the titres were much lower than those obtained by using the related pF78E2 construct. Several factors such as the level of expression, the folding of the recombinant products or the presence of stronger T helper epitopes might be responsible for the higher response observed with the fusion constructs as compared to the F78 mimotope alone.

Anti-Mimotope Sera Cross-React with Different Natural HVR1 Variants

The ability of mimotope/E2 fusions to elicit a cross-reactive response by DNA-based immunisation, was evaluated using a panel of forty-three synthetic peptides reproducing the HVR1 sequences of natural isolates as coated antigens in ELISA (see Materials and methods).

In Table III are reported the average titres obtained by immunisation of Balb/c mice (upper panel) and C57Black mice (lower panel) using different individual plasmids or mixtures of plasmids. Crossreactivity is reported as number of peptides scored as positive of the 43 tested.

pB14E2 and pB24E2 plasmids did not induce a cross-reactive immune response, in spite of the presence of significant levels of antibodies specific for a peptide displaying the homologous mimotope sequence in the relative immune sera (Table III). All the other constructs gave rise to anti-sera cross-reacting against some of the natural HVR1 sequences, with the anti-F78 sera being able to recognise up to 28% of the tested peptides (Table III).

The extent of cross-reactivity of the immune sera generally reflected the immunogenicity of the individual plasmids as, in most cases, a higher titre corresponded to a higher level of cross-reactivity (Table III). Nevertheless, titre alone cannot always explain the differences in cross-reactivity, as shown with sera from mice immunised with plasmid pR6E2 which induced lower titres than the pD6E2, pH1E2 and pM63E2 constructs, but reacted with a larger number of natural HVR1 peptides. Similarly, sera from mice immunised with the pF7E2, pM122E2 and pR9E2 showed a cross-reactivity two fold higher than that observed with the pG31E2 immune sera, despite similar titres (Table III).

In C57Black mice injection of the pF78E2 chimaeric gene led to the development of a stronger response with a consequently higher cross-reactivity as compared to Balb/C mice (49% vs 28%).

Immunisation with Mixtures of Plasmids Improves the Cross-Reactivity of the Response Three groups of Balb/C mice were immunised with mixtures of plasmids encoding for mimotope/E2 chimaeras, each mouse receiving a total amount of 100 μg DNA/injection.

Mixture A contained the plasmids encoding for D6, F78, G31, H1, M122 and R6 fusions to E2. Mixture B also included the other three constructs that induced cross-reactive antibodies: pE19E2, pM63E2 and pR9E2, while Mixture C comprised all eleven plasmids. (Mixtures of peptides, and nucleic acid encoding peptides, according to each of Mixture A, Mixture B and Mixture C represent further aspects of the present invention.)

All three mixtures were immunogenic, and induced highly cross-reactive antisera (Table III). Antibodies from animals immunised with Mixture A did not show higher cross-reactivity as compared to those obtained by injecting individual plasmids included in the cocktails. However, it must be emphasised that in the former case titres were about fifty fold lower, suggesting that Mixture A has the potential to induce a more widely cross-reacting response provided efficiency of the immunisation is increased. The results obtained with Mixture B lent further support to this hypothesis. Mice receiving the second mixture of plasmids showed a net increase in cross-reactivity in that they developed anti-sera able to recognise about 50% of the tested natural HVR1 sequences. Also in this case the average titres were one order of magnitude lower than those displayed by the most cross-reacting sera from animals immunised with individual plasmids (Table III).

Intramuscular delivery of the most complex mixture including all plasmids encoding for the mimotope/E2 chimaeras did not further improve the breath of reactivity of the resulting immune sera. This result is consistent with the observed lack of cross-reactivity displayed by the animals immunised with the two additional constructs present in this cocktail (pB14E2 and pB24E2).

Similar data were obtained by immunising C57black mice.

REFERENCES

Alter, H. J. (1995) Blood 85, 1681–1695.
Bartoli, F., et al. (1996) BioTechniques 20 554–558.
Bukh, J., 1995) Seminars in Liver Disease 15, 41–63.
Casari, G., et al. (1995) Nature Structural Biology. 2, 171–178.
Choo, Q. L., et al. (1989) Science 244, 359–362.
Choo, Q. L., et al. (1994) Proc. Natl. Acad. Sci. USA 91, 1294–1298.
Cohen, J, (1993) Science 259: 1691–1692.
Cormack, B. P. and Struhl, K. (1993). Science 262 244–248.
Cortese, R., et al. (1994) Tibtech 12, 262–266.
Cortese, R., et al. (1996) Current Opinions in Biotechnology 7, 616–621.
Dente, L., et al. (1994) Gene 148, 7–13.
Farci, P., et al. (1992) Science 258 135–140.
Farci, P., et al. (1994) Proc. Natl. Acad. Sci. USA 91, 7792–7796.
Farci, P., et al. (1996) Proc. Natl. Acad. Sci. USA 96, 15394–15399.
Felici, F., et al. (1991) J. Mol. Biol. 222, 301–310.
Folgori, A., et al. (1994) EMBO J. 13, 2236–2243.
Fried, M. W. and Hoofnagle, J. H. (1995) Semin. Liver Dis. 15, 82–91.
Kato, N., et al. (1993) J. Virol. 67, 3923–3930.
Kojima, M., et al. (1994) Virology 204, 665–672.
Kurosaki, M., et al. (1994) Virology 205, 161–169.

Major, M. E., et al. (1995) J. Virol. 69, 5798–5805.
Martell, M., et al. (1992) J. Virol. 66, 3225–3229.
Martell, M., et al. (1994) J. Virol. 68, 3425–3436.
Mast, E. E. and Alter, M. J. (1993) Semi. Virol. 4, 273–283.
Mecchia, M., et al. (1996). J. Immunol., 157, 3727–3736.
Meola, A., et al. (1995). J. Immunol. 154, 3162–3172.
Pessi, A., et al. (1990). J. Chem. Soc, Chemical Communications, 1, 8–9.
Prezzi, C., et al. (1996). J. Immunol. 156, 4504–4513.
Scarselli, E., et al. (1995) J. Virol. 69, 4407–4412.
Shimizu, Y. K., et al. (1992) Proc. Natl. Acad. Sci. USA 89, 5477–5481.
Shimizu, Y. K., et al. (1994) J. Virol. 65, 1494–1500.
Shimizu, Y. K., et al. (1997). J. Virol. 71, 5769–5773.
Silini, E., et al. (1995) Hepatology 21, 285–290.
Simmonds, P., et al. (1993). J. Gen. Vir. 74, 2391–2399.
Tam, J. P. (1988) Proc. Natl. Acad. Sci. USA 85:5409–5413.
van Doorn, L., et al. (1995) J. Virol. 69, 773–778.
Weiner, A. J., et al. (1991). Virology 180, 842–848.
Weiner, A. J., et al. (1992). Proc. Natl. Acad. Sci. USA 89 3468–3472.
Weiner, A., et al. (1995). Proc. Natl. Acad. Sci. USA 92, 2755–2759.
Winter, G. and Milstein, C. (1991) Nature 349, 293–299.
Yang, N. S., et al. (1990). Proc. Natl. Acad. Sci. USA 87: 9568–9572.

TABLE 1—Scheme of the Selections.

First and second round of HVR1 library enrichment with sera from HCV infected patients are indicated at the top of the table. Names of the sera and the genotype of the corresponding infecting virus (in brackets) are shown in the left column. In the right column are indicated the names of the resulting phage pools.

TABLE II—Amino Acid Frequencies Observed in the set of "Strong" and "Weak" Crossreactive Mimotopes.

i indicates amino acid position (1 to 27); aa indicates amino acids in standard one letter code; Fs(i,aa) is the frequency in position i of the amino acid aa in the "strong" mimotopes; Fw(i,aa) is the frequency in position i of the amino acid aa in the "weak" mimotopes.

TABLE I

| | Ist selection | | IInd selection | | |
|---|---|---|---|---|---|
| serum/genotype | | phage pool | serum/genotype | | phage pool |
| σ4R | (1b) | 4R | σ2 | (1b) | B |
| σ3R | (3a) | 3R | σ1 | (1a) | D |
| σ3 | (2a) | 3 | σ2 | (1b) | E |
| σ2R | (3a) | 2R | σ3 | (2a) | R |
| σ1 | (1a) | 1 | σ4 | (2a) | F |
| | | | σ2 | (1b) | H |
| σ2P | (2b) | 2P | σ2 | (1b) | G |
| | | | σ1 | (1a) | L |
| | | | σ4 | (2a) | M |
| σN | | N | | | |

TABLE II

| i | aa | Fs (i, aa) | Fw (i, aa) |
|---|---|---|---|
| 1 | Q | 0.70 | 0.64 |
| | T | 0.30 | 0.36 |
| 2 | T | 1.00 | 1.00 |
| 3 | H | 0.52 | 0.28 |
| | T | 0.48 | 0.12 |
| | R | 0.00 | 0.60 |
| 4 | T | 0.70 | 0.52 |
| | V | 0.30 | 0.48 |
| 5 | V | 0.56 | 0.36 |
| | T | 0.44 | 0.64 |
| 6 | G | 1.00 | 1.00 |
| 7 | G | 1.00 | 1.00 |
| 8 | Q | 0.41 | 0.24 |
| | S | 0.30 | 0.56 |
| | V | 0.29 | 0.20 |
| 9 | A | 0.48 | 0.28 |
| | Q | 0.37 | 0.40 |
| | V | 0.15 | 0.32 |
| 10 | S | 0.44 | 0.64 |
| | G | 0.37 | 0.32 |
| | A | 0.19 | 0.04 |
| 11 | H | 0.82 | 0.40 |
| | R | 0.18 | 0.60 |
| 12 | Q | 0.52 | 0.44 |
| | A | 0.26 | 0.20 |
| | T | 0.22 | 0.36 |
| 13 | A | 0.37 | 0.28 |
| | T | 0.33 | 0.52 |
| | V | 0.30 | 0.20 |
| 14 | S | 0.48 | 0.32 |
| | H | 0.41 | 0.32 |
| | R | 0.11 | 0.36 |
| 15 | S | 0.52 | 0.32 |
| | G | 0.41 | 0.24 |
| | R | 0.07 | 0.44 |
| 16 | L | 1.00 | 1.00 |
| 17 | T | 0.78 | 0.52 |
| | V | 0.22 | 0.48 |
| 18 | S | 0.48 | 0.24 |
| | G | 0.45 | 0.36 |
| | R | 0.07 | 0.40 |
| 19 | L | 1.00 | 1.00 |
| 20 | F | 1.00 | 1.00 |
| 21 | S | 1.00 | 0.20 |
| | R | 0.00 | 0.80 |
| 22 | P | 0.89 | 0.32 |
| | L | 0.07 | 0.28 |
| | Q | 0.04 | 0.32 |
| | S | 0.00 | 0.08 |
| 23 | G | 1.00 | 1.00 |
| 24 | A | 0.41 | 0.04 |
| | S | 0.37 | 0.20 |
| | P | 0.22 | 0.76 |
| 25 | K | 0.41 | 0.32 |
| | S | 0.41 | 0.36 |
| | Q | 0.18 | 0.32 |
| 26 | Q | 1.00 | 1.00 |
| 27 | N | 0.67 | 0.52 |
| | K | 0.33 | 0.48 |

TABLE III

| plasmid | titre | n. positive peptides |
|---|---|---|
| pB14E2 | 270 | 0 |
| pB24E2 | 189 | 0 |
| pD6E2 | 4222 | 3 |

TABLE III-continued

| plasmid | titre | n. positive peptides |
|---|---|---|
| pE19E2 | 990 | 2 |
| pF78E2 | 31812 | 12 |
| pG31E2 | 31251 | 5 |
| pH1E2 | 2977 | 1 |
| pM63E2 | 3888 | 2 |
| pM122E2 | 41360 | 10 |
| pR6E2 | 1923 | 6 |
| pR9E2 | 21092 | 11 |

TABLE III-continued

| plasmid | titre | n. positive peptides |
|---|---|---|
| mF78 | 110 | 2 |
| MIX | 684 | 11 |
| MIX | 1224 | 19 |
| MIX | 610 | 18 |
| pF78E2 | 41547 | 21 |
| MIX | 20381 | 24 |

What is claimed is:

1. A peptide comprising an amino sequence provided by Formula II (SEQ ID NO: 39):

Q T X$^1$ T V G G Q A S X$^2$ Q A S S L T X$^3$ L F S X$^4$ G X$^5$ K Q N, wherein X$^1$ is either H or T;
X$^2$ is either H or R;
X$^3$ is either S, G, or R;
X$^4$ is either P, L or Q; and
X$^5$ is either A, S, or P.

2. A peptide comprising an amino sequence provided by Formula I (SEQ ID NO: 1):

X$^1$ T X$^2$ X$^3$ X$^4$ G G X$^5$ X$^6$ X$^7$ X$^8$ X$^9$ X$^{10}$ X$^{11}$ X$^{12}$ L X$^{13}$ X$^{14}$ L F X$^{15}$ X$^{16}$ G X X Q X$^{19}$, wherein,
X$^1$ is Q or T,
X$^2$ is H, T or R,
X$^3$ is V or T,
X$^4$ is T or V,
X$^5$ is S, V or Q,
X$^6$ is A, Q or V,
X$^7$ is A, G or S,
X$^8$ is R or H,
X$^9$ is T, A or Q,
X$^{10}$ is T, A or V,
X$^{11}$ is S, H or R,
X$^{12}$ is G, S or R,
X$^{13}$ is T or V,
X$^{14}$ is S, G or R,
X$^{15}$ is S or R,
X$^{16}$ is P, L, S or Q,
X$^{17}$ is A, P or S,
X$^{18}$ is S, K or Q, and
X$^{19}$ is N or K.

3. A peptide according to claim 2 with an amino acid sequence selected from the group consisting of:

2.11 QTHTVGGVQGRQAHSLTSLFSPGASQN (SEQ ID NO: 2)
D6 QTTTTGGQVSHATHGLTGLFSLGPQQK (SEQ ID NO: 3)
D18 QTHTTGGSASHQASGLTRLFSQGPSQN (SEQ ID NO: 4)
F63 QTHVVGGQQGRQVSSLVSLFSPGASQK (SEQ ID NO: 5)
G31 TTHTVGGSVARQVHSLTGLFSPGPQQK (SEQ ID NO: 6)
L13 QTHTVGGSQAHAAHSLTRLFSPGSSQN (SEQ ID NO: 7)
M69 QTTVVGGSQARAAHGLVSLFSLGSKQN (SEQ ID NO: 8)
Z61 QTHVVGGVQGRQTSGLVGLFSPGSKQN (SEQ ID NO: 9)
R9 QTTVVGGSQSHTVRGLTSLFSPGASQN (SEQ ID NO: 10)
B26 TTTTTGGQAGHQAHSLTSLFSPGASQK (SEQ ID NO: 11)
B22 QTHVVGGVQSHQTSGLTSLFSPGASQK (SEQ ID NO: 12)
B35 QTHTTGGVQGHQTSRLTSLFSPGPSQN (SEQ ID NO: 13)
D29 TTTVVGGQAAHQTHSLTSLFSPGAKQN (SEQ ID NO: 14)
D33 TTTTTGGQQSHTVHGLVGLFSPGSKQN (SEQ ID NO: 15)
E26 QTHTVGGVQAHTVRGLTSLFSPGSSQN (SEQ ID NO: 16)
F80 QTHTTGGQAGHTASSLTGLFSPGAKQN (SEQ ID NO: 17)
F19 QTTTVGGVASHQAHSLTGLFSPGAKQK (SEQ ID NO: 18)
F78 QTHTTGGQAGHQAHSLTGLFSPGAKQN (SEQ ID NO: 19)
H1 QTHTTGGVVGHATSGLTSLFSPGPSQK (SEQ ID NO: 20)
L76 TTTTVGGQASHQTSSLTGLFSPGSKQN (SEQ ID NO: 21)
B24 TTTTVGGQASHTTSSLTGLFSPGASQK (SEQ ID NO: 37)
M63 QTHTTGGVVSHQTRSLVGLFSPGPQQN (SEQ ID NO: 38)
M27 QTTTTGGVASHAAHRLTSLFSPGPQQK (SEQ ID NO: 22)
M122 QTTTTGGSASHAVSSLTGLFSPGSKQN (SEQ ID NO: 23)
M129 QTTVVGGSAGHTASSLVGLFSPGSKQN (SEQ ID NO: 24)
M119 TTTTVGGQASHTTSSLTGLFSPGSQQN (SEQ ID NO: 25)
R5 QTHTTGGQASHQVSSLVSLFSPGAKQK (SEQ ID NO: 26)
R6 TTTTTGGQVGHQTSGLTGLFSPGAQQN (SEQ ID NO: 27)
R27 TTHVVGGSASHAVRGLTSLFSPGSSQN (SEQ ID NO: 28).

4. A peptide of any of the following amino acid sequences:

B14 QTTVTGQASHTTSSLTGLFSPGASQK (SEQ ID NO: 29)
B33 ATHATGGQAAHSTHSLTSLFSPGASQK (SEQ ID NO: 30)
F81 QTHVTGGSAAHQTGGLTGLFSPGPKQN (SEQ ID NO: 31)
B18 QTTVVGGQASHVSRLTGLFSPGSSQK (SEQ ID NO: 32)
E19 TTHTGGQQAHTTSRLVSLFSPGASQK (SEQ ID NO: 36)
L72 QTTTAAHTTSGLTGLFSPGAKQN (SEQ ID NO: 33)
D20 QTHVTGVAGRQTSGLVSLFSPGSSQN (SEQ ID NO: 34)
D30 QGGVQGHTTSSLVGLFSPGSQQN (SEQ ID NO: 35).

5. The peptide of claim 1, wherein said peptide consists of said amino acid sequence.

6. The peptide of claim 2, wherein said peptide consists of said amino acid sequence.

* * * * *

UNITED STATES PATENT AND TRADEMARK OFFICE
CERTIFICATE OF CORRECTION

PATENT NO. : 7,034,108 B1
APPLICATION NO. : 09/463098
DATED : April 25, 2006
INVENTOR(S) : A. Nicosia et al.

It is certified that error appears in the above-identified patent and that said Letters Patent is hereby corrected as shown below:

Column 129
Line 22:

"$X^{13} X^{14} L F X^{15} X^{16} G X X Q X^{19}$", should read
--$X^{13} X^{14} L F X^{15} X^{16} G X^{17} X^{18} Q X^{19}$,--

Signed and Sealed this

Twenty-fifth Day of December, 2007

JON W. DUDAS
*Director of the United States Patent and Trademark Office*